(12) United States Patent
Wuitschick et al.

(10) Patent No.: US 10,538,815 B2
(45) Date of Patent: Jan. 21, 2020

(54) EGFR ASSAY

(71) Applicant: ABBOTT MOLECULAR INC., Des Plaines, IL (US)

(72) Inventors: Jeffrey D. Wuitschick, Des Plaines, IL (US); Kevin S. Nelson, Des Plaines, IL (US); Shihai Huang, Des Plaines, IL (US); Rupinder Kular, Des Plaines, IL (US); Carolyn Mullen, Des Plaines, IL (US); James Rhoads, Des Plaines, IL (US)

(73) Assignee: ABBOTT MOLECULAR INC., Des Plaines, IL (US)

( * ) Notice: Subject to any disclaimer, the term of this patent is extended or adjusted under 35 U.S.C. 154(b) by 350 days.

(21) Appl. No.: 15/191,122

(22) Filed: Jun. 23, 2016

(65) Prior Publication Data

US 2016/0376665 A1 Dec. 29, 2016

Related U.S. Application Data

(60) Provisional application No. 62/183,566, filed on Jun. 23, 2015.

(51) Int. Cl.
| | | |
|---|---|---|
| C12Q 1/68 | (2018.01) | |
| C07H 19/207 | (2006.01) | |
| C12Q 1/6886 | (2018.01) | |

(52) U.S. Cl.
CPC ..... *C12Q 1/6886* (2013.01); *C12Q 2600/106* (2013.01); *C12Q 2600/158* (2013.01)

(58) Field of Classification Search
CPC .............. C12Q 1/6806; C12Q 2600/16; C12Q 2600/158
See application file for complete search history.

(56) References Cited

U.S. PATENT DOCUMENTS

| | | | |
|---|---|---|---|
| 4,988,617 A | 1/1991 | Landegren et al. | |
| 5,242,794 A | 9/1993 | Whiteley et al. | |
| 5,494,810 A | 2/1996 | Barany et al. | |
| 6,127,126 A | 10/2000 | Vogelstein et al. | |
| 6,582,938 B1 | 6/2003 | Su et al. | |
| 7,935,822 B2 | 5/2011 | Arden-Jacob et al. | |
| 2003/0003486 A1 | 1/2003 | Sauer et al. | |
| 2006/0179585 A1 | 8/2006 | Zilles et al. | |
| 2011/0172420 A1 | 7/2011 | Zilles et al. | |
| 2011/0190486 A1 | 8/2011 | Zilles et al. | |
| 2011/0223677 A1 | 9/2011 | Arden-Jacob et al. | |
| 2014/0161894 A1 | 6/2014 | MacLachlan et al. | |
| 2015/0038335 A1 | 2/2015 | Skog et al. | |

FOREIGN PATENT DOCUMENTS

| | | |
|---|---|---|
| WO | 2008033495 | 3/2008 |
| WO | 2008109373 | 9/2008 |
| WO | 2008119565 | 10/2008 |
| WO | WO-2009030239 A1 | 3/2009 |
| WO | 2010028054 | 3/2010 |
| WO | 2011035465 | 3/2011 |

OTHER PUBLICATIONS

Lowe et al. A computer program for selection of oligonucleotide primers for polymerase chain reactions. Nucleic Acids Research (1990) vol. 18, No. 7, pp. 1757-1761.*
Bustin S.A., . et al, "The MIQE Guidelines: Minimum Information for Publication of Quantitative Real-Time PCR Experiments," Journal of Clinical Chemistry, 2009, vol. 55 (4), pp. 611-622.
Doronina S.O., et al., "Novel Peptide Linkers for Highly Potent Antibody-Auristatin Conjugate," Bioconjugate Chemistry, 2008, vol. 19 (10), pp. 1960-1963.
Gan., et al., Journal of Clinical Oncology, 2013, vol. 31, Suppl Abstr 2520, NIH clinical trials identifier NCT01255657.
Gan., et al., Journal of Clinical Oncology, 2014, vol. 32 (5s), Suppl Abstr 2021, NIH clinical trials identifier NCT01800695.
Genbank, "*Homo sapiens* actin beta (ACTB), mRNA", Accession No. NM001101.3, May 2014 [retrieved on Nov. 16, 2016]. Retrieved from the Internet< URL: https://www.ncbi.nlm.nih.gov/nuccore/168480144?sat=21&satkey=4516507>.
Genbank, "Human mRNA for Precursor of Epidermal Growth Factor Receptor", Accession No. X00588.1, Oct. 2008 [retrieved on Nov. 16, 2016]. Retrieved from the Internet< URL: https://www.ncbi.nlm.nih.gov/nuccore/X00588.1>.
Giard D.J., et al., "In Vitro Cultivation of Human Tumors: Establishment of Cell Lines Derived From a Series of Solid Tumors," National Cancer Institute, 1973, vol. 51 (5), pp. 1417-1423.
International Search Report and Written Opinion for Application No. PCT/US2016/039041, dated Dec. 8, 2016, 17 pages.
Ji H., et al., "Epidermal Growth Factor Receptor Variant Iii Mutations in Lung Tumorigenesis and Sensitivity to Tyrosine Kinase Inhibitors," Proceedings of the National Academy of Sciences, 2006, vol. 103 (20), pp. 7817-7822.
Johns T.G., et al., "Novel Monoclonal Antibody Specific for the De2-7 Epidermal Growth Factor Receptor (EGFR) that also Recognizes the EGFR Expressed in Cells Containing Amplification of the EGFR Gene," International Journal of Cancer, 2002, vol. 98 (3), pp. 398-408.
Jungbluth A.A., et al., "A Monoclonal Antibody Recognizing Human Cancers with Amplification/Overexpression of the Human Epidermal Growth Factor Receptor," Proceedings of the National Academy of Sciences, 2003, vol. 100 (2), pp. 639-644.
Kohler G., et al., "Continuous Cultures of Fused Cells Secreting Antibody of Predefined Specificity ," Nature, 1975, vol. 256 (5517), pp. 495-497.
Maniatis T., et al., "Isolation of High-Molecular-Weight, Eukaryotic DNA from Cells Grown in Tissue Culture,"Molecular Cloning: A Laboratory manual, Cold Spring Harbor Laboratory, New York, 1982, pp. 280-281.
McIntyre J.B., et al., "Specific and Sensitive Hydrolysis Probe-Based Real-Time PCR Detection of Epidermal Growth Factor Receptor Variant III in Oral Squamous Cell Carcinoma," PLoS One, 2012, vol. 7 (2), pp. e31723.
Phillips., et al., Journal of Molecular Cancer Therapeutics ,2013, vol. 12 (11 Suppl), Abstract A250.

(Continued)

*Primary Examiner* — David C Thomas
(74) *Attorney, Agent, or Firm* — Casimir Jones, S.C.; Kirk J. Hogan

(57) ABSTRACT

Provided herein is technology relating to detecting molecular markers relevant to cancer and particularly, but not exclusively, to methods and compositions for quantifying and/or detecting EGFR mRNA and/or EGFRvIII mRNA in biological samples.

6 Claims, 34 Drawing Sheets

Specification includes a Sequence Listing.

(56) References Cited

OTHER PUBLICATIONS

Rae J.M., et al., "EGFR and EGFRvIII Expression in Primary Breast Cancer and Cell Lines," Journal of Breast Cancer Research and Treatment, 2004, vol. 87 (1), pp. 87-95.
Willis R.A., "The Spread of Tumors in the Human Body", London, Butterworth & Co, 1952.
Yoshimoto K., et al., "Development of a Real-Time RT-PCR Assay for Detecting EGFRvIII in Glioblastoma Samples," Clinical Cancer Research, 2008, vol. 14 (2), pp. 488-493.
Zapata G., et al., "Engineering Linear F(ab')2 Fragments for Efficient Production in *Escherichia coli* and Enhanced Antiproliferative Activity," Protein Engineering, 1995, vol. 8 (10), pp. 1057-1062.
Zhang Y., et al., "Development of ABT-806i, a Kit-Formulated 111In-ABT-806 Antibody Directed to EGFR for Tumor Imaging," Nuclear Medicine, 2013, vol. 54 (Supplement 2), pp. 396.
Wheelers, S. et al., "Tumor Epidermal Growth Factor Receptor and EGFR PY1068 are Independent Prognostic Indicators fro Head and Neck Squamous Cell Carcinoma", Clinical Cancer Research, vol. 18, No. 8, Feb. 20, 2012. pp. 2278-2289.
Extended European Search Report issued in corresponding European Application No. 16815314.6, dated Mar. 29, 2019.
Jul. 31, 2014 "Human/mouse EGFR gene-targeted siRNA, SEQ ID 8306.", retrieved from EBI accession No. GSN: BBH29120; Database accession No. BBH29120.
Dec. 11, 2008 "Cynomolgus Epidermal Growth factor receptor forward PCR primer # 1." retrieved from EBI accession No. GSN:ATS31349, Database accession No. ATS31349.
Nov. 13, 2008 "Human ERBB mRNA target sequence for mdRNA, SEQ ID:1346." retrieved from EBI accession No. GSN: ATM28002, Database accession No. ATM28002.
Feb. 19, 2001, "Nucleotide fragment of a mutant type II EGFR polypeptide", retrieved from EBI accession No. GSN: AAC61541; Database accession No. AAC61541.
Zhou et al., "EGFRvIII mRNA detection in the serum of patients with heptocellular carcinoma: Letters to the Editor", vol. 30, No. 6, Jul. 1, 2010, pp. 925-927.
"Sequence 15 from Patent WO2010028054", retrieved from EBI accession No. EM_PAT:HC480058, Database accession No. HC480058.

\* cited by examiner

FIG. 4

601 catgccatcc tgcgtctgga cctggctggc cgggacctga ctgactacct catgaagatc 661 ctcaccgagc gcggctacag cttcaccacc acggccgagc gggaaatcgt gcgtgacatt 721 aaggagaagc tgtgctacgt cgccctggac ttcgagcaag agatggccac ggctgcttcc 781 agctcctccc tggagaagag ctacgagctg cctgacggcc aggtcatcac cattggcaat 841 gagcggttcc gctgccctga ggcactcttc cagccttcct tctgggca guagtctgt 901 ggatccaatg aaactacctt caactccatc atgaagtgtg acgtgdacat ccgcaaagac 961 ctgtacgcca acacagtgct gtccggcgga accaccatgt accctggcat tgccgacagg 1021 atgcagaaag aaatcactgc cctggcacct agcacaatga agatcaagat cattgctcct 1081 cctgagcgca agtactccgt gtggatcggc ggctccatcc tggctcgct gtccaccttc 1141 cagcagatgt ggatcagcaa gcaggagtat gacgagtccg gcccctccat cgtccaccgc FIG. 13 (continued)

```
1201 aaatgcttct aggcggacta tgacttagtt gcgttacacc ctttcttgac aaaacctaac 1261 ttgcgcagaa aacaagatga gattggcatg gctttatttg tttttttgt tttgttttgg
                                                                              Exon 6

1321 tttttttttt tttttggct tgactcagga tttaaaaact ggaacggtga aggtgacagc 1381 agtcggttgg agcgagcatc ccccaaagtt cacaatgtgg ccgaggactt tgattgcaca 1441 ttgttgtttt tttaatagtc attccaaata tgagatgcgt tgttacagga agtcccttgc 1501 catcctaaaa gccacccac ttctctctaa ggagaatggc ccagtcctct cccaagtcca 1561 cacagggag gtgatagcat tgctttcgtg taaattatgt aatgcaaaat ttttttaatc 1621 ttcgccttaa tacttttta ttttgtttta ttttgaatga tgagccttcg tgccccccct 1681 tccccctttt ttgtccccca acttgagatg tatgaaggct tttggtctcc ctgggagtgg 1741 gtggaggcag ccaggcttaa cctgtacact gacttgagac cagttgaata aaagtgcaca 1801 ccttaaaaat gaaaaaaaa aaaaaaaaa aaaaaaaaa aaaaaaaaa aa
```

SEQ ID NO.: 44

FIG. 13 (continued)

1   ▨▨▨▨▨▨▨▨▨▨▨▨▨▨▨▨▨▨▨▨▨▨▨▨▨▨▨▨▨▨▨▨▨▨▨▨▨▨▨▨▨▨▨▨▨▨▨▨▨▨▨▨  Exon 1

▨▨▨▨▨▨▨▨▨▨▨▨▨▨▨▨▨agccctt cagcggccag tagcatctga ctttgagcct 121 cagggtctga gtgaagccgc tcgttggaac tccaaggaaa accttctcgc tggacccagt
                                                                          Exon 2
181 gaaaatgacc ccaacctttt cgttgcactg tatgattttg tggccagtgg agataacact 241 ctaagcataa ctaaag▨▨▨▨▨▨▨▨▨▨▨▨▨▨▨▨▨▨▨▨▨▨▨▨▨▨▨▨▨▨▨▨▨▨▨▨

▨▨▨▨▨▨▨▨▨▨▨▨▨▨▨▨▨▨▨▨▨▨▨▨▨▨▨▨▨▨▨▨▨▨▨▨▨▨▨▨▨▨▨▨▨▨▨▨▨▨▨▨▨▨

▨▨▨▨▨▨▨▨▨▨▨▨▨▨▨▨▨▨▨▨▨▨▨▨▨▨▨▨▨▨▨▨▨▨▨▨▨▨▨▨▨▨▨▨▨▨▨▨▨▨▨▨▨▨  Exon 3

▨▨▨▨▨▨▨▨▨▨▨▨▨▨▨▨▨▨▨▨▨▨▨▨▨▨▨▨▨▨▨▨▨▨▨▨▨▨▨▨▨▨▨▨▨▨▨▨▨▨▨▨▨▨

▨▨▨▨▨▨▨▨▨▨▨▨▨▨▨▨▨▨▨▨▨▨▨▨▨▨▨▨▨▨▨▨▨▨▨▨▨▨▨▨▨▨▨▨▨▨▨▨▨▨▨▨▨▨

ABLi3 fwd -21to+2 →           ABLi3+9to+33p                     ←
▨▨▨▨▨▨▨▨▨▨▨▨▨▨ct ctacgt ctcctccgag agccgcttca acaccctggc cgagttggtt
        ABLi3+65to+41
601 catcatcatt caacggtggc cgacgggctc atcaccacgc tccattatcc agccccaaag
                                                                          Exon 4
661 cgcaacaagc ccactgtcta tggtgtgtcc cccaactacg acaagtggga gatggaacgc 721 acggacatca ccatgaagca caagctgggc ggggccagt acggggaggt gtacgagggc

FIG. 14

```
 781 gtgtggaaga aatacagcct gacggtggcc gtgaagacct tgaagg              Exon 5 gggtctgcac ccgggagccc ccgttctata tcatcactga gttcatgacc
 961 tacgggaacc tcctggacta cctgagggag tgcaacggc aggaggtgaa cgccgtggtg  Exon 6
1021 ctgctgtaca tggccactca gatctcgtca gccatggagt acctggagaa gaaaaacttc
1081 atccacaga                                                        Exon 7 catttgg agtattgctt tgggaaattg ctacctatgg catgtccct  Exon 8
1321 tacccgggaa ttgacctgtc ccaggtgtat gagctgctag agaaggacta ccgcatggag
1381 cgccagaag gctgcccaga gaaggtctat gaactcatgc gagcat                Exon 9 aagt ggaaaaggag ctggggaaac aaggcgtccg tggggctgtg
1561 agtaccttgc tgcaggcccc agagctgccc accaagacga ggacctccag gagagctgca  Exon 10
1621 gagcacagag acaccactga cgtgcctgag atgcctcact ccaagggcca gggagagagc
1681 g
```

FIG. 14 (continued)

FIG. 14 (continued)    SEQ ID NO.: 45

1   [obscured]

61  [obscured] cagc gtcatggcag 121 agcaggtggc cctgagccgg acccaggtgt gcgggatcct gcgggaagag cttttccagg
                G6PDi2 fwd-57to-39                         G6PDv1 fwd346to367PROBE2cy5
181 gcgatgcctt ccatcagtcg gataca caca tattcatcat catgggtgca tcg[obscured]
                    G6PDi2 rsv-57to-12
241 [obscured] gtggctgtt ccgggatggc cttctgccg 301 aaaacaccct catcgtgggc tatgcccgtt cccgcctcac agtggctgac atccgcaaac 361 agagtgagcc cttcttcaag [obscured]

421 [obscured]

481 [obscured]

541 [obscured]g 601 gctggaaccg catcatcgtg gagaagccct tcgggaggga cctgcagagc tctgaccggc 661 tgtccaacca catctcctcc ctgttccgtg aggaccagat ctaccgcatc gaccactacc 721 tgggcaagga gatggtgcag aacctcatgg tgctgag[obscured]

781 [obscured]

841 [obscured] gacgtg atgcagaacc 901 acctactgca gatgctgtgt ctggtggcca tggagaagcc cgcctccacc aactcagatg 961 acgtccgtga tgagaag[obscured]

1021 [obscured]

1081 [obscured]

FIG. 15

```
1141                                  ggtgc ccttcatcct gcgctgcggc aaggccctga
1201 acgagcgcaa ggccgaggtg aggctgcagt tcatgatgt ggccggcgac atcttccacc
1261 agcagtgcaa gcgcaacgag ctggtgatcc gcgtgcagcc caacgaggcc gtgtacacca
1321 agatgatgac caagaagccg ggcatgttct tcaaccccga ggagtcggag ctggacctga
1381 cctacggcaa cagatacaag
                                                               ga cgagctccgt gaggcctggc
1501 gtattttcac cccactgctg caccagattg agctggagaa gcccaagccc atccctata
1561 tttatggcag
```

FIG. 15 (continued)   SEQ ID NO.: 46

SEQUENCE LISTING

```
<160> NUMBER OF SEQ ID NOS: 51

<210> SEQ ID NO 1
<211> LENGTH: 18
<212> TYPE: DNA
<213> ORGANISM: Homo sapiens

<400> SEQUENCE: 1
accacataat tacctttc                                                   18

<210> SEQ ID NO 2
<211> LENGTH: 18
<212> TYPE: DNA
<213> ORGANISM: Homo sapiens

<400> SEQUENCE: 2
ctcctggcgc tgctggct                                                   18
```

```
<210> SEQ ID NO 3
<211> LENGTH: 19
<212> TYPE: DNA
<213> ORGANISM: Homo sapiens

<400> SEQUENCE: 3
cgctctgccc ggcgagtcg                                              19

<210> SEQ ID NO 4
<211> LENGTH: 13
<212> TYPE: DNA
<213> ORGANISM: Homo sapiens

<400> SEQUENCE: 4
accacataat tac                                                    13

<210> SEQ ID NO 5
<211> LENGTH: 5
<212> TYPE: DNA
<213> ORGANISM: Homo sapiens

<400> SEQUENCE: 5 ctttc                                                              5

<210> SEQ ID NO 6
<211> LENGTH: 19
<212> TYPE: DNA
<213> ORGANISM: Homo sapiens

<400> SEQUENCE: 6
cgactcgccg ggcagagcg                                              19

<210> SEQ ID NO 7
<211> LENGTH: 26
<212> TYPE: DNA
<213> ORGANISM: Homo sapiens

<400> SEQUENCE: 7
gggaacggac tggtttatgt attcag                                      26

<210> SEQ ID NO 8
<211> LENGTH: 23
<212> TYPE: DNA
<213> ORGANISM: Homo sapiens

<400> SEQUENCE: 8
cgccttgact gaggacagca tag                                         23

<210> SEQ ID NO 9
<211> LENGTH: 14
<212> TYPE: DNA
<213> ORGANISM: Homo sapiens

<400> SEQUENCE: 9
acgacacctt cctc                                                   14

<210> SEQ ID NO 10
<211> LENGTH: 23
<212> TYPE: DNA
<213> ORGANISM: Homo sapiens

<400> SEQUENCE: 10
gggaacggac tggtttatgt att                                         23
```

```
<210> SEQ ID NO 11
<211> LENGTH: 3
<212> TYPE: DNA
<213> ORGANISM: Homo sapiens

<400> SEQUENCE: 11 cag                                                                        3

<210> SEQ ID NO 12
<211> LENGTH: 14
<212> TYPE: DNA
<213> ORGANISM: Homo sapiens

<400> SEQUENCE: 12
gaggaaggtg tcgt                                                           14

<210> SEQ ID NO 13
<211> LENGTH: 22
<212> TYPE: DNA
<213> ORGANISM: Homo sapiens

<400> SEQUENCE: 13
tcatcatcca tggtgagctg gc                                                  22

<210> SEQ ID NO 14
<211> LENGTH: 21
<212> TYPE: DNA
<213> ORGANISM: Homo sapiens

<400> SEQUENCE: 14
gagcacagag cctcgccttt g                                                   21

<210> SEQ ID NO 15
<211> LENGTH: 20
<212> TYPE: DNA
<213> ORGANISM: Homo sapiens

<400> SEQUENCE: 15
atccgccgcc cgtccacacc                                                     20

<210> SEQ ID NO 16
<211> LENGTH: 17
<212> TYPE: DNA
<213> ORGANISM: Homo sapiens

<400> SEQUENCE: 16
tcatcatcca tggtgag                                                        17

<210> SEQ ID NO 17
<211> LENGTH: 5
<212> TYPE: DNA
<213> ORGANISM: Homo sapiens

<400> SEQUENCE: 17 ctggc                                                                      5

<210> SEQ ID NO 18
<211> LENGTH: 20
<212> TYPE: DNA
<213> ORGANISM: Homo sapiens

<400> SEQUENCE: 18
ggtgtggacg ggcggcggat                                                     20
```

```
<210> SEQ ID NO 19
<211> LENGTH: 25
<212> TYPE: DNA
<213> ORGANISM: Homo sapiens

<400> SEQUENCE: 19
accgttgaat gatgatgaac caact                                       25

<210> SEQ ID NO 20
<211> LENGTH: 23
<212> TYPE: DNA
<213> ORGANISM: Homo sapiens

<400> SEQUENCE: 20
aacactgctt ctgatggcaa gct                                         23

<210> SEQ ID NO 21
<211> LENGTH: 25
<212> TYPE: DNA
<213> ORGANISM: Homo sapiens

<400> SEQUENCE: 21
ctcctccgag agccgcttca acacc                                       25

<210> SEQ ID NO 22
<211> LENGTH: 26
<212> TYPE: DNA
<213> ORGANISM: Homo sapiens

<400> SEQUENCE: 22
agatggtggg gtagatcttc ttcttg                                      26

<210> SEQ ID NO 23
<211> LENGTH: 23
<212> TYPE: DNA
<213> ORGANISM: Homo sapiens

<400> SEQUENCE: 23
atgccttcca tcagtcggat aca                                         23

<210> SEQ ID NO 24
<211> LENGTH: 22
<212> TYPE: DNA
<213> ORGANISM: Homo sapiens

<400> SEQUENCE: 24
catgggtgca tcgggtgacc tg                                          22

<210> SEQ ID NO 25
<211> LENGTH: 21
<212> TYPE: DNA
<213> ORGANISM: Homo sapiens

<400> SEQUENCE: 25
aacactgctt ctgatggcaa g                                           21

<210> SEQ ID NO 26
<211> LENGTH: 2
<212> TYPE: DNA
<213> ORGANISM: Homo sapiens

<400> SEQUENCE: 26 ct                                                                 2
```

<210> SEQ ID NO 27
<211> LENGTH: 13
<212> TYPE: DNA
<213> ORGANISM: Homo sapiens

<400> SEQUENCE: 27
catgggtgca tcg                                                          13

<210> SEQ ID NO 28
<211> LENGTH: 9
<212> TYPE: DNA
<213> ORGANISM: Homo sapiens

<400> SEQUENCE: 28 ggtgacctg                                                                9

<210> SEQ ID NO 29
<211> LENGTH: 25
<212> TYPE: DNA
<213> ORGANISM: Homo sapiens

<400> SEQUENCE: 29
ggtgttgaag cggctctcgg aggag                                             25

<210> SEQ ID NO 30
<211> LENGTH: 22
<212> TYPE: DNA
<213> ORGANISM: Homo sapiens

<400> SEQUENCE: 30
caggtcaccc gatgcaccca tg                                                22

<210> SEQ ID NO 31
<211> LENGTH: 29
<212> TYPE: DNA
<213> ORGANISM: Homo sapiens

<400> SEQUENCE: 31
cgtgatctgt caccacataa ttacctttc                                         29

<210> SEQ ID NO 32
<211> LENGTH: 17
<212> TYPE: DNA
<213> ORGANISM: Homo sapiens
<220> FEATURE:
<221> NAME/KEY: misc_feature
<222> LOCATION: (2)..(2)
<223> OTHER INFORMATION: 5-methyl dC
<220> FEATURE:
<221> NAME/KEY: misc_feature
<222> LOCATION: (5)..(5)
<223> OTHER INFORMATION: 5-methyl dC
<220> FEATURE:
<221> NAME/KEY: misc_feature
<222> LOCATION: (6)..(6)
<223> OTHER INFORMATION: 5-propynyl dU
      C
<220> FEATURE:
<221> NAME/KEY: misc_feature
<222> LOCATION: (7)..(7)
<223> OTHER INFORMATION: 5-propynyl dU
      C
<220> FEATURE:
<221> NAME/KEY: misc_feature
<222> LOCATION: (8)..(8)
<223> OTHER INFORMATION: 5-methyl dC

```
<220> FEATURE:
<221> NAME/KEY: misc_feature
<222> LOCATION: (10)..(10)
<223> OTHER INFORMATION: 5-propynyl dU
      C
<220> FEATURE:
<221> NAME/KEY: misc_feature
<222> LOCATION: (11)..(11)
<223> OTHER INFORMATION: 5-methyl dC
<220> FEATURE:
<221> NAME/KEY: misc_feature
<222> LOCATION: (13)..(13)
<223> OTHER INFORMATION: 5-methyl dC
<220> FEATURE:
<221> NAME/KEY: misc_feature
<222> LOCATION: (16)..(16)
<223> OTHER INFORMATION: 5-propynyl dU
      C

<400> SEQUENCE: 32
anacnnnncn ncnagng                                                  17

<210> SEQ ID NO 33
<211> LENGTH: 29
<212> TYPE: DNA
<213> ORGANISM: Homo sapiens

<400> SEQUENCE: 33
cgtgatctgt caccacataa ttacctttc                                     29

<210> SEQ ID NO 34
<211> LENGTH: 20
<212> TYPE: DNA
<213> ORGANISM: Homo sapiens

<400> SEQUENCE: 34
ggtgccacct gcgtgaagaa                                               20

<210> SEQ ID NO 35
<211> LENGTH: 19
<212> TYPE: DNA
<213> ORGANISM: Homo sapiens

<400> SEQUENCE: 35
ggacgcacga gccgtgatc                                                19

<210> SEQ ID NO 36
<211> LENGTH: 15
<212> TYPE: DNA
<213> ORGANISM: Homo sapiens

<400> SEQUENCE: 36
tgtccccgta attat                                                    15

<210> SEQ ID NO 37
<211> LENGTH: 23
<212> TYPE: DNA
<213> ORGANISM: Homo sapiens

<400> SEQUENCE: 37
atgccttcca tcagtcggat aca                                           23

<210> SEQ ID NO 38
<211> LENGTH: 17
<212> TYPE: DNA
<213> ORGANISM: Homo sapiens
```

```
<400> SEQUENCE: 38
acaccttcct cccagtg                                                    17

<210> SEQ ID NO 39
<211> LENGTH: 17
<212> TYPE: DNA
<213> ORGANISM: Homo sapiens
<220> FEATURE:
<221> NAME/KEY: misc_feature
<222> LOCATION: (2)..(2)
<223> OTHER INFORMATION: 5-methyl dC
<220> FEATURE:
<221> NAME/KEY: misc_feature
<222> LOCATION: (5)..(5)
<223> OTHER INFORMATION: 5-methyl dC
<220> FEATURE:
<221> NAME/KEY: misc_feature
<222> LOCATION: (6)..(6)
<223> OTHER INFORMATION: 5-propynyl dU
      C
<220> FEATURE:
<221> NAME/KEY: misc_feature
<222> LOCATION: (7)..(7)
<223> OTHER INFORMATION: 5-propynyl dU
      C
<220> FEATURE:
<221> NAME/KEY: misc_feature
<222> LOCATION: (8)..(8)
<223> OTHER INFORMATION: 5-methyl dC
<220> FEATURE:
<221> NAME/KEY: misc_feature
<222> LOCATION: (10)..(10)
<223> OTHER INFORMATION: 5-propynyl dU
      C
<220> FEATURE:
<221> NAME/KEY: misc_feature
<222> LOCATION: (11)..(11)
<223> OTHER INFORMATION: 5-methyl dC
<220> FEATURE:
<221> NAME/KEY: misc_feature
<222> LOCATION: (13)..(13)
<223> OTHER INFORMATION: 5-methyl dC
<220> FEATURE:
<221> NAME/KEY: misc_feature
<222> LOCATION: (16)..(16)
<223> OTHER INFORMATION: 5-propynyl dU
      C

<400> SEQUENCE: 39
anacnnnncn ncnagng                                                    17

<210> SEQ ID NO 40
<211> LENGTH: 17
<212> TYPE: DNA
<213> ORGANISM: Homo sapiens
<220> FEATURE:
<221> NAME/KEY: misc_feature
<222> LOCATION: (2)..(2)
<223> OTHER INFORMATION: 5-propynyl dC
<220> FEATURE:
<221> NAME/KEY: misc_feature
<222> LOCATION: (5)..(5)
<223> OTHER INFORMATION: 5-propynyl dC
<220> FEATURE:
<221> NAME/KEY: misc_feature
<222> LOCATION: (6)..(6)
<223> OTHER INFORMATION: 5-propynyl dU
      C
<220> FEATURE:
<221> NAME/KEY: misc_feature
<222> LOCATION: (7)..(7)
<223> OTHER INFORMATION: 5-propynyl dU
      C
```

```
<220> FEATURE:
<221> NAME/KEY: misc_feature
<222> LOCATION: (8)..(8)
<223> OTHER INFORMATION: 5-propynyl dC
<220> FEATURE:
<221> NAME/KEY: misc_feature
<222> LOCATION: (10)..(10)
<223> OTHER INFORMATION: 5-propynyl dU
      C
<220> FEATURE:
<221> NAME/KEY: misc_feature
<222> LOCATION: (11)..(11)
<223> OTHER INFORMATION: 5-propynyl dC
<220> FEATURE:
<221> NAME/KEY: misc_feature
<222> LOCATION: (13)..(13)
<223> OTHER INFORMATION: 5-propynyl dC
<220> FEATURE:
<221> NAME/KEY: misc_feature
<222> LOCATION: (16)..(16)
<223> OTHER INFORMATION: 5-propynyl dU
      C

<400> SEQUENCE: 40
anacnnnncn ncnagng                                                  17

<210> SEQ ID NO 41
<211> LENGTH: 17
<212> TYPE: DNA
<213> ORGANISM: Homo sapiens
<220> FEATURE:
<221> NAME/KEY: misc_feature
<222> LOCATION: (2)..(2)
<223> OTHER INFORMATION: 5-methyl dC
      U
<220> FEATURE:
<221> NAME/KEY: misc_feature
<222> LOCATION: (5)..(5)
<223> OTHER INFORMATION: 5-propynyl dC
<220> FEATURE:
<221> NAME/KEY: misc_feature
<222> LOCATION: (6)..(6)
<223> OTHER INFORMATION: 5-propynyl dU
      C
<220> FEATURE:
<221> NAME/KEY: misc_feature
<222> LOCATION: (7)..(7)
<223> OTHER INFORMATION: 5-propynyl dU
      C
<220> FEATURE:
<221> NAME/KEY: misc_feature
<222> LOCATION: (8)..(8)
<223> OTHER INFORMATION: 5-methyl dC
      U
<220> FEATURE:
<221> NAME/KEY: misc_feature
<222> LOCATION: (10)..(10)
<223> OTHER INFORMATION: 5-propynyl dU
      C
<220> FEATURE:
<221> NAME/KEY: misc_feature
<222> LOCATION: (11)..(11)
<223> OTHER INFORMATION: 5-propynyl dC
<220> FEATURE:
<221> NAME/KEY: misc_feature
<222> LOCATION: (13)..(13)
<223> OTHER INFORMATION: 5-propynyl dC
<220> FEATURE:
<221> NAME/KEY: misc_feature
<222> LOCATION: (16)..(16)
<223> OTHER INFORMATION: 5-propynyl dU
      C

<400> SEQUENCE: 41
anacnnnncn ncnagng                                                  17
```

-continued

```
<210> SEQ ID NO 42
<211> LENGTH: 19
<212> TYPE: DNA
<213> ORGANISM: Homo sapiens

<400> SEQUENCE: 42
cgctctgccc ggcgagtcg                                               19

<210> SEQ ID NO 43
<211> LENGTH: 20
<212> TYPE: DNA
<213> ORGANISM: Homo sapiens

<400> SEQUENCE: 43
atccgccgcc cgtccacacc                                              20

<210> SEQ ID NO 44
<211> LENGTH: 1852
<212> TYPE: DNA
<213> ORGANISM: Homo sapiens

<400> SEQUENCE: 44
accgccgaga ccgcgtccgc cccgcgagca cagagcctcg cctttgccga tccgccgccc    60
gtccacaccc gccgccagct caccatggat gatgatatcg ccgcgctcgt cgtcgacaac   120
ggctccggca tgtgcaaggc cggcttcgcg ggcgacgatg ccccccgggc cgtcttcccc   180
tccatcgtgg ggcgccccag gcaccagggc gtgatggtgg gcatgggtca gaaggattcc   240
tatgtgggcg acgaggccca gagcaagaga ggcatcctca ccctgaagta ccccatcgag   300
cacggcatcg tcaccaactg ggacgacatg gagaaaatct ggcaccacac cttctacaat   360
gagctgcgtg tggctcccga ggagcacccc gtgctgctga ccgaggcccc cctgaacccc   420
aaggccaacc gcgagaagat gacccagatc atgtttgaga ccttcaacac cccagccatg   480
tacgttgcta tccaggctgt gctatccctg tacgcctctg gccgtaccac tggcatcgtg   540
atggactccg gtgacggggt cacccacact gtgcccatct acgagggta tgccctcccc   600 catgccatcc tgcgtctgga cctggctggc cgggacctga ctgactacct catgaagatc   660
ctcaccgagc gcggctacag cttcaccacc acggccgagc gggaaatcgt gcgtgacatt   720
aaggagaagc tgtgctacgt cgccctggac ttcgagcaag agatggccac ggctgcttcc   780
agctcctccc tggagaagag ctacgagctg cctgacggcc aggtcatcac cattggcaat   840
gagcggttcc gctgccctga ggcactcttc cagccttcct tcctgggcat ggagtcctgt   900
ggcatccacg aaactacctt caactccatc atgaagtgtg acgtggacat ccgcaaagac   960
ctgtacgcca acacagtgct gtctggcggc accaccatgt accctggcat tgccgacagg  1020
atgcagaagg agatcactgc cctggcaccc agcacaatga agatcaagat cattgctcct  1080
cctgagcgca aagtactccgt gtggatcggc ggctccatcc tggcctcgct gtccaccttc  1140
cagcagatgt ggatcagcaa gcaggagtat gacgagtccg gccctccat cgtccaccgc  1200 aaatgcttct aggcggacta tgacttagtt gcgttacacc ctttcttgac aaaacctaac  1260
ttgcgcagaa acaagatgag attggcatg gcttttattg ttttttttgt tttgttttgg  1320 ttttttttttt tttttggct tgactcagga tttaaaaact ggaacggtga aggtgacagc  1380
agtcggttgg agcagcatc ccccaaagtt cacaatgtgg ccgaggactt tgattgcaca  1440 ttgttgttttt tttaatagtc attccaaata tgagatgcgt tgttacagga agtcccttgc  1500
catcctaaaa gccaccccac ttctctctaa ggagaatggc ccagtcctct cccaagtcca  1560
```

```
cacagggag  gtgatagcat  tgctttcgtg  taaattatgt  aatgcaaaat  ttttttaatc    1620
ttcgccttaa  tactttttta  ttttgtttta  ttttgaatga  tgagccttcg  tgcccccct     1680 tccccctttt  ttgtccccca  acttgagatg  tatgaaggct  tttggtctcc  ctgggagtgg    1740
gtggaggcag  ccagggctta  cctgtacact  gacttgagac  cagttgaata  aaagtgcaca    1800
ccttaaaaat  gaaaaaaaaa  aaaaaaaaaa  aaaaaaaaaa  aaaaaaaaaa  aa            1852

<210> SEQ ID NO 45
<211> LENGTH: 5388
<212> TYPE: DNA
<213> ORGANISM: Homo sapiens

<400> SEQUENCE: 45
aaaatgttgg  agatctgcct  gaagctggtg  ggctgcaaat  ccaagaaggg  gctgtcctcg      60
tcctccagct  gttatctgga  agaagccctt  cagcggccag  tagcatctga  ctttgagcct    120
cagggtctga  gtgaagccgc  tcgttggaac  tccaaggaaa  accttctcgc  tggacccagt    180
gaaaatgacc  ccaacctttt  cgttgcactg  tatgattttg  tggccagtgg  agataacact    240
ctaagcataa  ctaaaggtga  aaagctccgg  tcttaggct   ataatcacaa  tggggaatgg    300
tgtgaagccc  aaaccaaaaa  tggccaaggc  tgggtcccaa  gcaactacat  cacgccagtc    360
aacagtctgg  agaaacactc  ctggtaccat  gggcctgtgt  cccgcaatgc  cgctgagtat    420
ctgctgagca  gcgggatcaa  tggcagcttc  ttggtgcgtg  agagtgagag  cagtcctggc    480
cagaggtcca  tctcgctgag  atacgaaggg  agggtgtacc  attacaggat  caacactgct    540
tctgatggca  agctctacgt  ctcctccgag  agccgcttca  cacccctggc  cgagttggtt    600
catcatcatt  aacggtggc   cgacgggctc  atcaccacgc  tccattatcc  agccccaaag    660
cgcaacaagc  ccactgtcta  tggtgtgtcc  cccaactacg  acaagtggga  gatgaacgc     720 acggacatca  ccatgaagca  caagctgggc  gggggccagt  acggggaggt  gtacgagggc    780
gtgtggaaga  atacagcct   gacggtggcc  gtgaagacct  tgaaggagga  caccatggag    840
gtggaagagt  tcttgaaaga  agctgcagtc  atgaaagaga  tcaaacaccc  taacctggtg    900
cagctccttg  gggtctgcac  ccgggagccc  ccgttctata  tcatcactga  gttcatgacc    960
tacgggaacc  tcctggacta  cctgagggag  tgcaaccggc  aggaggtgaa  cgccgtggtg    1020
ctgctgtaca  tggccactca  gatctcgtca  gccatggagt  acctggagaa  gaaaaacttc    1080
atccacagag  atcttgctgc  cgaaactgc   ctggtagggg  agaaccactt  ggtgaaggta    1140
gctgattttg  gcctgagcag  gttgatgaca  ggggacacct  acacagccca  tgctggagcc    1200
aagttcccca  tcaaatggac  tgcacccgag  agcctggcct  acaacaagtt  ctccatcaag    1260
tccgacgtct  gggcatttgg  agtattgctt  tgggaaattg  ctacctatgg  catgtcccct    1320
tacccgggaa  ttgacctgtc  ccaggtgtat  gagctgctag  agaaggacta  ccgcatggag    1380
cgcccagaag  gctgcccaga  gaaggtctat  gaactcatgc  gagcatgttg  gcagtggaat    1440
ccctctgacc  ggccctcctt  tgctgaaatc  caccaagcct  ttgaaacaat  gttccaggaa    1500
tccagtatct  cagacgaagt  ggaaaaggag  ctggggaaac  aaggcgtccg  tggggctgtg    1560
agtaccttgc  tgcaggcccc  agagctgccc  accaagacga  ggacctccag  gagagctgca    1620
gagcacagag  acaccactga  cgtgcctgag  atgcctcact  ccaagggcca  gggagagagc    1680
gatcctctgg  accatgagcc  tgccgtgtct  ccattgctcc  ctcgaaaaga  gcgaggtccc    1740
ccggagggcg  gcctgaatga  agatgagcgc  cttctcccca  aagacaaaaa  gaccaacttg    1800
ttcagcgcct  tgatcaagaa  gaagaagaag  acagcccaa   cccctcccaa  acgcagcagc    1860
```

-continued

```
tccttccggg agatggacgg ccagccggag cgcagagggg ccggcgagga agagggccga    1920
gacatcagca acgggcact ggctttcacc cccttggaca cagctgaccc agccaagtcc    1980
ccaaagccca gcaatggggc tggggtcccc aatggagccc tccgggagtc cggggggctca   2040 ggcttccggt ctccccacct gtggaagaag tccagcacgc tgaccagcag ccgcctagcc    2100
accggcgagg aggagggcgg tggcagctcc agcaagcgct tcctgcgctc ttgctccgcc    2160
tcctgcgttc cccatggggc caaggacacg gagtggaggt cagtcacgct gcctcgggac    2220
ttgcagtcca cgggaagaca gtttgactcg tccacatttg gagggcacaa aagtgagaag    2280
ccggctctgc ctcggaagag ggcagggag aacaggtctg accaggtgac ccgaggcaca    2340
gtaacgcctc cccccaggct ggtgaaaaag aatgaggaag ctgctgatga ggtcttcaaa    2400
gacatcatgg agtccagccc gggctccagc ccgcccaacc tgactccaaa acccctccgg    2460
cggcaggtca ccgtggcccc tgcctcgggc ctcccccaca aggaagaagc tggaaagggc    2520
agtgccttag ggacccctgc tgcagctgag ccagtgaccc ccaccagcaa agcaggctca    2580
ggtgcaccag ggggcaccag caagggcccc gccgaggagt ccagagtgag gaggcacaag    2640
cactcctctg agtcgccagg gagggacaag gggaaattgt ccaggctcaa acctgccccg    2700 ccgccccac cagcagcctc tgcagggaag gctggaggaa agccctcgca gagcccgagc    2760
caggaggcgg ccggggaggc agtcctgggc gcaaagacaa aagccacgag tctggttgat    2820
gctgtgaaca gtgacgctgc caagcccagc cagccgggag agggcctcaa aaagcccgtg    2880
ctcccggcca ctccaaagcc acagtccgcc aagccgtcgg ggaccccat cagcccagcc    2940 cccgttccct ccacgttgcc atcagcatcc tcggccctgg caggggacca gccgtcttcc    3000
accgccttca tccctctcat atcaacccga gtgtctcttc ggaaaacccg ccagcctcca    3060
gagcggatcg ccagcggcgc catcaccaag ggcgtggtcc tggacagcac cgaggcgctg    3120
tgcctcgcca tctctaggaa ctccgagcag atggccagcc acagcgcagt gctggaggcc    3180
ggcaaaaacc tctacacgtt ctgcgtgagc tatgtggatt ccatccagca aatgaggaac    3240
aagtttgcct tccgagaggc catcaacaaa ctggagaata tctccgggga gcttcagatc    3300
tgcccggcga cagcaggcag tggtccagcg gccactcagg acttcagcaa gctcctcagt    3360
tcggtgaagg aaatcagtga catagtgcag aggtagcagc agtcaggggt caggtgtcag    3420
gcccgtcgga gctgcctgca gcacatgcgg gctcgcccat acccgtgaca gtggctgaca    3480
agggactagt gagtcagcac cttggcccag gagctctgcg ccaggcagag ctgagggccc    3540
tgtggagtcc agctctacta cctacgtttg caccgcctgc cctcccgcac cttcctcctc    3600
cccgctccgt ctctgtcctc gaattttatc tgtggagttc ctgctccgtg gactgcagtc    3660
ggcatgccag acccgccag ccccgctccc acctagtgcc ccagactgag ctctccaggc    3720
caggtgggaa cggctgatgt ggactgtctt tttcattttt ttctctctgg agcccctcct    3780
cccccggctg ggcctccttc ttccacttct ccaagaatgg aagcctgaac tgaggccttg    3840
tgtgtcaggc cctctgcctg cactccctgg ccttgcccgt cgtgtgctga agacatgttt    3900
caagaaccgc atttcgggaa gggcatgcac gggcatgcac acggctggtc actctgccct    3960
ctgctgctgc ccggggtggg gtgcactcgc catttcctca cgtgcaggac agctcttgat    4020
ttgggtggaa aacagggtgc taaagccaac cagcctttgg gtcctgggca ggtgggagct    4080
gaaaaggatc gaggcatggg gcatgtcctt tccatctgtc cacatcccca gagcccagct    4140
cttgctctct tgtgacgtgc actgtgaatc ctggcaagaa agcttgagtc tcaagggtgg    4200
caggtcactg tcactgccga catccctccc ccagcagaat ggaggcaggg gacaagggag    4260
```

```
gcagtggcta gtggggtgaa cagctggtgc caaatagccc cagactgggc ccaggcaggt    4320
ctgcaagggc ccagagtgaa ccgtcctttc acacatctgg gtgccctgaa agggcccttc    4380
ccctccccca ctcctctaag acaaagtaga ttcttacaag gccctttcct ttggaacaag    4440
acagccttca cttttctgag ttcttgaagc atttcaaagc cctgcctctg tgtagccgcc    4500
ctgagagaga atagagctgc cactgggcac ctgcgcacag gtgggaggaa agggcctggc    4560
cagtcctggt cctggctgca ctcttgaact gggcgaatgt cttatttaat taccgtgagt    4620
gacatagcct catgttctgt gggggtcatc agggagggtt aggaaaacca caaacggagc    4680
ccctgaaagc ctcacgtatt tcacagagca cgcctgccat cttctcccg aggctgcccc    4740 aggccggagc ccagatacgg gggctgtgac tctgggcagg acccggggt tcctggacc     4800 ttgacagagc agctaactcc gagagcagtg ggcaggtggc cgcccctgag gcttcacgcc    4860
gggagaagcc accttcccac cccttcatac cgcctcgtgc cagcagcctc gcacaggccc    4920
tagctttacg ctcatcacct aaacttgtac tttattttc tgatagaaat ggtttcctct    4980
ggatcgtttt atgcggttct tacagcacat cacctctttg cccccgacgg ctgtgacgca    5040
gccggaggga ggcactagtc accgacagcg gccttgaaga cagagcaaag cgcccaccca    5100
ggtcccccga ctgcctgtct ccatgaggta ctggtcccctt ccttttgtta acgtgatgtg   5160
ccactatatt ttacacgtat ctcttggtat gcatctttta tagacgctct tttctaagtg    5220
gcgtgtgcat agcgtcctgc cctgcccct cgggggcctg tggtggctcc cctctgctt     5280 ctcggggtcc agtgcatttt gtttctgtat atgattctct gtggtttttt ttgaatccaa    5340
atctgtcctc tgtagtattt tttaaataaa tcagtgttta cattagaa               5388

<210> SEQ ID NO 46
<211> LENGTH: 2270
<212> TYPE: DNA
<213> ORGANISM: Homo sapiens

<400> SEQUENCE: 46
cgagaactcg ggaagccggc gagaagtgtg aggccgcggt agggccgcat cccgctccgg     60
agagaagtct gagtccgcca ggctctgcag gcccgcggaa gctcgacagc gtcatggcag    120
agcaggtggc cctgagccgg acccaggtgt gcgggatcct gcgggaagag cttttccagg    180
gcgatgcctt ccatcagtcg gatacacaca tattcatcat catgggtgca tcgggtgacc    240
tggccaagaa gaagatctac cccaccatct ggtggctgtt ccgggatggc cttctgcccg    300
aaaacacctt catcgtgggc tatgcccgtt cccgcctcac agtggctgac atccgcaaac    360
agagtgagcc cttcttcaag gccaccccag aggagaagct caagctggag gacttctttg    420
cccgcaactc ctatgtggct ggccagtacg atgatgcagc ctcctaccag cgcctcaaca    480
gccacatgaa tgccctccac ctggggtcac aggccaaccg cctcttctac ctggccttgc    540
ccccgaccgt ctacgaggcc gtcaccaaga acattcacga gtcctgcatg agccagatag    600
gctggaaccg catcatcgtg gagaagccct cgggaggga cctgcagagc tctgaccggc    660
tgtccaacca catctcctcc ctgttccgtg aggaccagat ctaccgcatc gaccactacc    720
tgggcaagga gatggtgcag aacctcatgg tgctgagatt tgccaacagg atcttcggcc    780
ccatctggaa ccgggacaac atcgcctgcg ttatcctcac cttcaaggag cccttttggca   840 ctgagggtcg cggggctat ttcgatgaat ttgggatcat ccgggacgtg atgcagaacc     900
acctactgca gatgctgtgt ctggtggcca tggagaagcc cgcctccacc aactcagatg    960
acgtccgtga tgagaaggtc aaggtgttga aatgcatctc agaggtgcag gccaacaatg    1020
```

| | |
|---|---|
| tggtcctggg ccagtacgtg gggaacccg atggagaggg cgaggccacc aaagggtacc | 1080 |
| tggacgaccc cacggtgccc cgcgggtcca ccaccgccac ttttgcagcc gtcgtcctct | 1140 |
| atgtggagaa tgagaggtgg gatggggtgc ccttcatcct gcgctgcggc aaggccctga | 1200 |
| acgagcgcaa ggccgaggtg aggctgcagt tccatgatgt ggccggcgac atcttccacc | 1260 |
| agcagtgcaa gcgcaacgag ctggtgatcc gcgtgcagcc caacgaggcc gtgtacacca | 1320 |
| agatgatgac caagaagccg ggcatgttct tcaaccccga ggagtcggag ctggacctga | 1380 |
| cctacggcaa cagatacaag aacgtgaagc tccctgacgc ctacgagcgc ctcatcctgg | 1440 |
| acgtcttctg cggagccag atgcacttcg tgcgcagcga cgagctccgt gaggcctggc | 1500 |
| gtattttcac cccactgctg caccagattg agctggagaa gcccaagccc atcccctata | 1560 |
| tttatggcag ccgaggcccc acggaggcag acgagctgat gaagagagtg ggtttccagt | 1620 |
| atgagggcac ctacaagtgg gtgaaccccc acaagctctg agccctgggc acccacctcc | 1680 |
| acccccgcca cggccaccct ccttcccgcc gcccgacccc gagtcgggag gactccggga | 1740 |
| ccattgacct cagctgcaca ttcctggccc cgggctctgg ccaccctggc ccgcccctcg | 1800 |
| ctgctgctac tacccgagcc cagctacatt cctcagctgc caagcactcg agaccatcct | 1860 |
| ggcccctcca gaccctgcct gagcccagga gctgagtcac ctcctccact cactccagcc | 1920 |
| caacagaagg aaggaggagg gcgcccattc gtctgtccca gagcttattg ccactgggt | 1980 |
| ctcactcctg agtgggccca gggtgggagg gagggacaag ggggaggaaa ggggcgagca | 2040 |
| cccacgtgag agaatctgcc tgtggccttg cccgccagcc tcagtgccac ttgacattcc | 2100 |
| ttgtcaccag caacatctcg agcccctgg atgtcccctg tcccaccaac tctgcactcc | 2160 |
| atggccaccc cgtgccaccc gtaggcagcc tctctgctat aagaaaagca gacgcagcag | 2220 |
| ctgggacccc tcccaacctc aatgccctgc cattaaatcc gcaaacagcc | 2270 |

<210> SEQ ID NO 47
<211> LENGTH: 98
<212> TYPE: DNA
<213> ORGANISM: Homo sapiens

<400> SEQUENCE: 47

| | |
|---|---|
| cagaccccac aggcgccttg actgaggaca gcatagacga caccttcctc ccagtgcctg | 60 |
| aatacataaa ccagtccgtt cccaaaaggc ccgctggc | 98 |

<210> SEQ ID NO 48
<211> LENGTH: 98
<212> TYPE: DNA
<213> ORGANISM: Homo sapiens

<400> SEQUENCE: 48

| | |
|---|---|
| cgctcctggc gctgctggct gcgctctgcc cggcgagtcg ggctctggag gaaaagaaag | 60 |
| gtaattatgt ggtgacagat cacggctcgt gcgtccga | 98 |

<210> SEQ ID NO 49
<211> LENGTH: 98
<212> TYPE: DNA
<213> ORGANISM: Homo sapiens

<400> SEQUENCE: 49

| | |
|---|---|
| cagaccccac aggcgccttg actgaggaca gcatagacga caccttcctc ccagtgcctg | 60 |
| aatacataaa ccagtccgtt cccaaaaggc ccgctggc | 98 |

```
<210> SEQ ID NO 50
<211> LENGTH: 98
<212> TYPE: DNA
<213> ORGANISM: Homo sapiens

<400> SEQUENCE: 50
cgctcctggc gctgctggct gcgctctgcc cggcgagtcg ggctctggag gaaaagaaag      60
gtaattatgt ggtgacagat cacggctcgt gcgtccga                              98

<210> SEQ ID NO 51
<211> LENGTH: 98
<212> TYPE: DNA
<213> ORGANISM: Homo sapiens

<400> SEQUENCE: 51
gccccgcgag cacagagcct cgcctttgcc gatccgccgc ccgtccacac ccgccgccag      60
ctcaccatgg atgatgatat cgccgcgctc gtcgtcga                             98
```

EGFR ASSAY

This application claims priority to U.S. provisional patent application Ser. No. 62/183,566, filed Jun. 23, 2015, which is incorporated herein by reference in its entirety.

FIELD

Provided herein is technology relating to treating cancer and particularly, but not exclusively, to methods and compositions for quantifying and/or detecting EGFR and/or EGFRvIII in biological samples.

BACKGROUND

The Epidermal Growth Factor Receptor (EGFR) gene is frequently amplified in a variety of cancer tumors. In some cancers, the resulting over-expression of EGFR mRNA and/or protein activates downstream signal transduction pathways, which contributes to cell cycle dysregulation and tumorigenesis. In addition to over-expressing wild-type EGFR (wtEGFR), some tumor cells also express a rearranged form of EGFR in which exons 2 through 7 are deleted, thereby juxtaposing exons 1 and 8. This mutant EGFR is known as EGFRde2-7 or EGFR mutant variant III (EGFRvIII). The EGFRvIII protein product induces ligand-independent cell signaling, which further increases the tumorigenic potential of cells expressing the mutation.

Anti-EGFR therapies are designed to target and destroy cancer cells that overexpress EGFR and/or express EGFRvIII. Thus, assessment of EGFR and/or EGFRvIII RNA expression profiles may serve as important diagnostic tools in the field of oncology.

SUMMARY

Provided herein is a technology for single-well detection of RNA (e.g., EGFRvIII RNA, EGFR RNA, and/or an endogenous control RNA such as beta-actin (ACTB) RNA, abelson tyrosine kinase (ABL) RNA, and/or glucose-6-phosphate (G6PD) RNA) and/or for single-well detection of a cDNA (e.g., a cDNA produced from an EGFRvIII RNA, an EGFR RNA, and/or from an endogenous control RNA such as ACTB RNA, ABL RNA, and/or G6PD RNA). For example, some embodiments of the technology are related to a diagnostic method and assay format that provide specific and sensitive detection of EGFRvIII and quantification of total EGFR mRNA expression using real-time RT-PCR technology (e.g., producing an EGFRvIII cDNA and/or an EGFR cDNA by reverse transcription, then amplifying the cDNA). In some embodiments, the technology provides a single-well multiplex RT-PCR for the detection of EGFRvIII expression (e.g., detection of EGFRvIII mRNA and/or cDNA), quantification of EGFR expression (e.g., quantification of total EGFR mRNA and/or cDNA, e.g., quantification of wild-type EGFR mRNA and/or cDNA and EGFRvIII mRNA and/or cDNA), and/or detection and/or quantification of the expression of an endogenous control such as ACTB, ABL, and/or G6PD (e.g., detection and/or quantification of ACTB, ABL, and/or G6PD mRNA and/or cDNA). Accordingly, the technology provides in some embodiments a diagnostic and/or prognostic tool for oncology and related fields.

Embodiments of the technology include an assay format that detects mRNA from an endogenous control (e.g., a housekeeping gene such as beta-actin), which is used to facilitate the quantification of EGFRvIII expression and total EGFR expression; and/or to provide a sample validity control for cell adequacy, sample extraction, and/or amplification efficiency. In some embodiments, the technology provides novel primers and probes specific for EGFRvIII and total EGFR. For example, in some embodiments, the technology described herein provides: 1) a novel design for an oligonucleotide primer set that directs reverse transcription and amplification of EGFRvIII RNA; 2) a novel design for an oligonucleotide primer set that directs reverse transcription and amplification of total EGFR RNA (e.g., both non-rearranged wild type EGFR and EGFRvIII mutant); 3) a novel design for a labeled oligonucleotide probe to detect EGFRvIII RNA; 4) a novel design for a labeled oligonucleotide probe to detect total EGFR RNA (both non-rearranged wild type EGFR and EGFRvIII mutant); and 5) a novel primer/probe set for amplifying and detecting RNA sequences from an endogenous control (e.g., a house-keeping gene such as ACTB, ABL, and/or G6PD).

The EGFR primers and probe target the exon 29/30 junction, which is present in both wild-type EGFR mRNA and in the EGFRvIII variant mRNA (e.g., to target total EGFR mRNA, e.g., to quantify and/or to detect total EGFR mRNA). The EGFRvIII primers and probe target the exon 1/8 junction (e.g., a target that is specific for EGFRvIII mRNA). Both primer/probe sets are designed to target exon junctions to detect RNA and/or cDNA, without detecting genomic DNA. Each amplicon is less than 90 nt (e.g., to provide a technology that is appropriate for application to formalin-fixed paraffin-embedded (FFPE) samples).

Accordingly, provided herein are embodiments of a technology related to a composition for detecting EGFRvIII mRNA. In particular embodiments, the composition comprises a primer comprising a sequence according to SEQ ID NO: 1 or SEQ ID NO: 31 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 1 or SEQ ID NO: 31 or that is 100% identical to SEQ ID NO: 1 or SEQ ID NO: 31) and a primer comprising a sequence according to SEQ ID NO: 2 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 2 or that is 100% identical to SEQ ID NO: 2). In some embodiments, the composition for detecting EGFRvIII mRNA further comprises a detectably labeled probe comprising a sequence according to SEQ ID NO: 3 (e.g., a probe comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 3 or that is 100% identical to SEQ ID NO: 3).

Additional embodiments provide a composition for detecting and/or quantifying total EGFR mRNA. In particular embodiments, the composition comprises a primer comprising a sequence according to SEQ ID NO: 7 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 7 or that is 100% identical to SEQ ID NO: 7) and a primer comprising a sequence according to SEQ ID NO: 8 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 8 or that is 100% identical to SEQ ID NO: 8). In some embodiments, the composition for detecting and/or quantifying total EGFR mRNA further comprises a detectably labeled probe comprising a sequence according to SEQ ID NO: 9 or SEQ ID NO: 32 (e.g., a probe comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 9 or SEQ ID NO: 32 or that is 100% identical to SEQ ID NO: 9 or SEQ ID NO: 32).

Additional embodiments provide a composition for detecting and/or quantifying ACTB mRNA. In particular embodiments, the composition comprises a primer comprising a sequence according to SEQ ID NO: 13 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 13 or that is 100% identical to SEQ ID NO: 13) and a primer comprising a sequence according to SEQ ID NO: 14 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 14 or that is 100% identical to SEQ ID NO: 14). In some embodiments, the composition for detecting and/or quantifying ACTB mRNA further comprises a detectably labeled probe comprising a sequence according to SEQ ID NO: 15 (e.g., a probe comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 15 or that is 100% identical to SEQ ID NO: 15).

Some embodiments provide a composition for detecting EGFRvIII mRNA and for quantifying total EGFR mRNA (e.g., in a multiplex, single-tube reaction). In particular embodiments, the composition comprises a primer comprising a sequence according to SEQ ID NO: 1 or SEQ ID NO: 31 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 1 or SEQ ID NO: 31 or that is 100% identical to SEQ ID NO: 1 or SEQ ID NO: 31), a primer comprising a sequence according to SEQ ID NO: 2 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 2 or that is 100% identical to SEQ ID NO: 2), a primer comprising a sequence according to SEQ ID NO: 7 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 7 or that is 100% identical to SEQ ID NO: 7), and a primer comprising a sequence according to SEQ ID NO: 8 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 8 or that is 100% identical to SEQ ID NO: 8). In some embodiments of the composition for detecting EGFRvIII mRNA and for quantifying total EGFR mRNA, the composition further comprises a detectably labeled probe comprising a sequence according to SEQ ID NO: 3 (e.g., a probe comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 3 or that is 100% identical to SEQ ID NO: 3) and a detectably labeled probe comprising a sequence according to SEQ ID NO: 9 or SEQ ID NO: 32 (e.g., a probe comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 9 or SEQ ID NO: 32 or that is 100% identical to SEQ ID NO: 9 or SEQ ID NO: 32). And, in some embodiments of the composition for detecting EGFRvIII mRNA and for quantifying total EGFR mRNA, the composition further comprises primers and probes for quantifying and/or detecting a control mRNA such as ACTB. For example, some embodiments provide a composition for detecting EGFRvIII mRNA and for quantifying total EGFR mRNA comprising a primer comprising a sequence according to SEQ ID NO: 13 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 13 or that is 100% identical to SEQ ID NO: 13), a primer comprising a sequence according to SEQ ID NO: 14 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 14 or that is 100% identical to SEQ ID NO: 14), and a detectably labeled probe comprising a sequence according to SEQ ID NO: 15 (e.g., a probe comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 15 or that is 100% identical to SEQ ID NO: 15).

Particular embodiments related to multiplex detection provide a composition wherein the detectably labeled probe comprising a sequence according to SEQ ID NO: 3 (e.g., a probe comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 3 or that is 100% identical to SEQ ID NO: 3) comprises a first distinguishable fluorescent moiety, the detectably labeled probe comprising a sequence according to SEQ ID NO: 9 or SEQ ID NO: 32 (e.g., a probe comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 9 or SEQ ID NO: 32 or that is 100% identical to SEQ ID NO: 9 or SEQ ID NO: 32) comprises a second distinguishable fluorescent moiety, and the detectably labeled probe comprising a sequence according to SEQ ID NO: 15 (e.g., a probe comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 15 or that is 100% identical to SEQ ID NO: 15) comprises a third distinguishable fluorescent moiety, e.g., to detect each probe separately by monitoring a separate detection channel in a real-time PCR.

Some embodiments relate to detecting EGFRvIII mRNA and quantifying total EGFR mRNA in a sample obtained from a subject, e.g., as a cancer diagnostic. Thus, in some embodiments, compositions further comprise a nucleic acid (e.g., RNA or DNA (e.g., cDNA)) prepared from a sample obtained from a subject.

Some embodiments provide a composition comprising a primer consisting of a sequence or a reverse complement of a sequence according to SEQ ID NO: 1 or SEQ ID NO: 31 and a primer consisting of a sequence or a reverse complement of a sequence according to SEQ ID NO: 2. In some embodiments, the composition for detecting EGFRvIII mRNA further comprises a detectably labeled probe consisting of a sequence or a reverse complement of a sequence according to SEQ ID NO: 3.

Additional embodiments provide a composition for detecting and/or quantifying total EGFR mRNA. In particular embodiments, the composition comprises a primer consisting of a sequence or a reverse complement of a sequence according to SEQ ID NO: 7 and a primer consisting of a sequence or a reverse complement of a sequence according to SEQ ID NO: 8. In some embodiments, the composition for detecting and/or quantifying total EGFR mRNA further comprises a detectably labeled probe consisting of a sequence or a reverse complement of a sequence according to SEQ ID NO: 9 or SEQ ID NO: 32.

Additional embodiments provide a composition for detecting and/or quantifying ACTB mRNA. In particular embodiments, the composition comprises a primer consisting of a sequence or a reverse complement of a sequence according to SEQ ID NO: 13 and a primer consisting of a sequence or a reverse complement of a sequence according to SEQ ID NO: 14. In some embodiments, the composition for detecting and/or quantifying ACTB mRNA further comprises a detectably labeled probe consisting of a sequence or a reverse complement of a sequence according to SEQ ID NO: 15.

Some embodiments provide a composition for detecting EGFRvIII mRNA and for quantifying total EGFR mRNA (e.g., in a multiplex, single-tube reaction). In particular embodiments, the composition comprises a primer consisting of a sequence or a reverse complement of a sequence according to SEQ ID NO: 1 or SEQ ID NO: 31, a primer consisting of a sequence or a reverse complement of a sequence according to SEQ ID NO: 2, a primer consisting of a sequence or a reverse complement of a sequence according to SEQ ID NO: 7, and a primer consisting of a sequence or a reverse complement of a sequence according to SEQ ID NO: 8. In embodiments of the composition for detecting EGFRvIII mRNA and for quantifying total EGFR mRNA, the composition further comprises a detectably labeled probe consisting of a sequence or a reverse complement of a sequence according to SEQ ID NO: 3 and a detectably labeled probe consisting of a sequence or a reverse complement of a sequence according to SEQ ID NO: 9 or SEQ ID NO: 32. And, in some embodiments of the composition for detecting EGFRvIII mRNA and for quantifying total EGFR mRNA, the composition further comprises primers and probes for quantifying and/or detecting a control mRNA such as ACTB. For example, some embodiments provide a composition for detecting EGFRvIII mRNA and for quantifying total EGFR mRNA comprising a primer consisting of a sequence or a reverse complement of a sequence according to SEQ ID NO: 13, a primer consisting of a sequence or a reverse complement of a sequence according to SEQ ID NO: 14, and a detectably labeled probe consisting of a sequence or a reverse complement of a sequence according to SEQ ID NO: 15.

Particular embodiments related to multiplex detection provide a composition wherein the detectably labeled probe consisting of a sequence or a reverse complement of a sequence according to SEQ ID NO: 3 comprises a first distinguishable fluorescent moiety, the detectably labeled probe consisting of a sequence or a reverse complement of a sequence according to SEQ ID NO: 9 or SEQ ID NO: 32 comprises a second distinguishable fluorescent moiety, and the detectably labeled probe consisting of a sequence or a reverse complement of a sequence according to SEQ ID NO: 15 comprises a third distinguishable fluorescent moiety, e.g., to detect each probe separately by monitoring a separate detection channel in a real-time PCR.

Some embodiments relate to detecting EGFRvIII mRNA and quantifying total EGFR mRNA in a sample obtained from a subject, e.g., as a cancer diagnostic. Thus, in some embodiments, compositions further comprise a nucleic acid (e.g., RNA or DNA (e.g., cDNA)) prepared from a sample obtained from a subject.

Some embodiments are related to reaction mixtures for detecting and/or quantifying a nucleic acid (e.g., a RNA or DNA (e.g., cDNA)), e.g., an EGFRvIII nucleic acid ((e.g., an EGFRvIII RNA or DNA (e.g., cDNA)), an EGFR nucleic acid (e.g., an EGFR RNA or DNA (e.g., cDNA), or a control nucleic acid (e.g., an ACTB, ABL, or G6PD RNA or DNA (e.g., cDNA)).

Accordingly, provided herein are embodiments of a technology related to a reaction mixture for detecting EGFRvIII mRNA. In particular embodiments, the reaction mixture comprises a primer comprising a sequence according to SEQ ID NO: 1 or SEQ ID NO: 31 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 1 or SEQ ID NO: 31 or that is 100% identical to SEQ ID NO: 1 or SEQ ID NO: 31) and a primer comprising a sequence according to SEQ ID NO: 2 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 2 or that is 100% identical to SEQ ID NO: 2). In some embodiments, the reaction mixture for detecting EGFRvIII mRNA further comprises a detectably labeled probe comprising a sequence according to SEQ ID NO: 3 (e.g., a probe comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 3 or that is 100% identical to SEQ ID NO: 3).

Additional embodiments provide a reaction mixture for detecting and/or quantifying total EGFR mRNA. In particular embodiments, the reaction mixture comprises a primer comprising a sequence according to SEQ ID NO: 7 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 7 or that is 100% identical to SEQ ID NO: 7) and a primer comprising a sequence according to SEQ ID NO: 8 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 8 or that is 100% identical to SEQ ID NO: 8). In some embodiments, the reaction mixture for detecting and/or quantifying total EGFR mRNA further comprises a detectably labeled probe comprising a sequence according to SEQ ID NO: 9 or SEQ ID NO: 32 (e.g., a probe comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 9 or SEQ ID NO: 32 or that is 100% identical to SEQ ID NO: 9 or SEQ ID NO: 32).

Additional embodiments provide a reaction mixture for detecting and/or quantifying ACTB mRNA. In particular embodiments, the reaction mixture comprises a primer comprising a sequence according to SEQ ID NO: 13 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 13 or that is 100% identical to SEQ ID NO: 13) and a primer comprising a sequence according to SEQ ID NO: 14 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 14 or that is 100% identical to SEQ ID NO: 14). In some embodiments, the reaction mixture for detecting and/or quantifying ACTB mRNA further comprises a detectably labeled probe comprising a sequence according to SEQ ID NO: 15 (e.g., a probe comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 15 or that is 100% identical to SEQ ID NO: 15).

Some embodiments provide a reaction mixture for detecting EGFRvIII mRNA and for quantifying total EGFR mRNA (e.g., in a multiplex, single-tube reaction). In particular embodiments, the reaction mixture comprises a primer comprising a sequence according to SEQ ID NO: 1 or SEQ ID NO: 31 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 1 or SEQ ID NO: 31 or that is 100% identical to SEQ ID NO: 1 or SEQ ID NO: 31), a primer comprising a sequence according to SEQ ID NO: 2 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 2 or that is 100% identical to SEQ ID NO: 2), a primer comprising a sequence according to SEQ ID NO: 7 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 7 or that is 100% identical to SEQ ID NO: 7), and a primer comprising a sequence according to SEQ ID NO: 8 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 8 or that is 100% identical to SEQ ID NO: 8). In some embodiments of the reaction mixture for detecting EGFRvIII mRNA and for quantifying total EGFR mRNA, the reaction mixture further comprises a detectably labeled probe comprising a sequence according to SEQ ID NO: 3 (e.g., a probe comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 3 or that is 100% identical to SEQ ID NO: 3) and a detectably labeled probe comprising a sequence according to SEQ ID NO: 9 or SEQ ID NO: 32 (e.g., a probe comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 9 or SEQ ID NO: 32 or that is 100% identical to SEQ ID NO: 9 or SEQ ID NO: 32). And, in some embodiments of the reaction mixture for detecting EGFRvIII mRNA and for quantifying total EGFR mRNA, the reaction mixture further comprises primers and probes for quantifying and/or detecting a control mRNA such as ACTB. For example, some embodiments provide a reaction mixture for detecting EGFRvIII mRNA and for quantifying total EGFR mRNA comprising a primer comprising a sequence according to SEQ ID NO: 13 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 13 or that is 100% identical to SEQ ID NO: 13), a primer comprising a sequence according to SEQ ID NO: 14 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 14 or that is 100% identical to SEQ ID NO: 14), and a detectably labeled probe comprising a sequence according to SEQ ID NO: 15 (e.g., a probe comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 15 or that is 100% identical to SEQ ID NO: 15).

Particular embodiments related to multiplex detection provide a reaction mixture wherein the detectably labeled probe comprising a sequence according to SEQ ID NO: 3 (e.g., a probe comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 3 or that is 100% identical to SEQ ID NO: 3) comprises a first distinguishable fluorescent moiety, the detectably labeled probe comprising a sequence according to SEQ ID NO: 9 or SEQ ID NO: 32 (e.g., a probe comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 9 or SEQ ID NO: 32 or that is 100% identical to SEQ ID NO: 9 or SEQ ID NO: 32) comprises a second distinguishable fluorescent moiety, and the detectably labeled probe comprising a sequence according to SEQ ID NO: 15 (e.g., a probe comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 15 or that is 100% identical to SEQ ID NO: 15) comprises a third distinguishable fluorescent moiety, e.g., to detect each probe separately by monitoring a separate detection channel in a real-time PCR.

Some embodiments relate to detecting EGFRvIII mRNA and quantifying total EGFR mRNA in a sample obtained from a subject, e.g., as a cancer diagnostic. Thus, in some embodiments, reaction mixtures further comprise a nucleic acid (e.g., RNA or DNA (e.g., cDNA)) prepared from a sample obtained from a subject.

Further embodiments are related to reaction mixtures for detecting and/or quantifying a nucleic acid (e.g., a RNA or DNA (e.g., cDNA)), e.g., an EGFRvIII nucleic acid ((e.g., an EGFRvIII RNA or DNA (e.g., cDNA)), an EGFR nucleic acid (e.g., an EGFR RNA or DNA (e.g., cDNA), or a control nucleic acid (e.g., an ACTB, ABL, or G6PD RNA or DNA (e.g., cDNA)).

For example, in particular embodiments, the reaction mixture comprises a primer consisting of a sequence or a reverse complement of a sequence according to SEQ ID NO: 1 or SEQ ID NO: 31 and a primer consisting of a sequence or a reverse complement of a sequence according to SEQ ID NO: 2. In some embodiments, the reaction mixture for detecting EGFRvIII mRNA further comprises a detectably labeled probe consisting of a sequence or a reverse complement of a sequence according to SEQ ID NO: 3.

Additional embodiments provide a reaction mixture for detecting and/or quantifying total EGFR mRNA. In particular embodiments, the reaction mixture comprises a primer consisting of a sequence or a reverse complement of a sequence according to SEQ ID NO: 7 and a primer consisting of a sequence or a reverse complement of a sequence according to SEQ ID NO: 8. In some embodiments, the reaction mixture for detecting and/or quantifying total EGFR mRNA further comprises a detectably labeled probe consisting of a sequence or a reverse complement of a sequence according to SEQ ID NO: 9 or SEQ ID NO: 32.

Additional embodiments provide a reaction mixture for detecting and/or quantifying ACTB mRNA. In particular embodiments, the reaction mixture comprises a primer consisting of a sequence or a reverse complement of a sequence according to SEQ ID NO: 13 and a primer consisting of a sequence or a reverse complement of a sequence according to SEQ ID NO: 14. In some embodiments, the reaction mixture for detecting and/or quantifying ACTB mRNA further comprises a detectably labeled probe consisting of a sequence or a reverse complement of a sequence according to SEQ ID NO: 15.

Some embodiments provide a reaction mixture for detecting EGFRvIII mRNA and for quantifying total EGFR mRNA (e.g., in a multiplex, single-tube reaction). In particular embodiments, the reaction mixture comprises a primer consisting of a sequence or a reverse complement of a sequence according to SEQ ID NO: 1 or SEQ ID NO: 31, a primer consisting of a sequence or a reverse complement of a sequence according to SEQ ID NO: 2, a primer consisting of a sequence or a reverse complement of a sequence according to SEQ ID NO: 7, and a primer consisting of a sequence or a reverse complement of a sequence according to SEQ ID NO: 8. In some embodiments of the reaction mixture for detecting EGFRvIII mRNA and for quantifying total EGFR mRNA, the reaction mixture further comprises a detectably labeled probe consisting of a sequence or a reverse complement of a sequence according to SEQ ID NO: 3 and a detectably labeled probe consisting of a sequence or a reverse complement of a sequence according to SEQ ID NO: 9 or SEQ ID NO: 32. And, in some embodiments of the reaction mixture for detecting EGFRvIII mRNA and for quantifying total EGFR mRNA, the reaction mixture further comprises primers and probes for quantifying and/or detecting a control mRNA such as ACTB. For example, some embodiments provide a reaction mixture for detecting EGFRvIII mRNA and for quantifying total EGFR mRNA comprising a primer consisting of a sequence or a reverse complement of a sequence according to SEQ ID NO: 13, a primer consisting of a sequence or a reverse complement of a sequence according to SEQ ID NO: 14, and a detectably labeled probe consisting of a sequence or a reverse complement of a sequence according to SEQ ID NO: 15.

Particular embodiments related to multiplex detection provide a reaction mixture wherein the detectably labeled probe consisting of a sequence or a reverse complement of a sequence according to SEQ ID NO: 3 comprises a first distinguishable fluorescent moiety, the detectably labeled probe consisting of a sequence or a reverse complement of a sequence according to SEQ ID NO: 9 or SEQ ID NO: 32 comprises a second distinguishable fluorescent moiety, and the detectably labeled probe consisting of a sequence or a reverse complement of a sequence according to SEQ ID NO: 15 comprises a third distinguishable fluorescent moiety, e.g., to detect each probe separately by monitoring a separate detection channel in a real-time PCR.

Some embodiments relate to detecting EGFRvIII mRNA and quantifying total EGFR mRNA in a sample obtained from a subject, e.g., as a cancer diagnostic. Thus, in some embodiments, reaction mixtures further comprise a nucleic acid (e.g., RNA or DNA (e.g., cDNA)) prepared from a sample obtained from a subject.

Further embodiments provide a method for detecting EGFRvIII expression in a sample. In particular embodiments, the method comprises mixing a patient sample with a composition comprising a primer comprising a sequence according to SEQ ID NO: 1 or SEQ ID NO: 31 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 1 or SEQ ID NO: 31 or that is 100% identical to SEQ ID NO: 1 or SEQ ID NO: 31), a primer comprising a sequence according to SEQ ID NO: 2 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 2 or that is 100% identical to SEQ ID NO: 2), and a detectably labeled probe comprising a sequence according to SEQ ID NO: 3 (e.g., a probe comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 3 or that is 100% identical to SEQ ID NO: 3) to provide a RT-PCR reaction mixture; reverse transcribing EGFRvIII mRNA to provide an EGFRvIII cDNA; amplifying the EGFRvIII cDNA to provide an EGFRvIII amplicon; and detecting the EGFRvIII amplicon, wherein detecting the EGFRvIII amplicon indicates the presence of EGFRvIII expression in the sample.

In some embodiments, the technology provides a method for quantifying and/or detecting total EGFR expression in a sample. In particular embodiments, the method comprises mixing a patient sample with a composition comprising a primer comprising a sequence according to SEQ ID NO: 7 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 7 or that is 100% identical to SEQ ID NO: 7), a primer comprising a sequence according to SEQ ID NO: 8 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 8 or that is 100% identical to SEQ ID NO: 8), and a detectably labeled probe comprising a sequence according to SEQ ID NO: 9 or SEQ ID NO: 32 (e.g., a probe comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 9 or SEQ ID NO: 32 or that is 100% identical to SEQ ID NO: 9 or SEQ ID NO: 32) to provide a RT-PCR reaction mixture; reverse transcribing total EGFR mRNA to provide total EGFR cDNA; amplifying the total EGFR cDNA to provide a total EGFR amplicon; and detecting or quantifying the total EGFR amplicon, wherein detecting or quantifying the total EGFR amplicon quantifies and/or detects total EGFR expression in the sample.

In some embodiments, the reverse transcribing, amplifying, and detecting are performed using one or both of RT-PCR or real-time PCR. For example, in some embodiments the detecting comprises determination of a Ct value.

Further embodiments provide a method for detecting EGFRvIII expression in a sample relative to a control. For example, in some embodiments the method comprises mixing a patient sample with a composition comprising a primer comprising a sequence according to SEQ ID NO: 1 or SEQ ID NO: 31 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 1 or SEQ ID NO: 31 or that is 100% identical to SEQ ID NO: 1 or SEQ ID NO: 31), a primer comprising a sequence according to SEQ ID NO: 2 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 2 or that is 100% identical to SEQ ID NO: 2), a primer comprising a sequence according to SEQ ID NO: 13 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 13 or that is 100% identical to SEQ ID NO: 13), a primer comprising a sequence according to SEQ ID NO: 14 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 14 or that is 100% identical to SEQ ID NO: 14), a detectably labeled probe comprising a sequence according to SEQ ID NO: 3 (e.g., a probe comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 3 or that is 100% identical to SEQ ID NO: 3), and a detectably labeled probe comprising a sequence according to SEQ ID NO: 15 (e.g., a probe comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 15 or that is 100% identical to SEQ ID NO: 15) to provide a RT-PCR reaction mixture; reverse transcribing EGFRvIII mRNA to provide a EGFRvIII cDNA; reverse transcribing ACTB mRNA to provide an ACTB cDNA; amplifying the EGFRvIII cDNA to provide an EGFRvIII amplicon and an EGFRvIII Ct value; amplifying the ACTB cDNA to provide an ACTB amplicon and an ACTB Ct value; and comparing the EGFRvIII Ct value and the ACTB Ct value to provide a dCt value, wherein the dCt value indicates the presence or absence of EGFRvIII expression in the sample. In some embodiments, the comparing comprises subtracting one Ct value from the other Ct value.

Some embodiments provide a method for quantifying total EGFR expression in a sample relative to a control. For example, in some embodiments the method comprises mixing a patient sample with a composition comprising a primer comprising a sequence according to SEQ ID NO: 7 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 7 or that is 100% identical to SEQ ID NO: 7), a primer comprising a sequence according to SEQ ID NO: 8 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 8 or that is 100% identical to SEQ ID NO: 8), a primer comprising a sequence according to SEQ ID NO: 13 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 13 or that is 100% identical to SEQ ID NO: 13), a primer comprising a sequence according to SEQ ID NO: 14 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 14 or that is 100% identical to SEQ ID NO: 14), a detectably labeled probe comprising a sequence according to SEQ ID NO: 9 or SEQ ID NO: 32 (e.g., a probe comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 9 or SEQ ID NO: 32 or that is 100% identical to SEQ ID NO: 9 or SEQ ID NO: 32), and a detectably labeled probe comprising a sequence according to SEQ ID NO: 15 (e.g., a probe comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 15 or that is 100% identical to SEQ ID NO: 15) to provide a RT-PCR reaction mixture; reverse transcribing total EGFR mRNA to provide total EGFR cDNA; reverse transcribing ACTB mRNA to provide an ACTB cDNA; amplifying the total EGFR cDNA to provide a total EGFR amplicon and a total EGFR Ct value; amplifying the ACTB cDNA to provide an ACTB amplicon and an ACTB Ct value; and comparing the total EGFR Ct value and the ACTB Ct value to provide a dCt value, wherein the dCt value is used to quantify the total EGFR expression in the sample relative to a control. In some embodiments, the comparing comprises subtracting one Ct value from the other Ct value.

Related embodiments provide a method of treating a subject. In particular embodiments, the subject has or is at risk of having a cancer. Some embodiments provide a method comprising contacting a biological sample obtained from a subject with a primer comprising a sequence according to SEQ ID NO: 1 or SEQ ID NO: 31 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 1 or SEQ ID NO: 31 or that is 100% identical to SEQ ID NO: 1 or SEQ ID NO: 31), a primer comprising a sequence according to SEQ ID NO: 2 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 2 or that is 100% identical to SEQ ID NO: 2), and a detectably labeled probe comprising a sequence according to SEQ ID NO: 3 (e.g., a probe comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 3 or that is 100% identical to SEQ ID NO: 3); and/or a primer comprising a sequence according to SEQ ID NO: 7 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 7 or that is 100% identical to SEQ ID NO: 7), a primer comprising a sequence according to SEQ ID NO: 8 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 8 or that is 100% identical to SEQ ID NO: 8), and a detectably labeled probe comprising a sequence according to SEQ ID NO: 9 or SEQ ID NO: 32 (e.g., a probe comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 9 or SEQ ID NO: 32 or that is 100% identical to SEQ ID NO: 9 or SEQ ID NO: 32); detecting EGFRvIII expression and/or EGFR overexpression in a biological sample obtained from a subject; and administering an anti-EGFR therapeutic agent to the subject (e.g., an anti-EGFR therapeutic agent that is a monoclonal antibody such as, e.g., ABT-806 or ABT-414) (see, e.g., Gan et al., J Clin Oncol 31, 2013 (suppl; abstr 2520); NIH clinical trials identifier NCT01255657; Gan et al., J Clin Oncol 32:5s, 2014 (suppl; abstr 2021); NIH clinical trials identifier NCT01800695; Phillips et al., Mol Cancer Ther 2013; 12(11 Suppl):A250).

Further embodiments provide a method for detecting EGFRvIII expression in a sample. In particular embodiments, the method comprises mixing a patient sample with a composition comprising a primer consisting of a sequence or a reverse complement of a sequence according to SEQ ID NO: 1 or SEQ ID NO: 31, a primer consisting of a sequence or a reverse complement of a sequence according to SEQ ID NO: 2, and a detectably labeled probe consisting of a sequence or a reverse complement of a sequence according to SEQ ID NO: 3 to provide a RT-PCR reaction mixture; reverse transcribing EGFRvIII mRNA to provide an EGFRvIII cDNA; amplifying the EGFRvIII cDNA to provide an EGFRvIII amplicon; and detecting the EGFRvIII amplicon, wherein detecting the EGFRvIII amplicon indicates the presence of EGFRvIII expression in the sample.

In some embodiments, the technology provides a method for quantifying and/or detecting total EGFR expression in a sample. In particular embodiments, the method comprises mixing a patient sample with a composition comprising a primer consisting of a sequence or a reverse complement of a sequence according to SEQ ID NO: 7, a primer consisting of a sequence or a reverse complement of a sequence according to SEQ ID NO: 8, and a detectably labeled probe consisting of a sequence or a reverse complement of a sequence according to SEQ ID NO: 9 or SEQ ID NO: 32 to provide a RT-PCR reaction mixture; reverse transcribing total EGFR mRNA to provide total EGFR cDNA; amplifying the total EGFR cDNA to provide a total EGFR amplicon; and detecting or quantifying the total EGFR amplicon, wherein detecting or quantifying the total EGFR amplicon quantifies and/or detects total EGFR expression in the sample.

In some embodiments, the reverse transcribing, amplifying, and detecting are performed using one or both of RT-PCR or real-time PCR. For example, in some embodiments the detecting comprises determination of a Ct value.

Further embodiments provide a method for detecting EGFRvIII expression in a sample relative to a control. For example, in some embodiments the method comprises mixing a patient sample with a composition comprising a primer consisting of a sequence or a reverse complement of a sequence according to SEQ ID NO: 1 or SEQ ID NO: 31, a primer consisting of a sequence or a reverse complement of a sequence according to SEQ ID NO: 2, a primer consisting of a sequence or a reverse complement of a sequence according to SEQ ID NO: 13, a primer consisting of a sequence or a reverse complement of a sequence according to SEQ ID NO: 14, a detectably labeled probe consisting of a sequence or a reverse complement of a sequence according to SEQ ID NO: 3, and a detectably labeled probe consisting of a sequence or a reverse complement of a sequence according to SEQ ID NO: 15 to provide a RT-PCR reaction mixture; reverse transcribing EGFRvIII mRNA to provide an EGFRvIII cDNA; reverse transcribing ACTB mRNA to provide an ACTB cDNA; amplifying the EGFRvIII cDNA to provide an EGFRvIII amplicon and an EGFRvIII Ct value; amplifying the ACTB cDNA to provide an ACTB amplicon and an ACTB Ct value; and comparing the EGFRvIII Ct value and the ACTB Ct value to provide a dCt value, wherein the dCt value indicates the presence or absence of EGFRvIII expression in the sample. In some embodiments, the comparing comprises subtracting one Ct value from the other Ct value.

Some embodiments provide a method for quantifying total EGFR expression in a sample relative to a control. For example, in some embodiments the method comprises mixing a patient sample with a composition comprising a primer consisting of a sequence or a reverse complement of a sequence according to SEQ ID NO: 7, a primer consisting of a sequence or a reverse complement of a sequence according to SEQ ID NO: 8, a primer consisting of a sequence or a reverse complement of a sequence according to SEQ ID NO: 13, a primer consisting of a sequence or a reverse complement of a sequence according to SEQ ID NO: 14, a detectably labeled probe consisting of a sequence or a reverse complement of a sequence according to SEQ ID NO: 9 or SEQ ID NO: 32, and a detectably labeled probe consisting of a sequence or a reverse complement of a sequence according to SEQ ID NO: 15 to provide a RT-PCR reaction mixture; reverse transcribing total EGFR mRNA to provide total EGFR cDNA; reverse transcribing ACTB mRNA to provide an ACTB cDNA; amplifying the total EGFR cDNA to provide a total EGFR amplicon and a total EGFR Ct value; amplifying the ACTB cDNA to provide an ACTB amplicon and an ACTB Ct value; and comparing the total EGFR Ct value and the ACTB Ct value to provide a dCt value, wherein the dCt value is used to quantify the total EGFR expression in the sample relative to a control. In some embodiments, the comparing comprises subtracting one Ct value from the other Ct value.

Related embodiments provide a method of treating a subject. In particular embodiments, the subject has cancer or is at risk of having a cancer. Some embodiments provide a method comprising contacting a biological sample obtained from a subject with a primer consisting of a sequence or a reverse complement of a sequence according to SEQ ID NO: 1 or SEQ ID NO: 31, a primer consisting of a sequence or a reverse complement of a sequence according to SEQ ID NO: 2, and a detectably labeled probe consisting of a sequence or a reverse complement of a sequence according to SEQ ID NO: 3; and/or a primer consisting of a sequence or a reverse complement of a sequence according to SEQ ID NO: 7, a primer consisting of a sequence or a reverse complement of a sequence according to SEQ ID NO: 8, and a detectably labeled probe consisting of a sequence or a reverse complement of a sequence according to SEQ ID NO: 9 or SEQ ID NO: 32; detecting EGFRvIII expression and/or EGFR overexpression in a biological sample obtained from a subject; and administering an anti-EGFR therapeutic agent to the subject (e.g., an anti-EGFR therapeutic agent that is a monoclonal antibody such as, e.g., ABT-806 or ABT-414).

Further embodiments are related to having EGFRvIII expression tested in a sample by another (e.g., another person) according to the technology provided herein (e.g., a physician, nurse, or other health-care worker ordering, requesting, and/or instructing a laboratory worker or other person to test a sample for EGFRvIII expression). In particular embodiments, the method comprises having EGFRvIII expression tested in a sample by ordering, requesting, and/or instructing another to test a sample for EGFRvIII expression according to a method comprising mixing a patient sample with a composition comprising a primer comprising a sequence according to SEQ ID NO: 1 or SEQ ID NO: 31 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 1 or SEQ ID NO: 31 or that is 100% identical to SEQ ID NO: 1 or SEQ ID NO: 31), a primer comprising a sequence according to SEQ ID NO: 2 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 2 or that is 100% identical to SEQ ID NO: 2), and a detectably labeled probe comprising a sequence according to SEQ ID NO: 3 (e.g., a probe comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 3 or that is 100% identical to SEQ ID NO: 3) to provide a RT-PCR reaction mixture; reverse transcribing EGFRvIII mRNA to provide an EGFRvIII cDNA; amplifying the EGFRvIII cDNA to provide an EGFRvIII amplicon; and detecting the EGFRvIII amplicon, wherein detecting the EGFRvIII amplicon indicates the presence of EGFRvIII expression in the sample. In some embodiments, the methods comprise receiving a result indicating the presence of EGFRvIII expression in the sample In some embodiments, the technology relates to having total EGFR expression quantified in a sample by another according to the technology provided herein (e.g., a physician, nurse, or other health-care worker ordering, requesting, and/or instructing a laboratory worker or other person to quantify total EGFR expression in a sample). In particular embodiments, the method comprises having total EGFR expression quantified in a sample by ordering, requesting, and/or instructing another to quantify total EGFR expression in a sample by a method comprising mixing a patient sample with a composition comprising a primer comprising a sequence according to SEQ ID NO: 7 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 7 or that is 100% identical to SEQ ID NO: 7), a primer comprising a sequence according to SEQ ID NO: 8 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 8 or that is 100% identical to SEQ ID NO: 8), and a detectably labeled probe comprising a sequence according to SEQ ID NO: 9 or SEQ ID NO: 32 (e.g., a probe comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 9 or SEQ ID NO: 32 or that is 100% identical to SEQ ID NO: 9 or SEQ ID NO: 32) to provide a RT-PCR reaction mixture; reverse transcribing total EGFR mRNA to provide total EGFR cDNA; amplifying the total EGFR cDNA to provide a total EGFR amplicon; and detecting or quantifying the total EGFR amplicon, wherein detecting or quantifying the total EGFR amplicon quantifies and/or detects total EGFR expression in the sample. In some embodiments, the methods comprise receiving a result comprising the presences, absence, and/or quantity of total EGFR expression in the sample.

In some embodiments, the reverse transcribing, amplifying, and detecting are performed by another using one or both of RT-PCR or real-time PCR. For example, in some embodiments the detecting performed by another comprises determination of a Ct value. In some embodiments, the methods comprise receiving a Ct value (e.g., relating to the presence, absence, and/or quantity of EGFRvIII and/or total EGFR expression (e.g., relative to an internal control (e.g., ACTB, ABL, and/or G6PD))).

Further embodiments are related to having EGFRvIII expression tested in a sample by another and relating EGFRvIII expression to a control (e.g., a physician, nurse, or other health-care worker ordering, requesting, and/or instructing a laboratory worker or other person to test a sample for EGFRvIII expression relative to a control). For example, in some embodiments the method comprises having EGFRvIII expression tested in a sample relative to a control by ordering, requesting, and/or instructing another to test a sample for EGFRvIII expression relative to a control by a method comprising mixing a patient sample with a composition comprising a primer comprising a sequence according to SEQ ID NO: 1 or SEQ ID NO: 31 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 1 or SEQ ID NO: 31 or that is 100% identical to SEQ ID NO: 1 or SEQ ID NO: 31), a primer comprising a sequence according to SEQ ID NO: 2 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 2 or that is 100% identical to SEQ ID NO: 2), a primer comprising a sequence according to SEQ ID NO: 13 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 13 or that is 100% identical to SEQ ID NO: 13), a primer comprising a sequence according to SEQ ID NO: 14 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 14 or that is 100% identical to SEQ ID NO: 14), a detectably labeled probe comprising a sequence according to SEQ ID NO: 3 (e.g., a probe comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 3 or that is 100% identical to SEQ ID NO: 3), and a detectably labeled probe comprising a sequence according to SEQ ID NO: 15 (e.g., a probe comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 15 or that is 100% identical to SEQ ID NO: 15) to provide a RT-PCR reaction mixture; reverse transcribing EGFRvIII mRNA to provide a EGFRvIII cDNA; reverse transcribing ACTB mRNA to provide an ACTB cDNA; amplifying the EGFRvIII cDNA to provide an EGFRvIII amplicon and an EGFRvIII Ct value; amplifying the ACTB cDNA to provide an ACTB amplicon and an ACTB Ct value; and comparing the EGFRvIII Ct value and the ACTB Ct value to provide a dCt value, wherein the dCt value indicates the presence or absence of EGFRvIII expression in the sample. In some embodiments, the methods comprise receiving a result comprising the presence or absence of EGFRvIII expression in the sample (e.g., a dCt value indicating the presence or absence of EGFRvIII expression in the sample).

Some embodiments are related to having total EGFR expression quantified in a sample by another and relating total EGFR expression to a control, e.g., a physician, nurse, or other health-care worker ordering, requesting, and/or instructing a laboratory worker or other person to quantify total EGFR expression relative to a control. For example, in some embodiments the method comprises having total EGFR expression quantified in a sample relative to a control by ordering, requesting, and/or instructing another to quantify total EGFR expression in a sample relative to a control by a method comprising mixing a patient sample with a composition comprising a primer comprising a sequence according to SEQ ID NO: 7 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 7 or that is 100% identical to SEQ ID NO: 7), a primer comprising a sequence according to SEQ ID NO: 8 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 8 or that is 100% identical to SEQ ID NO: 8), a primer comprising a sequence according to SEQ ID NO: 13 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 13 or that is 100% identical to SEQ ID NO: 13), a primer comprising a sequence according to SEQ ID NO: 14 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 14 or that is 100% identical to SEQ ID NO: 14), a detectably labeled probe comprising a sequence according to SEQ ID NO: 9 or SEQ ID NO: 32 (e.g., a probe comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 9 or SEQ ID NO: 32 or that is 100% identical to SEQ ID NO: 9 or SEQ ID NO: 32), and a detectably labeled probe comprising a sequence according to SEQ ID NO: 15 (e.g., a probe comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 15 or that is 100% identical to SEQ ID NO: 15) to provide a RT-PCR reaction mixture; reverse transcribing total EGFR mRNA to provide total EGFR cDNA; reverse transcribing ACTB mRNA to provide an ACTB cDNA; amplifying the total EGFR cDNA to provide a total EGFR amplicon and a total EGFR Ct value; amplifying the ACTB cDNA to provide an ACTB amplicon and an ACTB Ct value; and comparing the total EGFR Ct value and the ACTB Ct value to provide a dCt value, wherein the dCt value is used to quantify the total EGFR expression in the sample relative to a control. In some embodiments, the methods comprise receiving a result comprising a value describing total EGFR expression in the sample (e.g., a dCt value used to quantify the total EGFR expression in the sample relative to a control).

Related embodiments provide a method of having a subject treated for a disease, e.g., a disease such as a cancer. For example, some embodiments relate to, e.g., a physician, nurse, or other health-care worker ordering, requesting, and/or instructing another to treat a subject for a disease based on the result of a test to detect EGFRvIII expression and/or to quantify total EGFR expression. In particular embodiments, the subject has cancer or has an increased risk of having a cancer. For instance, some embodiments are related to a method comprising contacting a biological sample obtained from a subject with a primer comprising a sequence according to SEQ ID NO: 1 or SEQ ID NO: 31 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 1 or SEQ ID NO: 31 or that is 100% identical to SEQ ID NO: 1 or SEQ ID NO: 31), a primer comprising a sequence according to SEQ ID NO: 2 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 2 or that is 100% identical to SEQ ID NO: 2), and a detectably labeled probe comprising a sequence according to SEQ ID NO: 3 (e.g., a probe comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 3 or that is 100% identical to SEQ ID NO: 3); and/or a primer comprising a sequence according to SEQ ID NO: 7 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 7 or that is 100% identical to SEQ ID NO: 7), a primer comprising a sequence according to SEQ ID NO: 8 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 8 or that is 100% identical to SEQ ID NO: 8), and a detectably labeled probe comprising a sequence according to SEQ ID NO: 9 or SEQ ID NO: 32 (e.g., a probe comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 9 or SEQ ID NO: 32 or that is 100% identical to SEQ ID NO: 9 or SEQ ID NO: 32); detecting EGFRvIII expression and/or EGFR overexpression in a biological sample obtained from a subject; and ordering, requesting, and/or instructing another to administer an anti-EGFR therapeutic agent to the subject (e.g., an anti-EGFR therapeutic agent that is a monoclonal antibody such as, e.g., ABT-806 or ABT-414).

Some embodiments provide a method of selectively treating a cancer, the method comprising selecting a subject for treatment with an anti-EGFR agent on the basis of the patient having EGFRvIII expression; and selectively administering the anti-EGFR agent to the subject. Embodiments of selectively treating a cancer comprise detecting the presence, absence, or quantity of EGFRvIII according to a method comprising mixing a patient sample with a composition comprising a primer comprising a sequence according to SEQ ID NO: 1 or SEQ ID NO: 31 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 1 or SEQ ID NO: 31 or that is 100% identical to SEQ ID NO: 1 or SEQ ID NO: 31), a primer comprising a sequence according to SEQ ID NO: 2 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 2 or that is 100% identical to SEQ ID NO: 2), and a detectably labeled probe comprising a sequence according to SEQ ID NO: 3 (e.g., a probe comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 3 or that is 100% identical to SEQ ID NO: 3) to provide a RT-PCR reaction mixture; reverse transcribing EGFRvIII mRNA to provide a EGFRvIII cDNA; amplifying the EGFRvIII cDNA to provide an EGFRvIII amplicon; and detecting the EGFRvIII amplicon, wherein detecting the EGFRvIII amplicon indicates the presence of EGFRvIII expression in the sample.

Some embodiments provide a method of selectively treating a cancer, the method comprising selecting a subject for treatment with an anti-EGFR agent on the basis of the patient having total EGFR overexpression; and selectively administering the anti-EGFR agent to the subject. Embodiments of selectively treating a cancer comprise detecting the presence, absence, or quantity of total EGFR overexpression according to a method comprising mixing a patient sample with a composition comprising a primer comprising a sequence according to SEQ ID NO: 7 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 7 or that is 100% identical to SEQ ID NO: 7), a primer comprising a sequence according to SEQ ID NO: 8 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 8 or that is 100% identical to SEQ ID NO: 8), and a detectably labeled probe comprising a sequence according to SEQ ID NO: 9 or SEQ ID NO: 32 (e.g., a probe comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 9 or SEQ ID NO: 32 or that is 100% identical to SEQ ID NO: 9 or SEQ ID NO: 32) to provide a RT-PCR reaction mixture; reverse transcribing total EGFR mRNA to provide total EGFR cDNA; amplifying the total EGFR cDNA to provide a total EGFR amplicon; and detecting or quantifying the total EGFR amplicon, wherein detecting or quantifying the total EGFR amplicon quantifies and/or detects total EGFR expression in the sample.

Further embodiments provide a method for detecting EGFRvIII expression in a sample and reporting an EGFRvIII expression result and/or recommending a treatment (e.g., an anti-EGFR treatment). In particular embodiments, the method comprises mixing a patient sample with a composition comprising a primer comprising a sequence according to SEQ ID NO: 1 or SEQ ID NO: 31 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 1 or SEQ ID NO: 31 or that is 100% identical to SEQ ID NO: 1 or SEQ ID NO: 31), a primer comprising a sequence according to SEQ ID NO: 2 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 2 or that is 100% identical to SEQ ID NO: 2), and a detectably labeled probe comprising a sequence according to SEQ ID NO: 3 (e.g., a probe comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 3 or that is 100% identical to SEQ ID NO: 3) to provide a RT-PCR reaction mixture; reverse transcribing EGFRvIII mRNA to provide an EGFRvIII cDNA; amplifying the EGFRvIII cDNA to provide an EGFRvIII amplicon; detecting the EGFRvIII amplicon, wherein detecting the EGFRvIII amplicon indicates the presence of EGFRvIII expression in the sample; and reporting the presence of EGFRvIII expression in the sample and/or recommending a treatment based on the presence of EGFRvIII in the sample.

In some embodiments, the technology provides a method for quantifying and/or detecting total EGFR expression in a sample and reporting a total EGFR expression result or quantity and/or recommending a treatment (e.g., an anti-EGFR treatment). In particular embodiments, the method comprises mixing a patient sample with a composition comprising a primer comprising a sequence according to SEQ ID NO: 7 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 7 or that is 100% identical to SEQ ID NO: 7), a primer comprising a sequence according to SEQ ID NO: 8 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 8 or that is 100% identical to SEQ ID NO: 8), and a detectably labeled probe comprising a sequence according to SEQ ID NO: 9 or SEQ ID NO: 32 (e.g., a probe comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 9 or SEQ ID NO: 32 or that is 100% identical to SEQ ID NO: 9 or SEQ ID NO: 32) to provide a RT-PCR reaction mixture; reverse transcribing total EGFR mRNA to provide total EGFR cDNA; amplifying the total EGFR cDNA to provide a total EGFR amplicon; detecting or quantifying the total EGFR amplicon, wherein detecting or quantifying the total EGFR amplicon quantifies and/or detects total EGFR expression in the sample; and reporting the presence or quantity of total EGFR expression in the sample and/or recommending a treatment based on the presence or quantity of total EGFR expression.

In some embodiments, the reverse transcribing, amplifying, and detecting are performed using one or both of RT-PCR or real-time PCR. For example, in some embodiments the detecting comprises determining a Ct value and reporting of a Ct value.

Further embodiments provide a method for detecting EGFRvIII expression in a sample relative to a control and reporting relative EGFRvIII expression in a sample or recommending a treatment (e.g., an anti-EGFR treatment). For example, in some embodiments the method comprises mixing a patient sample with a composition comprising a primer comprising a sequence according to SEQ ID NO: 1 or SEQ ID NO: 31 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 1 or SEQ ID NO: 31 or that is 100% identical to SEQ ID NO: 1 or SEQ ID NO: 31), a primer comprising a sequence according to SEQ ID NO: 2 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 2 or that is 100% identical to SEQ ID NO: 2), a primer comprising a sequence according to SEQ ID NO: 13 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 13 or that is 100% identical to SEQ ID NO: 13), a primer comprising a sequence according to SEQ ID NO: 14 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 14 or that is 100% identical to SEQ ID NO: 14), a detectably labeled probe comprising a sequence according to SEQ ID NO: 3 (e.g., a probe comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 3 or that is 100% identical to SEQ ID NO: 3), and a detectably labeled probe comprising a sequence according to SEQ ID NO: 15 (e.g., a probe comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 15 or that is 100% identical to SEQ ID NO: 15) to provide a RT-PCR reaction mixture; reverse transcribing EGFRvIII mRNA to provide an EGFRvIII cDNA; reverse transcribing ACTB mRNA to provide an ACTB cDNA; amplifying the EGFRvIII cDNA to provide an EGFRvIII amplicon and an EGFRvIII Ct value; amplifying the ACTB cDNA to provide an ACTB amplicon and an ACTB Ct value; comparing the EGFRvIII Ct value and the ACTB Ct value to provide a dCt value, wherein the dCt value indicates the presence or absence of EGFRvIII expression in the sample; and reporting the presence or absence of EGFRvIII expression in the sample or recommending a treatment based on the presence or absence of EGFRvIII expression in the sample.

Some embodiments provide a method for quantifying total EGFR expression in a sample relative to a control and reporting total EGFR expression relative to a control or recommending a treatment (e.g., an anti-EGFR treatment). For example, in some embodiments the method comprises mixing a patient sample with a composition comprising a primer comprising a sequence according to SEQ ID NO: 7 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 7 or that is 100% identical to SEQ ID NO: 7), a primer comprising a sequence according to SEQ ID NO: 8 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 8 or that is 100% identical to SEQ ID NO: 8), a primer comprising a sequence according to SEQ ID NO: 13 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 13 or that is 100% identical to SEQ ID NO: 13), a primer comprising a sequence according to SEQ ID NO: 14 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 14 or that is 100% identical to SEQ ID NO: 14), a detectably labeled probe comprising a sequence according to SEQ ID NO: 9 or SEQ ID NO: 32 (e.g., a probe comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 9 or SEQ ID NO: 32 or that is 100% identical to SEQ ID NO: 9 or SEQ ID NO: 32), and a detectably labeled probe comprising a sequence according to SEQ ID NO: 15 (e.g., a probe comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 15 or that is 100% identical to SEQ ID NO: 15) to provide a RT-PCR reaction mixture; reverse transcribing total EGFR mRNA to provide total EGFR cDNA; reverse transcribing ACTB mRNA to provide an ACTB cDNA; amplifying the total EGFR cDNA to provide a total EGFR amplicon and a total EGFR Ct value; amplifying the ACTB cDNA to provide an ACTB amplicon and an ACTB Ct value; comparing the total EGFR Ct value and the ACTB Ct value to provide a dCt value, wherein the dCt value is used to quantify the total EGFR expression in the sample relative to a control; and reporting the total EGFR expression in the sample relative to a control or recommending a treatment based on the total EGFR expression in the sample relative to a control.

Related embodiments provide a method of recommending a treatment for a subject based on results provided by an embodiment of a method provided herein. In particular embodiments, the subject has a cancer or is at risk of having a cancer. Some embodiments provide a method comprising contacting a biological sample obtained from a subject with a primer comprising a sequence according to SEQ ID NO: 1 or SEQ ID NO: 31 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 1 or SEQ ID NO: 31 or that is 100% identical to SEQ ID NO: 1 or SEQ ID NO: 31), a primer comprising a sequence according to SEQ ID NO: 2 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 2 or that is 100% identical to SEQ ID NO: 2), and a detectably labeled probe comprising a sequence according to SEQ ID NO: 3 (e.g., a probe comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 3 or that is 100% identical to SEQ ID NO: 3); and/or a primer comprising a sequence according to SEQ ID NO: 7 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 7 or that is 100% identical to SEQ ID NO: 7), a primer comprising a sequence according to SEQ ID NO: 8 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 8 or that is 100% identical to SEQ ID NO: 8), and a detectably labeled probe comprising a sequence according to SEQ ID NO: 9 or SEQ ID NO: 32 (e.g., a probe comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 9 or SEQ ID NO: 32 or that is 100% identical to SEQ ID NO: 9 or SEQ ID NO: 32); detecting EGFRvIII expression and/or EGFR overexpression in a biological sample obtained from a subject; and recommending a treatment comprising administering an anti-EGFR therapeutic agent to the subject (e.g., an anti-EGFR therapeutic agent that is a monoclonal antibody such as, e.g., ABT-806 or ABT-414).

Embodiments also relate to kits. In particular embodiments, a kit for detecting EGFRvIII expression and/or quantifying or detecting total EGFR expression comprises a primer comprising a sequence according to SEQ ID NO: 1 or SEQ ID NO: 31 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 1 or SEQ ID NO: 31 or that is 100% identical to SEQ ID NO: 1 or SEQ ID NO: 31) and a primer comprising a sequence according to SEQ ID NO: 2 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 2 or that is 100% identical to SEQ ID NO: 2); a detectably labeled probe comprising a sequence according to SEQ ID NO: 3 (e.g., a probe comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 3 or that is 100% identical to SEQ ID NO: 3); a primer comprising a sequence according to SEQ ID NO: 7 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 7 or that is 100% identical to SEQ ID NO: 7) and a primer comprising a sequence according to SEQ ID NO: 8 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 8 or that is 100% identical to SEQ ID NO: 8); and/or a detectably labeled probe comprising a sequence according to SEQ ID NO: 9 or SEQ ID NO: 32 (e.g., a probe comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 9 or SEQ ID NO: 32 or that is 100% identical to SEQ ID NO: 9 or SEQ ID NO: 32). Some embodiments of kits further comprise a primer comprising a sequence according to SEQ ID NO: 13 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 13 or that is 100% identical to SEQ ID NO: 13), a primer comprising a sequence according to SEQ ID NO: 14 (e.g., a primer comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 14 or that is 100% identical to SEQ ID NO: 14), and a detectably labeled probe comprising a sequence according to SEQ ID NO: 15 (e.g., a probe comprising a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 15 or that is 100% identical to SEQ ID NO: 15).

In additional embodiments of kits for detecting EGFRvIII expression and/or quantifying or detecting total EGFR expression, the kits comprise a primer consisting of a sequence or a reverse complement of a sequence according to SEQ ID NO: 1 or SEQ ID NO: 31 and a primer consisting of a sequence or a reverse complement of a sequence according to SEQ ID NO: 2; a detectably labeled probe consisting of a sequence or a reverse complement of a sequence according to SEQ ID NO: 3; a primer consisting of a sequence or a reverse complement of a sequence according to SEQ ID NO: 7 and a primer consisting of a sequence or a reverse complement of a sequence according to SEQ ID NO: 8; and/or a detectably labeled probe consisting of a sequence or a reverse complement of a sequence according to SEQ ID NO: 9 or SEQ ID NO: 32. Some embodiments of kits further comprise a primer consisting of a sequence or a reverse complement of a sequence according to SEQ ID NO: 13, a primer consisting of a sequence or a reverse complement of a sequence according to SEQ ID NO: 14, and a detectably labeled probe consisting of a sequence or a reverse complement of a sequence according to SEQ ID NO: 15.

In some embodiments, a computer-based analysis program is used to transform the raw data generated by the detection assay (e.g., data comprising an EGFRvIII Ct value, a total EGFR Ct value, a EGFRvIII dCt value, a total EGFR dCt value; e.g., data comprising an indication of the presence, absence, or the amount of EGFRvIII and/or the amount of total EGFR expression) into data of predictive value for a physician, clinician, or other. In addition, the present technology comprises in some embodiments the receiving, processing, and transmitting of information to and from laboratories conducting the assays, information providers, medical personnel, and subjects. For example, in some embodiments of the present technology, a sample is obtained from a subject and submitted to a profiling service (e.g., a clinical lab at a medical facility, genomic profiling business, etc.) to generate data and/or a result. The data may be transmitted and/or displayed by any suitable method. For example, in some embodiments, a profiling service generates a report that is transmitted over a network, printed, and/or displayed to the clinician on a computer monitor.

Additional embodiments will be apparent to persons skilled in the relevant art based on the teachings contained herein.

BRIEF DESCRIPTION OF THE DRAWINGS

These and other features, aspects, and advantages of the present technology will become better understood with regard to the following drawings:

FIG. 4 is a schematic drawing showing locations (e.g., binding site, sequence, and/or complementary sequence) of the beta-actin primer and probe sequences relative to a cDNA (e.g., produced from a beta actin mRNA). The cDNA sequence at the beta-actin exon 1/exon 2 junction is shown.

FIG. 7A is a plot showing relative total EGFR expression (e.g., dCt, e.g., "actin-EGFR") measured for reaction mixtures comprising the EGFRvIII primers EGvIIIi1_−58to−41 and EGvIII-A and the EGFRvIII probe EGvIIIi1_−39to−21pFAM. FIG. 7B is a plot comparing relative total EGFR expression (e.g., dCt, e.g., "actin-EGFR") measured for reaction mixtures comprising the EGFRvIII primers EGvIIIi1_−58to−41 and EGvIII-A and the EGFRvIII probe EGvIIIi1_−39to−21pFAM with the relative total EGFR expression (e.g., dCt, e.g., "actin-EGFR") measured for reaction mixtures comprising the EGFRvIII primers EGvIIIi1_−58to−41 and EGFRvIII Rev_D and the EGFRvIII probe EGvIIIi1_−39to−21pFAM.

FIG. 8A is a plot showing relative EGFRvIII expression (e.g., dCt, e.g., "actin-EGFRvIII") measured using the EGFRvIII primers EGvIIIi1_−58to−41 and EGvIII-A and the EGFRvIII probe EGvIIIi1_−39to−21pFAM. FIG. 8B is a plot comparing the relative EGFRvIII expression (e.g., dCt, e.g., "actin-EGFRvIII") measured using the EGFRvIII primers EGvIIIi1_−58to−41 and EGvIII-A and the EGFRvIII probe EGvIIIi1_−39to−21pFAM with the relative EGFRvIII expression (e.g., dCt, e.g., "actin-EGFR") measured using the EGFRvIII primers EGvIIIi1_−58to−41 and EGFRvIII Rev_D and the EGFRvIII probe EGvIIIi1_−39to−21pFAM.

FIG. 15 shows the sequence of the mRNA product transcribed from the *Homo sapiens* glucose-6-phosphate dehydrogenase (G6PD) gene. The locations where some embodiments of detection primers (arrows) (or their reverse complements) and probes (thick lines) (or their reverse complements) hybridize to the G6PD mRNA or to a cDNA transcribed from the mRNA are indicated. Primer and probe sequences are provided in Table 5. Exons are indicated along the right side of the sequence.

FIG. 16A shows the relationship between the measured total EGFR, EGFRvIII, and ACTB Ct values and the total EGFR, EGFRvIII, and ACTB concentrations; FIG. 16B shows the relationship between the measured total EGFR and EGFRvIII dCt values (relative to ACTB) and the total EGFR and EGFRvIII concentrations.

FIG. 17A shows the relationship between the measured total EGFR, EGFRvIII, and ABL Ct values and the total EGFR, EGFRvIII, and ABL concentrations; FIG. 17B shows the relationship between the measured total EGFR and EGFRvIII dCt values (relative to ABL) and the total EGFR and EGFRvIII concentrations.

FIG. 18A shows the relationship between the measured total EGFR, EGFRvIII, and G6PD Ct values and the total EGFR, EGFRvIII, and G6PD concentrations; FIG. 18B shows the relationship between the measured total EGFR and EGFRvIII dCt values (relative to G6PD) and the total EGFR and EGFRvIII concentrations.

FIG. 19A shows the relationship between the measured total EGFR and ACTB Ct values and the total EGFR and ACTB concentrations; FIG. 19B shows the relationship between the measured total EGFR dCt values (relative to ACTB) and the total EGFR concentrations.

FIG. 20A shows the relationship between the measured total EGFR and ABL Ct values and the total EGFR and ABL concentrations; FIG. 20B shows the relationship between the measured total EGFR dCt values (relative to ABL) and the total EGFR concentrations.

FIG. 21A shows the relationship between the measured total EGFR and G6PD Ct values and the total EGFR and G6PD concentrations; FIG. 21B shows the relationship between the measured total EGFR dCt values (relative to G6PD) and the total EGFR concentrations.

Figure 1:
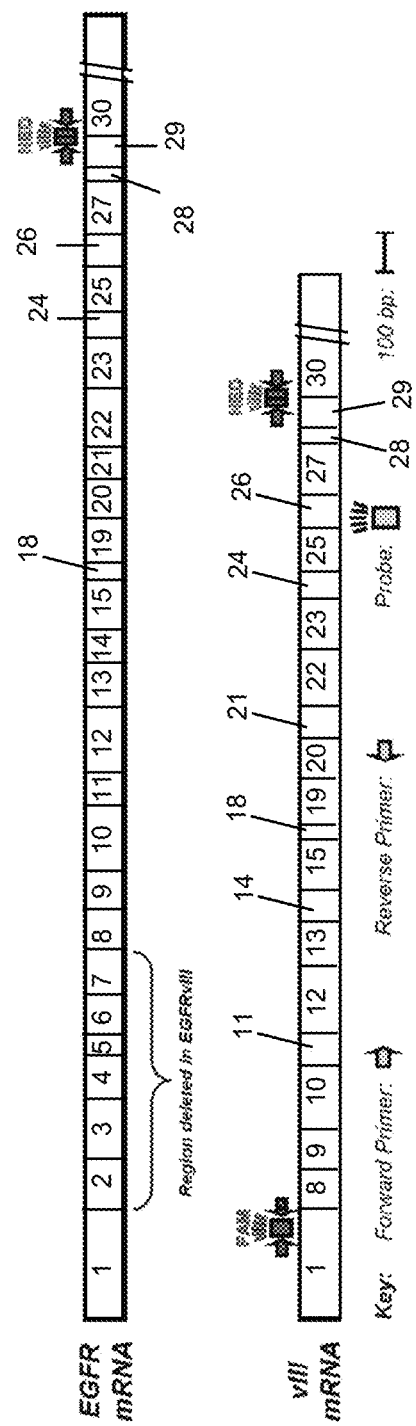
FIG. 1 is a schematic drawing showing primers and probes for detecting and/or quantifying total EGFR mRNA and EGFRvIII mRNA. The locations of primers and probes are indicated above the EGFR mRNA and the EGFRvIII mRNA. Exons within non-rearranged EGFR (wtEGFR) mRNA and EGFRvIII mRNA are depicted as numbered boxes. EGFR exons 2-7 (shaded grey, "Region deleted in EGFRvIII") are present in wtEGFR, but are deleted from the EGFRvIII mutant. Exon 1 and exons 8 through 30 are retained in both wtEGFR and EGFRvIII. As a result of the deletion, exons 1 and 8 are juxtaposed in EGFRvIII RNA.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DETAILED DESCRIPTION

Provided herein is technology relating to detecting cancer and particularly, but not exclusively, to methods and compositions for detecting and/or quantifying EGFR and/or EGFRvIII in biological samples. In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein. The section headings used herein are for organizational purposes only and are not to be construed as limiting the described subject matter in any way.

All literature and similar materials cited in this application, including but not limited to, patents, patent applications, articles, books, treatises, and internet web pages are expressly incorporated herein by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control.

DEFINITIONS

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

As used herein, a "nucleic acid" or "nucleic acid molecule" generally refers to any ribonucleic acid or deoxyribonucleic acid, which may be unmodified or modified DNA or RNA. "Nucleic acids" include, without limitation, single-stranded and double-stranded nucleic acids. As used herein, the term "nucleic acid" also includes DNA as described above that contains one or more modified bases. Thus, DNA with a backbone modified for stability or for other reasons is a "nucleic acid". The term "nucleic acid" as it is used herein embraces such chemically, enzymatically, or metabolically modified forms of nucleic acids, as well as the chemical forms of DNA characteristic of viruses and cells, including for example, simple and complex cells.

The terms "oligonucleotide" or "polynucleotide" or "nucleotide" or "nucleic acid" refer to a molecule having two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof. Typical deoxyribonucleotides for DNA are thymine, adenine, cytosine, and guanine. Typical ribonucleotides for RNA are uracil, adenine, cytosine, and guanine.

As used herein, the term "antibody" is used in its broadest sense to refer to whole antibodies, monoclonal antibodies (including human, humanized, or chimeric antibodies), polyclonal antibodies, and antibody fragments that can bind antigen (e.g., Fab', F'(ab)$_2$, Fv, single chain antibodies), comprising complementarity determining regions (CDRs) of the foregoing as long as they exhibit the desired biological activity.

As used herein, "antibody fragments" comprise a portion of an intact antibody, preferably the antigen binding or variable region of the intact antibody. Examples of antibody fragments include Fab, Fab', F(ab')2, and Fv fragments; diabodies; linear antibodies (Zapata et al., Protein Eng. 8(10): 1057-1062 (1995)); single-chain antibody molecules; and multispecific antibodies formed from antibody fragments.

An antibody that "specifically binds to" or is "specific for" a particular polypeptide or an epitope on a particular polypeptide is one that binds to that particular polypeptide or epitope on a particular polypeptide without substantially binding to any other polypeptide or polypeptide epitope.

As used herein, the terms "locus" or "region" of a nucleic acid refer to a subregion of a nucleic acid.

The terms "complementary" and "complementarity" refer to nucleotides (e.g., 1 or more nucleotide) or polynucleotides (e.g., a sequence of a plurality nucleotides) related by the base-pairing rules. For example, the sequence 5'-A-G-T-3' is complementary to the sequence 3'-T-C-A-5'. Complementarity may be "partial," in which only some of the nucleic acids' bases are matched according to the base pairing rules. Or, there may be "complete" or "total" complementarity between the nucleic acids. The degree of complementarity between nucleic acid strands effects the efficiency and strength of hybridization between nucleic acid strands. This is of particular importance in amplification reactions and in detection methods that depend upon binding between nucleic acids.

The term "gene" refers to a nucleic acid (e.g., DNA or RNA) sequence that comprises coding sequences necessary for the production of a RNA or of a polypeptide or its precursor. A functional polypeptide can be encoded by a full length coding sequence or by any portion of the coding sequence as long as the desired activity or functional properties (e.g., enzymatic activity, ligand binding, signal transduction, etc.) of the polypeptide are retained. The term "portion" when used in reference to a gene refers to fragments of that gene. The fragments may range in size from a few (e.g., 1 to 10, e.g., 1, 2, 3, 4, 5, 6, 7, 8, 9, 10) nucleotides to the entire gene sequence minus one nucleotide. Thus, "a nucleotide comprising at least a portion of a gene" may comprise fragments of the gene or the entire gene.

The term "gene" also encompasses the coding regions of a structural gene and includes sequences located adjacent to the coding region on both the 5' and 3' ends, e.g., for a distance of about 1 kb on either end, such that the gene corresponds to the length of the full-length mRNA (e.g., comprising coding, regulatory, structural and other sequences). The sequences that are located 5' of the coding region and that are present on the mRNA are referred to as 5' non-translated or untranslated sequences. The sequences that are located 3' or downstream of the coding region and that are present on the mRNA are referred to as 3' non-translated or 3' untranslated sequences. The term "gene" encompasses both cDNA and genomic forms of a gene. In some organisms (e.g., eukaryotes), a genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' ends of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, posttranscriptional cleavage, and polyadenylation.

The term "wild-type" when made in reference to a gene refers to a gene that has the characteristics of a gene isolated from a naturally occurring source. The term "wild-type" when made in reference to a gene product refers to a gene product that has the characteristics of a gene product isolated from a naturally occurring source. The term "naturally-occurring" as applied to an object refers to the fact that an object can be found in nature. For example, a polypeptide or polynucleotide sequence that is present in an organism (including viruses) that can be isolated from a source in nature and which has not been intentionally modified by the hand of a person in the laboratory is naturally-occurring. A wild-type gene is often that gene or allele that is most frequently observed in a population and is thus arbitrarily designated the "normal" or "wild-type" form of the gene (e.g., wild-type EGFR). In contrast, the term "modified" or "mutant" when made in reference to a gene or to a gene product refers, respectively, to a gene or to a gene product that displays modifications in sequence and/or functional properties (e.g., altered characteristics) when compared to the wild-type gene or gene product (e.g., EGFRvIII). It is noted that naturally-occurring mutants can be isolated; these are identified by the fact that they have altered characteristics when compared to the wild-type gene or gene product.

As used herein, "total EGFR" refers to EGFR mRNA in all forms and, in particular, "total EGFR" refers to all EGFR mRNA that comprises the exon 29/exon 30 junction, e.g., EGFR mRNA in both the "wild-type EGFR" ("wtEGFR") and EGFRvIII forms.

The term "allele" refers to a variation of a gene; the variations include but are not limited to variants and mutants, polymorphic loci, and single nucleotide polymorphic loci, frameshift, and splice mutations. An allele may occur naturally in a population or it might arise during the lifetime of any particular individual of the population.

Thus, the terms "variant" and "mutant" when used in reference to a nucleotide sequence refer to a nucleic acid sequence that differs by one or more nucleotides from another, usually related, nucleotide acid sequence. A "variation" is a difference between two different nucleotide sequences; typically, one sequence is a reference sequence.

"Amplification" is a special case of nucleic acid replication involving template specificity. It is to be contrasted with non-specific template replication (e.g., replication that is template-dependent but not dependent on a specific template). Template specificity is here distinguished from fidelity of replication (e.g., synthesis of the proper polynucleotide sequence) and nucleotide (ribonucleotide or deoxyribonucleotide) specificity. Template specificity is frequently described in terms of "target" specificity. Target sequences are "targets" in the sense that they are sought to be sorted out from other nucleic acids. Amplification techniques have been designed primarily for this sorting out.

Amplification of nucleic acids generally refers to the production of multiple copies of a polynucleotide, or a portion of the polynucleotide, typically starting from a small amount of the polynucleotide (e.g., a single polynucleotide molecule, 10 to 100 copies of a polynucleotide molecule, which may or may not be exactly the same), where the amplification products or amplicons are generally detectable. Amplification of polynucleotides encompasses a variety of chemical and enzymatic processes including polymerase chain reaction (PCR) and reverse transcription-polymerase chain reaction (RT-PCR).

The term "polymerase chain reaction" ("PCR") refers a method for increasing the concentration of a segment of a target sequence in a mixture of genomic DNA without cloning or purification. The length of the amplified segment of the desired target sequence is determined by the relative positions of the primers with respect to each other, and therefore, this length is a controllable parameter. Because the desired amplified segments of the target sequence become the predominant sequences (in terms of concentration) in the mixture, they are said to be "PCR amplified" and are "PCR products" or "amplicons."

As used herein, the term "RT-PCR reaction mixture" means a composition comprising elements appropriate to perform reverse transcription-polymerase chain reaction including but not limited to primers having specificity for the sequence of the diagnostic target RNA; a polymerase (e.g., a thermostable polymerase, e.g., heat activated thermostable polymerase); dNTPs, and appropriate buffers. In some embodiments, the polymerase comprises a reverse transcriptase activity. In some embodiments, the reverse transcriptase activity and polymerase activity are provided by two different enzymes.

As used herein, the term "RT reaction mixture" means a composition comprising elements appropriate to synthesize a DNA product from an RNA template, including but not limited to a reverse transcriptase enzyme, nucleic acid primer(s) complementary to the target RNA, dNTPs, and the appropriate buffers, and may further contain detection dyes or probes.

As used herein, the term "PCR reaction mixture" means a composition comprising elements appropriate to amplify a DNA template, including but not limited to nucleic acid primers, thermostable polymerases, dNTPs, and appropriate buffers, and may further contain detection dyes or probes.

The term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover or it may be due to the presence of nucleic acid contaminants sought to be purified away from the sample. For example, nucleic acids from organisms other than those to be detected may be present as background in a test sample.

The term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (e.g., in the presence of nucleotides and an inducing agent such as a DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer, and the use of the method. Within the context of reverse transcription, primers are composed of nucleic acids and prime on RNA templates. Within the context of PCR, primers are composed of nucleic acids and prime on DNA templates.

The term "probe" refers to an oligonucleotide (e.g., a sequence of nucleotides), whether occurring naturally as in a purified restriction digest or produced synthetically, recombinantly, or by PCR amplification, that is capable of hybridizing to another oligonucleotide of interest. A probe may be single-stranded or double-stranded. Probes are useful in the detection, identification, and isolation of particular gene sequences (e.g., a "capture probe"). It is contemplated that any probe used in the present invention may, in some embodiments, be "detectably labeled" or "labeled" with any "label" or "reporter moiety," so that it is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

The term "hybridization" is to be understood as the binding of an oligonucleotide to a complementary sequence in a nucleic acid by a number of Watson-Crick base pairings to form a duplex structure.

As used herein, the term "neoplasm" refers to "an abnormal mass of tissue, the growth of which exceeds and is uncoordinated with that of the normal tissues" See, e.g., Willis R A, "The Spread of Tumors in the Human Body", London, Butterworth & Co, 1952.

The term "pre-cancerous" or "pre-neoplastic" and equivalents thereof refer to any cellular proliferative disorder that is undergoing malignant transformation.

A "site" of a neoplasm, adenoma, cancer, etc. is the tissue, organ, cell type, anatomical area, body part, etc. in a subject's body where the neoplasm, adenoma, cancer, etc. is located.

As used herein, a "diagnostic" test application includes the detection or identification of a disease state or condition of a subject, determining the likelihood that a subject will contract a given disease or condition, determining the likelihood that a subject with a disease or condition will respond to therapy, determining the prognosis of a subject with a disease or condition (or its likely progression or regression), and determining the effect of a treatment on a subject with a disease or condition. For example, a diagnostic can be used for detecting the presence or likelihood of a subject contracting a neoplasm or the likelihood that such a subject will respond favorably to a compound (e.g., a pharmaceutical, e.g., a drug) or other treatment.

As used herein, the term "treating" includes reducing or alleviating at least one adverse effect or symptom of a disease or disorder. "Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

The term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids, such as DNA and RNA, are found in the state they exist in nature. Examples of non-isolated nucleic acids include: a given DNA sequence (e.g., a gene) found on the host cell chromosome in proximity to neighboring genes; RNA sequences, such as a specific mRNA sequence encoding a specific protein, found in the cell as a mixture with numerous other mRNAs which encode a multitude of proteins. However, isolated nucleic acid encoding a particular protein includes, by way of example, such nucleic acid in cells ordinarily expressing the protein, where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (i.e., the oligonucleotide may be single-stranded), but may contain both the sense and anti-sense strands (i.e., the oligonucleotide may be double-stranded). An isolated nucleic acid may, after isolation from its natural or typical environment, by be combined with other nucleic acids or molecules. For example, an isolated nucleic acid may be present in a host cell in which into which it has been placed, e.g., for heterologous expression.

The term "purified" refers to molecules, either nucleic acid or amino acid sequences that are removed from their natural environment, isolated, or separated. An "isolated nucleic acid sequence" may therefore be a purified nucleic acid sequence. "Substantially purified" molecules are at least 60% free, preferably at least 75% free, and more preferably at least 90% free from other components with which they are naturally associated. As used herein, the terms "purified" or "to purify" also refer to the removal of contaminants from a sample. The removal of contaminating proteins results in an increase in the percent of polypeptide or nucleic acid of interest in the sample. In another example, recombinant polypeptides are expressed in plant, bacterial, yeast, or mammalian host cells and the polypeptides are purified by the removal of host cell proteins; the percent of recombinant polypeptides is thereby increased in the sample.

The term "composition comprising" a given nucleotide sequence or polypeptide sequence refers broadly to any composition containing a nucleic acid having the given nucleotide sequence or a polypeptide having the given amino acid (e.g., polypeptide) sequence. The composition may comprise other components.

The term "sample" is used in its broadest sense. In one sense it can refer to an animal cell or tissue. In another sense, it is meant to include a specimen or culture obtained from any source, as well as biological and environmental samples. Biological samples may be obtained from plants or animals (including humans) and encompass fluids, solids, tissues, and gases. Materials obtained from clinical or forensic settings that contain nucleic acids are also within the intended meaning of the term "sample". Preferably, the sample is a biological sample derived from an animal, e.g., a human. The term "sample" also includes processed samples including preserved, fixed, and/or stabilized samples, such as formalin fixed and paraffin-embedded (FFPE samples) and other samples that were treated with cross-linking fixatives such as glutaraldehyde. These examples are not to be construed as limiting the sample types applicable to the present technology.

As used herein, the terms "patient" or "subject" refer to organisms to be subject to various tests provided by the technology. The term "subject" includes animals, preferably mammals, including humans. In a preferred embodiment, the subject is a primate. In an even more preferred embodiment, the subject is a human.

As used herein, the term "reverse transcription followed by polymerase chain reaction", or "RT-PCR", refers to a technique for synthesizing a cDNA from RNA and amplifying the cDNA molecule. RT-PCR is useful for detecting RNA species such as in quantitative analysis of gene expression and for producing DNA copies of RNA for use in cloning, cDNA library construction, probe synthesis, and signal amplification in in situ hybridizations. The technique comprises two parts: 1) synthesis of cDNA from RNA by reverse transcription (RT); and 2) amplification of a specific cDNA by polymerase chain reaction (PCR). Reverse transcriptase is an RNA dependent DNA polymerase that catalyzes the polymerization of nucleotides using template RNA or the RNA molecule in an RNA:DNA hybrid. Typically, both the reverse transcription and the PCR reactions of the RT-PCR reaction are performed in a single tube.

The term "multiplex amplification" as used herein means the simultaneous amplification of multiple DNA or RNA target sequences in a single mixture.

The term "multiplex RT-PCR" as used herein means reverse transcribing the multiple RNA molecules in a sample that contains a mixture of RNA and DNA molecules to produce a mixture that contains multiple cDNA and DNA molecules, and then simultaneously PCR amplifying particular target sequences from the multiple cDNA and DNA molecules in a single reaction mixture.

As used herein, the term "cycle threshold" or "Ct" refers to the threshold in RT-PCR at which the fluorescence generated within a reaction well exceeds an established threshold or cutoff (e.g., "baseline") level. The cycle threshold refers to the same value as do the terms "crossing point" (Cp) and "take-off point" (TOP) used by competing manufacturers of real-time PCR instruments for reasons of product differentiation, and the term "quantification cycle" (Cq) as proposed by the MIQE Guidelines (Bustin et al., Clinical Chemistry, 55:4, pp. 611-622 (2009)). As used herein, the term "dCt", "delta Ct", or "ΔCt" refers to the difference in two Ct values, e.g., the Ct value for a nucleic acid of interest subtracted from the Ct value for a control or the Ct value for a control subtracted from the Ct value for a nucleic acid of interest.

As used herein, the terms "reference", "reference gene", "reference marker", "reference target", "control", "control marker", "control target" refer to a reference molecule that controls and/or can be used to control for potential process interfering factors and/or provides one or more indications about the sample quality, the effective sample preparation, and/or assembly of the RT-PCR reaction in the sample. A control may either be co-detected or detected separately from targets.

As used herein, "gene expression" or "expression" refers to the absolute or relative levels of expression and/or pattern of expression of a gene. The expression of a gene may be measured at the level of DNA, cDNA, RNA, mRNA, or combinations thereof. Expression may be measured in a sample by various methods including but not limited to microarray technologies and quantitative and semi-quantitative RT-PCR techniques. Measures of expression may be qualitative or quantitative, e.g., expression can be absent, present, detectable, undetectable, below a detection threshold (or, alternatively, below a limit of detection (LOD)), above a detection threshold (or, alternatively, above a limit of detection (LOD)), a value of zero, a value less than zero, or a value more than zero.

As used herein, the word "presence" or "absence" (or, alternatively, "present or "absent") is used in a relative sense to describe the amount or level of a particular entity (e.g., a nucleic acid (e.g., an RNA (e.g., a mRNA))). For example, when a nucleic acid is said to be "present" in a test sample, it means the level or amount of this nucleic acid is above a pre-determined threshold; conversely, when a nucleic acid is said to be "absent" in a test sample, it means the level or amount of this nucleic acid is below a pre-determined threshold. The pre-determined threshold may be the threshold for detectability associated with the particular test used to detect the nucleic acid or any other threshold. When a nucleic acid is "detected" or "detectable" in a sample it is "present" in the sample; when a nucleic acid is "not detected" or "not detectable" it is "absent" from the sample. Further, a sample in which a nucleic acid is "detected" or "detectable" or in which the nucleic acid is "present" is a sample that is "positive" for the nucleic acid. A sample in which a nucleic acid is "not detected" or "not detectable" or in which the nucleic acid is "absent" is a sample that is "negative" for the nucleic acid.

In some embodiments, "detecting" a nucleic acid refers to determining if the nucleic acid is "present" or "absent"; in some embodiments, "detecting" further comprises "quantifying" the nucleic acid, e.g., measuring an amount of the nucleic acid.

As used herein, an "increase" or a "decrease" refers to a detectable (e.g., measured) positive or negative change in the value of a variable relative to a previously measured value of the variable, relative to a pre-established value (e.g., a previously known value, a published value, etc.), and/or relative to a value of a standard control. An increase is a positive change preferably at least 10%, more preferably 50%, still more preferably 2-fold, even more preferably at least 5-fold, and most preferably at least 10-fold relative to the previously measured value of the variable, the pre-established value, and/or the value of a standard control.

Similarly, a decrease is a negative change preferably at least 10%, more preferably 50%, still more preferably at least 80%, and most preferably at least 90% of the previously measured value of the variable, the pre-established value, and/or the value of a standard control. Other terms indicating quantitative changes or differences, such as "more" or "less," are used herein in the same fashion as described above.

As used herein, a "system" refers to a set of components, real or abstract, comprising a whole and in which each component interacts with or is related to at least one other component within the whole.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

Description

Although the disclosure herein refers to certain illustrated embodiments, it is to be understood that these embodiments are presented by way of example and not by way of limitation.

EGFRvIII Amplification Primers and Hybridization Probes

Figure 2A:
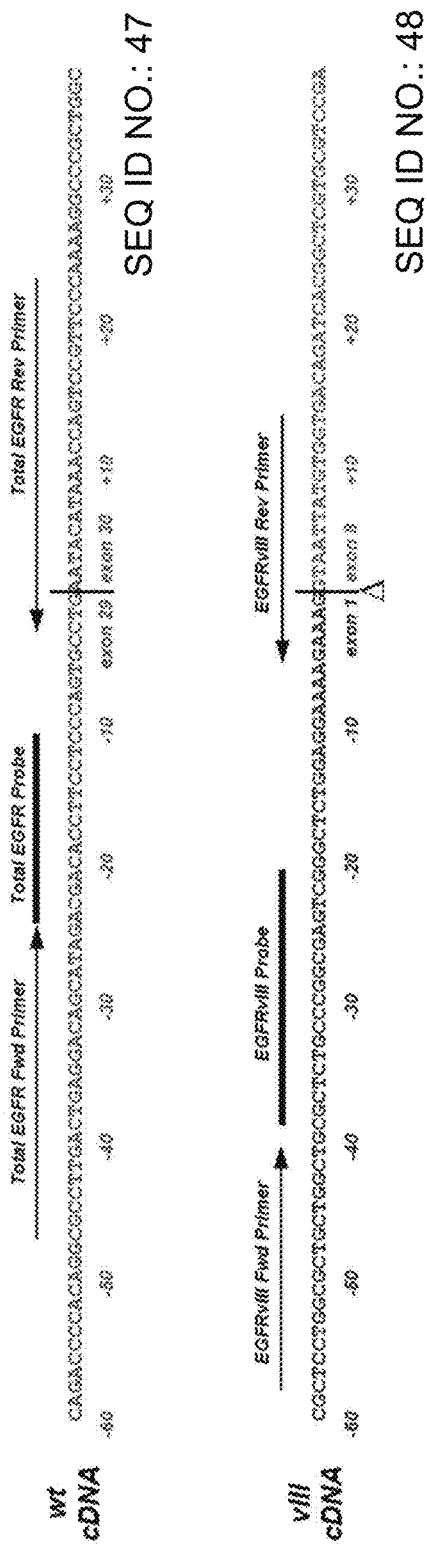
FIG. 2A is a schematic drawing showing embodiments of the total EGFR and EGFRvIII primer and probe sequences relative to the cDNA sequences reverse transcribed from the EGFR and EGFRvIII mRNAs. The cDNA sequence at the wild-type EGFR exon 29/30 junction is shown in the top portion of FIG. 2A ("wt") and the cDNA sequence at the EGFRvIII exon 1/8 junction is shown in the lower portion of FIG. 2A ("vIII"). The top schematic shows the locations (e.g., binding site, sequence, and/or complementary sequence) of the total EGFR forward primer (e.g., EGwti29_−47to−25), the total EGFR reverse primer (e.g., EGwti29_+23to−3), and the total EGFR probe (e.g., EGi29_−24to−11pFAM). The bottom schematic shows the locations (e.g., binding site, sequence, and/or complementary sequence) of the EGFRvIII forward primer (e.g., EGvIIIi1_−58to−41), the EGFRvIII reverse primer (e.g., EGFRvIII Rev_D), and the probe (e.g., EGvIIIi1_−39to−21pFAM).
Figure 2B:
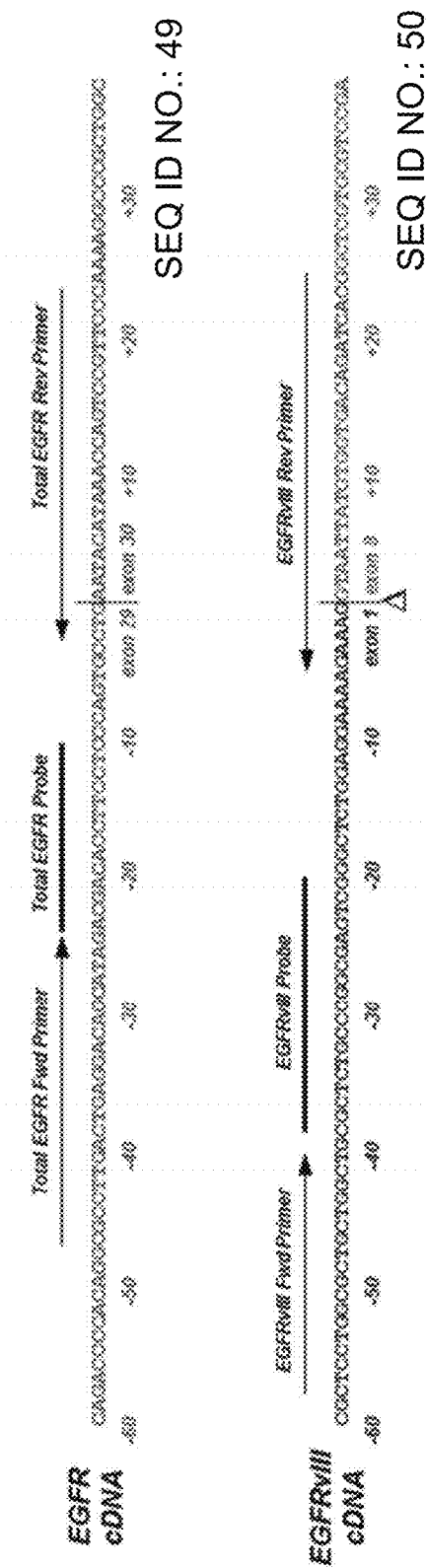
FIG. 2B is a schematic drawing showing embodiments of the total EGFR and EGFRvIII primer and probe sequences relative to the cDNA sequences reverse transcribed from the EGFR and EGFRvIII mRNAs. The cDNA sequence at the wild-type EGFR exon 29/30 junction is shown in the top portion of FIG. 2B ("EGFR") and the cDNA sequence at the EGFRvIII exon 1/8 junction is shown in the lower portion of FIG. 2B ("EGFRvIII"). The top schematic shows the locations (e.g., binding site, sequence, and/or complementary sequence) of the total EGFR forward primer (e.g., EGwti29_−47to−25), the total EGFR reverse primer (e.g., EGwti29_+23to−3), and the total EGFR probe (e.g., Total Probe (VIC)). See Table 13. The bottom schematic shows the locations (e.g., binding site, sequence, and/or complementary sequence) of the EGFRvIII forward primer (e.g., EGvIIIi1_−58to−41), the EGFRvIII reverse primer (e.g., EGFRvIII-A), and the probe (e.g., EGvIIIi1_−39to−21pFAM-BHQ1 dT). See Table 13.

In some embodiments, the technology provided herein relates to detection and/or quantification of EGFRvIII and/or total EGFR RNA expression. During the development of embodiments of the technology, two oligonucleotide primers ("RPvIII" and "FPvIII") and one hybridization probe ("PBvIII") were developed that target EGFRvIII RNA. Exemplary primer and probe sequences contemplated for use in the technology are provided in TABLE 1 and TABLE 5; see, e.g., FIG. 1 and FIG. 2. As used herein, the terms "FPvIII", "RPvIII", and "PBvIII" refer to forward primers, reverse primers, and hybridization probes targeting EGFRvIII RNA or EGFRvIII cDNA as described herein and as exemplified by the specific primers and probes contemplated and described.

These primers and probe find use in the specific amplification (e.g., by RT-PCR) and detection of EGFRvIII RNA (e.g., the primers and probe amplify and detect EGFRvIII RNA and the primers and probe do not amplify and detect wild-type EGFR RNA). In particular, the reverse primer RPvIII anneals to a specific sequence spanning the fusion junction of EGFR exon 1 and EGFR exon 8 that is present in EGFRvIII but that is not present in wild-type (e.g., non-rearranged) EGFR (see, e.g., FIG. 1). Since the EGFR exon 1/exon 8 junction sequence is specific to EGFRvIII RNA, this design provides that the cDNA generated during amplification by the extension of reverse primer RPvIII is specifically produced from EGFRvIII RNA and is not produced from wild-type (non-rearranged) EGFR RNA or from genomic DNA. Amplification (e.g., by PCR) of the resulting EGFRvIII cDNA is directed by the reverse primer RPvIII in combination with forward primer FPvIII, which is specific to EGFR exon 1 (see, e.g., FIG. 1 and FIG. 2). The fluorescently labeled probe (PBvIII) targets EGFR exon 1 sequences between the forward primer FPvIII and reverse primer RPvIII and thus provides for the detection of the EGFRvIII-specific amplification product (e.g., by real-time PCR).

TABLE 1

EGFRvIII oligonucleotides

| name | description | target site | sequence (5' to 3') | SEQ ID NO |
|------|-------------|-------------|---------------------|-----------|
| RPvIII | EGFRvIII reverse primer | fusion junction of EGFR exon 1 and EGFR exon 8 | ACCACATAAT TACcttttc | 1 |
| RPvIII | EGFRvIII reverse primer | fusion junction of EGFR exon 1 and EGFR exon 8 | CGTGATCTGT CACCACATAA TTACctttc | 31 |
| FPvIII | EGFRvIII forward primer | EGFR exon 1 | CTCCTGGCGC TGCTGGCT | 2 |
| PBvIII | EGFRvIII probe | EGFR exon 1 | D-CGCTCTGC CCGGCGAGTC G-Q | 3 |

In TABLE 1, upper case letters in the reverse primer sequence RPvIII (e.g., ACCACATAATTAC (SEQ ID NO: 4)) indicate the bases of the primer that hybridize to the 5' end of EGFR exon 8 and lower case letters in the reverse primer sequence RPvIII (e.g., ctttc (SEQ ID NO: 5)) indicate the bases of the primer that hybridize to the 3' end of EGFR exon 1. Further, the probe sequence provided in TABLE 1 is derived from the sense strand of the EGFR gene, but the technology also encompasses use of a probe having a sequence that is complementary to the sequence of PBvIII provided in TABLE 1 (e.g., CGACTCGCCGGGCA-GAGCG (SEQ ID NO: 6)). Embodiments provide that the dye D is any moiety (e.g., a dye) that can fluoresce and allow effective association of the probe to the target. Embodiments provide that the quencher Q in probe PBvIII at the opposite end from the dye D in probe PBvIII is any moiety that effectively quenches the fluorescent dye and allows effective association (e.g., hybridization) of these probes to their target sequences. In TABLE 1, the dye D is attached to PBvIII at the 5' end of PBvIII and the quencher Q is attached to PBvIII at the 3' end of PBvIII; however, the technology also includes a probe in which the dye D is attached to the probe at the 3' end of the probe and the quencher Q is attached to the probe at the 5' end of the probe. The probe in TABLE 1 does not limit the technology. For instance, the technology also provides embodiments in which a probe comprises a detectable label at the 5' end and/or at the 3' end, e.g., a probe that comprises a dye D at the 5' end or at the 3' end. Some embodiments provide a probe that does not comprise a quencher. In some embodiments, the primers and/or the probe are modified, e.g., to include a variety of binding enhancers such as a minor groove binder ("MGB") or a pdU or pdC nucleotide.

Total EGFR Amplification Primers and Hybridization Probes

In some embodiments, the technology relates to the amplification and detection of total EGFR RNA and/or the detection and/or quantification of total EGFR expression (e.g., comprising both expression of non-rearranged wild type EGFR and expression of the EGFRvIII mutant). During the development of embodiments of the technology, two oligonucleotide primers ("RPtot" and "FPtot") and one hybridization probe ("PBtot") were developed that target total EGFR RNA. Exemplary primer and probe sequences contemplated for use in the technology are provided in TABLE 2; see, e.g., FIG. 1 and FIG. 2. As used herein, the terms "FPtot", "RPtot", and "PBtot" refer to forward primers, reverse primers, and hybridization probes targeting total EGFR RNA or total EGFR cDNA (e.g., comprising RNA and/or cDNA of both the non-rearranged wild type EGFR and the EGFRvIII mutant) as described herein and as exemplified by the specific primers and probes contemplated and described.

These primers and probe find use in the amplification (e.g., by RT-PCR) and detection of both EGFR RNA and EGFRvIII RNA. In particular, the reverse primer RPtot anneals to a specific sequence spanning the splice junction of EGFR exon 29 and EGFR exon 30 (see, e.g., FIG. 1 and FIG. 2). The EGFR exon 29/exon 30 junction sequence is present in RNAs encoded by both wild type EGFR (non-rearranged) and EGFRvIII (see, e.g., FIG. 1 and FIG. 2), but not in the genomic DNA. Therefore, reverse primer RPtot provides an amplification product (e.g., a cDNA) from wild-type EGFR RNA and EGFRvIII RNA, but does not provide an amplification product from wild-type EGFR genomic DNA or from EGFRvIII genomic DNA. Amplification (e.g., by PCR) of the resulting total EGFR cDNA (e.g., wild-type EGFR cDNA and EGFRvIII cDNA) is directed by reverse primer RPtot in combination with forward primer FPtot, which is specific to EGFR exon 29. The fluorescently labeled probe (PBtot) targets EGFR exon 29 sequences between the forward and reverse primers and thus provides for the detection of total EGFR amplification product (e.g., by real-time PCR), e.g., from both wild-type EGFR RNA and EGFRvIII RNA.

TABLE 2

Total EGFR oligonucleotides

| name | description | target site | sequence (5' to 3') | SEQ ID NO |
|---|---|---|---|---|
| RPtot | total EGFR reverse primer | splice junction of EGFR exon 29 and EGFR exon 30 | GGGAACGGAC TGGTTTATGT ATTcag | 7 |
| FPtot | total EGFR forward primer | EGFR exon 29 | CGCCTTGACT GAGGACAGCA TAG | 8 |
| PBtot | total EGFR probe | EGFR exon 29 | D-ACGACACC TTCCTC-Q | 9 |
| PBtot | total EGFR probe | EGFR exon 29 | D-A7A C76 67C 67C 7AG 6G-Q | 32 |

In TABLE 2, upper case letters in the reverse primer sequence RPtot (e.g., GGGAACGGACTGGTTTATGTATT (SEQ ID NO: 10)) indicate the bases of the primer that hybridize to the 5' end of EGFR exon 30 and lower case letters in the reverse primer sequence RPtot (e.g., cag (SEQ ID NO: 11)) indicate the bases of the primer that hybridize to the 3' end of EGFR exon 29. In the total EGFR probe provided by SEQ ID NO: 32, a "6" indicates a 5-propynyl dU base and a "7" indicates a 5-methyl dC base.

Further, the probe sequence provided in TABLE 2 is derived from the sense strand of the EGFR gene, but the technology also encompasses use of a probe having a sequence that is complementary to the sequence of PBtot provided in TABLE 2 (e.g., GAGGAAGGTGTCGT (SEQ ID NO: 12)). Embodiments provide that the dye D in probe PBtot is any moiety (e.g., a dye) that can fluoresce and allow effective association of the probe to the target. Embodiments provide that the quencher Q in probe PBtot at the opposite end from the dye D in probe PBtot is any moiety that effectively quenches the fluorescent dye D and allows effective association (e.g., hybridization) of these probes to their target sequences. In TABLE 2, the dye D is attached to PBtot at the 5' end of PBtot and the quencher Q is attached to PBtot at the 3' end of PBtot; however, the technology also includes a probe in which the dye D is attached to the probe at the 3' end of the probe and the quencher Q is attached to the probe at the 5' end of the probe. The probe in TABLE 2 does not limit the technology. For instance, the technology also provides embodiments in which a probe comprises a detectable label at the 5' end and/or at the 3' end, e.g., a probe that comprises a dye D at the 5' end or at the 3' end. Some embodiments provide a probe that does not comprise a quencher. In some embodiments, the primers and/or the probe are modified, e.g., to include a variety of binding enhancers such as a minor groove binder ("MGB") or a pdU or pdC nucleotide.

Beta-actin Internal Control Gene Amplification Primers and Hybridization Probes

Figure 3:
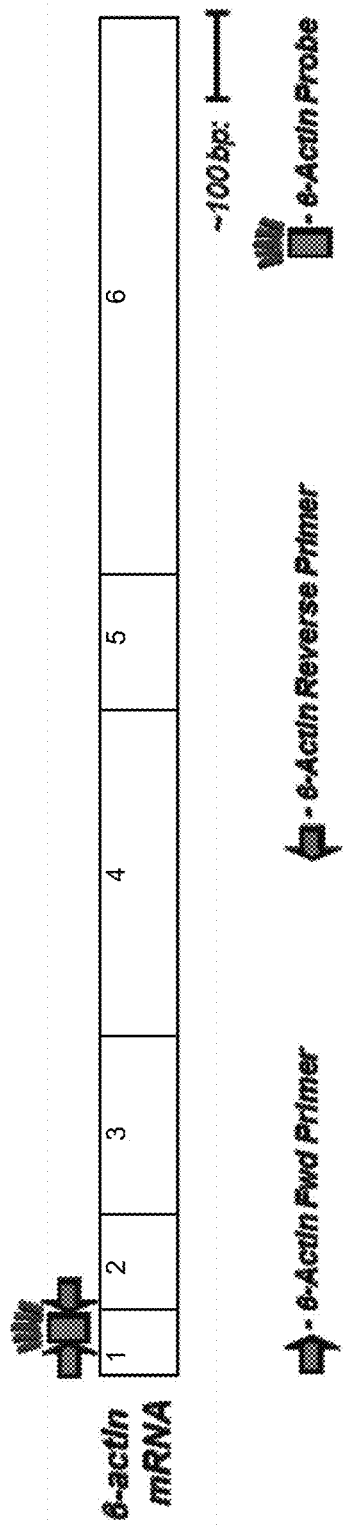
FIG. 3 is a schematic drawing showing the beta-actin mRNA and relative locations (e.g., binding site, sequence, and/or complementary sequence) of primers and probes. Exons comprising beta-actin mRNAs are depicted as numbered boxes. The location of primers and probes are denoted above the mRNA.

In some embodiments, the technology provided herein relates to the amplification and detection of RNA from an endogenous gene for use as an internal control. For example, during the development of embodiments of the technology described herein, two oligonucleotide primers ("RPact" and "FPact") and one hybridization probe ("PBact") were developed that target a house-keeping gene, e.g., beta-actin. Exemplary primer and probe sequences contemplated for use in the technology are provided in TABLE 3; see, e.g., FIG. 3 and FIG. 4. As used herein, the terms "FPact", "RPact", and "PBact" refer to forward primers, reverse primers, and hybridization probes targeting beta-actin (ACTB) RNA or beta-actin (ACTB) cDNA as described herein and as exemplified by the specific primers and probes contemplated and described.

These primers and probe find use in the amplification (e.g., by RT-PCR) and detection of beta-actin RNA. In particular, the reverse primer RPact anneals to a specific sequence spanning the splice junction of beta-actin exon 1 and beta-actin exon 2 (see, e.g., FIG. 3 and FIG. 4). Since RPact spans an exon/exon splice junction, RPact anneals specifically to beta-actin mRNA and thus provides an amplification product (e.g., a cDNA) from beta-actin mRNA, but RPact does not anneal to beta-actin genomic DNA and thus does not provide an amplification product from beta-actin genomic DNA. Amplification (e.g., by PCR) of the beta-actin cDNA is directed by reverse primer RPact in combination with the beta-actin forward primer FPact, which is specific to a sequence in the beta-actin exon 1. The beta-actin hybridization probe (PBact) targets beta-actin exon 1 sequences between FPact and RPact, thereby providing for the detection of the beta-actin amplicon (e.g., by real-time PCR) (see, e.g., FIG. 3 and FIG. 4).

TABLE 3 beta-actin oligonucleotides

| name | description | target site | sequence (5' to 3') | SEQ ID NO |
|---|---|---|---|---|
| RPact | beta-actin reverse primer | splice junction of beta-actin exon 1 and beta-actin exon 2 | TCATCATCCA TGGTGAGCtg gc | 13 |

TABLE 3-continued beta-actin oligonucleotides

| name | description | target site | sequence (5' to 3') | SEQ ID NO |
|---|---|---|---|---|
| FPact | beta-actin forward primer | beta-actin exon 1 | GAGCACAGAG CCTCGCCTTT G | 14 |
| PBact | beta-actin probe | beta-actin exon 1 | D- ATCCGCC GCCCGTCCAC ACC-Q | 15 |

In TABLE 3, upper case letters in the reverse primer sequence RPact (e.g., TCATCATCCATGGTGAG (SEQ ID NO: 16)) indicate the bases of the primer that hybridize to the 5' end of beta-actin exon 2 and lower case letters in the reverse primer sequence RPact (e.g., ctggc (SEQ ID NO: 17)) indicate the bases of the primer that hybridize to the 3' end of beta-actin exon 1. Further, the probe sequence provided in TABLE 3 is derived from the sense strand of the beta-actin gene, but the technology also encompasses use of a probe having a sequence that is complementary to the sequence of PBact provided in TABLE 3 (e.g., GGTGTG-GACGGGCGGCGGAT (SEQ ID NO: 18)). Embodiments provide that the dye D in probe PBact is any moiety (e.g., a dye) that can fluoresce and allow effective association of the probe to the target. Embodiments provide that the quencher Q in probe PBact at the opposite end from the dye D in probe PBact is any moiety that effectively quenches the fluorescent dye D and allows effective association (e.g., hybridization) of these probes to their target sequences. In TABLE 3, the dye D is attached to PBact at the 5' end of PBact and the quencher Q is attached to PBact at the 3' end of PBact; however, the technology also includes a probe in which the dye D is attached to the probe at the 3' end of the probe and the quencher Q is attached to the probe at the 5' end of the probe. The probe in TABLE 3 does not limit the technology. For instance, the technology also provides embodiments in which a probe comprises a detectable label at the 5' end and/or at the 3' end, e.g., a probe that comprises a dye D at the 5' end or at the 3' end. Some embodiments provide a probe that does not comprise a quencher. In some embodiments, the primers and/or the probe are modified, e.g., to include a variety of binding enhancers such as a minor groove binder ("MGB") or a pdU or pdC nucleotide.

Alternative Internal Control Gene Amplification Primers and Hybridization Probes While the beta-actin primers and probe described herein are preferred for certain embodiments of the technology, some embodiments of the technology provide other primer and probe sets for the amplification and detection of RNA from two alternate endogenous control gene targets, e.g., abelson tyrosine kinase (ABL, also known as ABL1 and c-abl) and glucose-6-phosphate dehydrogenase (G6PD). During the development of embodiments of the technology provided herein, two oligonucleotide primers ("RPabl" and "FPabl") and one hybridization probe ("PBabl") were developed that target the house-keeping gene ABL. Exemplary primer and probe sequences contemplated for use in the technology are provided in TABLE 4. In addition, during the development of embodiments of the technology provided herein, two additional oligonucleotide primers ("RPg6pd" and "FPg6pd") and one additional hybridization probe ("PBg6pd") were developed that target the house-keeping gene G6PD. Exemplary primer and probe sequences contemplated for use in the technology are provided in TABLE 4. Accordingly, embodiments of the technology provide that the ACTB, ABL, and/or G6PD are used as endogenous control targets; accordingly, embodiments provide that the primer/probe sets for ABL and/or G6PD are substituted for (or supplement) the ACTB primer/probe set described hereinabove. As used herein, the terms "FPabl", "RPabl", and "PBabl" refer to forward primers, reverse primers, and hybridization probes targeting ABL RNA or ABL cDNA as described herein and as exemplified by the specific primers and probes contemplated and described. As used herein, the terms "FPg6pd", "RPg6pd", and "PBg6pd" refer to forward primers, reverse primers, and hybridization probes targeting G6PD RNA or G6PD cDNA as described herein and as exemplified by the specific primers and probes contemplated and described.

These primer and probe sets find use in the amplification (e.g., by RT-PCR) and detection of ABL RNA and/or G6PD RNA. In particular, reverse primer RPabl anneals to a sequence within ABL exon 4 and directs the reverse transcription of ABL RNA (e.g., to produce ABL cDNA). Forward primer FPabl anneals to a sequence spanning the splice junction of ABL exon 3 and ABL exon 4. In the ABL gene, exon 3 is separated from exon 4 by a large intron. Thus, use of forward primer FPabl in combination with reverse primer RPabl directs the amplification of ABL cDNA. The distance between the FPabl and RPabl binding sites in the genomic ABL gene sequence prevents amplification from the ABL genomic DNA and thus FPabl and RPabl do not provide an amplification product from ABL genomic DNA. Accordingly, this primer design provides amplicons from ABL RNA and/or ABL cDNA, but does not produce amplicons from ABL genomic DNA. The hybridization probe PBabl binds to ABL sequence between the ABL forward and reverse primers FPabl and RPabl, and thereby provides for the detection of the ABL amplicon.

Reverse primer RPg6pd anneals to a sequence within G6PD exon 3 and directs reverse transcription of G6PD RNA. Forward primer FPg6pd anneals to a sequence within G6PD exon 2 and, in combination with reverse primer RPg6pd, provides for the amplification of the G6PD cDNA. The resulting amplicon spans sequences from G6PD exon 2 and G6PD exon 3. In the G6PD gene, exon 2 is separated from exon 3 by a large intron. Thus, use of forward primer FPg6pd in combination with reverse primer RPg6pd directs the amplification of G6PD cDNA. The distance between the FPg6pd and RPg6pd binding sites in the genomic G6PD gene sequence prevents amplification from the G6PD genomic DNA and thus FPg6pd and RPg6pd do not provide an amplification product from G6PD genomic DNA. Accordingly, this primer design provides amplicons derived from G6PD RNA and/or G6PD cDNA, but does not produce amplicons from G6PD genomic DNA. Hybridization probe PBg6pd binds to a sequence at the junction of G6PD exon 2 and G6PD exon 3, and thereby provides for the detection of the G6PD amplicon. G6PD exon 2 is separated from G6PD exon 3 by an intron in the genomic sequence; thus, the G6PD exon 2/G6PD exon 3 junction sequence targeted by PBg6pd is specific to G6PD RNA and is not present in the G6PD DNA. Accordingly, the G6PD signal detected by the PBg6pd probe is derived from G6PD RNA and/or G6PD cDNA, and is not from G6PD genomic DNA.

TABLE 4

ABL and G6PD oligonucleotides

| name | description | target site | sequence (5' to 3') | SEQ ID NO |
|---|---|---|---|---|
| RPabl | ABL reverse primer | ABL exon 4 | ACCGTTGAAT GATGATGAAC CAACT | 19 |
| FPabl | ABL forward primer | ABL exon 3 | AACACTGCTT CTGATGGCAA Gct | 20 |
| PBabl | ABL probe | ABL exon 4 | D-CTCCTCCG AGAGCCGCTT CAACACC-Q | 21 |
| RPg6pd | G6PD reverse primer | G6PD exon 3 | AGATGGTGGG GTAGATCTTC TTCTTG | 22 |
| FPg6pd | G6PD forward primer | G6PD exon 2 | ATGCCTTCCA TCAGTCGGAT ACA | 23 |
| PBg6pd | G6PD probe | splice junction of G6PD exon 2 and G6PD exon 3 | D-CATGGGTG CATCGggtga cctg-Q | 24 |

In TABLE 4, upper case letters in the forward primer sequence FPabl (e.g., AACACTGCTTCTGATGGCAAG (SEQ ID NO: 25)) indicate the bases of the primer that hybridize to the 3' end of ABL exon 3 and lower case letters in the reverse primer sequence RPabl (e.g., ct (SEQ ID NO: 26)) indicate the bases of the primer that hybridize to the 5' end of ABL exon 4. Upper case letters in the probe sequence PBg6pd (e.g., CATGGGTGCATCG (SEQ ID NO: 27)) indicate the bases of the probe that hybridize to the 3' end of G6PD exon 2 and lower case letters in the probe sequence PBg6pd (e.g., ggtgacctg (SEQ ID NO: 28)) indicate the bases of the probe that hybridize to the 5' end of G6PD exon 3. Further, the probe sequences for PBabl and PBg6pd provided in TABLE 4 are derived from the sense strands of the ABL gene and the G6PD gene, respectively, but the technology also encompasses use of a probe having a sequence that is complementary to the sequence of PBabl provided in TABLE 4 (e.g., GGTGTTGAAGCG-GCTCTCGGAGGAG (SEQ ID NO: 29)) and use of a probe having a sequence that is complementary to the sequence of PBg6pd provided in TABLE 4 (e.g., caggtcaccCGATG-CACCCATG (SEQ ID NO: 30)).

Embodiments provide that the dye D in probe PBabl and/or in probe PBg6pd is any moiety (e.g., a dye) that can fluoresce and allow effective association of the probe to the target. Embodiments provide that the quencher Q in probe PBabl and/or in probe PBg6pd at the opposite end from the dye D in probe PBabl and/or in probe PBg6pd is any moiety that effectively quenches the fluorescent dye D and allows effective association (e.g., hybridization) of these probes to their target sequences. In TABLE 4, the dye D is attached to PBabl and/or PBg6pd at the 5' end of PBabl and/or PBg6pd and the quencher Q is attached to PBabl and/or PBg6pd at the 3' end of PBabl and/or PBg6pd; however, the technology also includes probes in which the dye D is attached to the probe at the 3' end of the probe and the quencher Q is attached to the probe at the 5' end of the probe. The probes in TABLE 4 do not limit the technology. For instance, the technology also provides embodiments in which a probe comprises a detectable label at the 5' end and/or at the 3' end, e.g., a probe that comprises a dye D at the 5' end or at the 3' end. Some embodiments provide a probe that does not comprise a quencher. In some embodiments, the primers and/or the probe are modified, e.g., to include a variety of binding enhancers such as a minor groove binder ("MGB") or a pdU or pdC nucleotide.

A summary of the exemplary contemplated and described primers and probes (e.g., primer sequences and probe sequences) is provided in TABLE 5.

TABLE 5

Exemplary sequences of primers and probes

| oligo name | short name | oligo type | sequence (5' to 3') | SEQ ID NO: |
|---|---|---|---|---|
| EGvIIIi1_-58to-41 | FPvIII | primer | CTCCTGGCGC TGCTGGCT | 2 |
| EGvIII-A | | primer | CGTGATCTGT CACCACATAA TTACCTTTC | 33 |
| EGvIIIi1_-39 to-21pFAM | PBvIII | probe | CGCTCTGCCC GGCGAGTCG | 3 |
| EGFRvIII Rev_D | RPvIII | primer | ACCACATAAT TACctttc | 1 |
| EFFRvIII Rev | RPvIII | primer | CGTGATCTGT CACCACATAA TTACctttc | 31 |
| EGwti7_-28to-9 | FPwtA | primer | GGTGCCACCT GCGTGAAGAA | 34 |
| EGv3i1_+36to+18 | RPvIIIB | primer | GGACGCACGA GCCGTGATC | 35 |
| EGFRwti7_-7to+8 NED MGB | RPwtB | probe | TGTCCCCGTA ATTAT | 36 |
| EGwti29_-47to-25 | FPtot | primer | CGCCTTGACT GAGGACAGCA TAG | 8 |
| EGwti29_+23to-3 | RPtot | primer | GGGAACGGAC TGGTTTATGT ATTcag | 7 |
| EGi29_-24to-11pNED | PBtot | probe | ACGACACCTT CCTC | 9 |
| Total EGFR Probe | PBtot | probe | A7A C76 67C 67C 7AG 6G | 32 |
| bActl1_-53to-33 | FPact | primer | GAGCACAGAG CCTCGCCTTT G | 14 |
| bActl1_-29 to-10pCY5 | PBact | probe | ATCCGCCGCC CGTCCACACC | 15 |
| bActl1_+17to-5 | RPact | primer | TCATCATCCA TGGTGAGctg gc | 13 |
| ABLi3_fwd-21to+2 | FPabl | primer | AACACTGCTT CTGATGGCAA Gct | 20 |

TABLE 5-continued

Exemplary sequences of primers and probes

| oligo name | short name | oligo type | sequence (5' to 3') | SEQ ID NO: |
|---|---|---|---|---|
| ABLi3+65to+41 | RPabl | primer | ACCGTTGAAT GATGATGAAC CAACT | 19 |
| ABLi3+9to+33p | PBabl | probe | CTCCTCCGAG AGCCGCTTCA ACACC | 21 |
| G6PDi2_fwd-50to-28 | | primer | ATGCCTTCCA TCAGTCGGAT ACA | 37 |
| G6PDi2fwd-57to-39 | FPg6pd | primer | ATGCCTTCCA TCAGTCGGAT ACA | 23 |
| G6PDi2_rev-37to-12 | RPg6pd | primer | AGATGGTGGG GTAGATCTTC TTCTTG | 22 |
| G6PDv1_fwd346 to367pCY5 | PBg6pd | probe | CATGGGTGCA TCGggtgacc tg | 24 |

In TABLE 5, probes with names comprising "NED", "FAM", and "CY5" indicate an oligonucleotide that comprises in some embodiments a NED, FAM, and CY5 fluorescent moiety, respectively. Probes with names comprising "MGB" indicate an oligonucleotide that comprises in some embodiments a minor groove binder. In the total EGFR probe provided by SEQ ID NO: 32, a "6" indicates a 5-propynyl dU base and a "7" indicates a 5-methyl dC base.

Exemplary Compositions and Reaction Mixtures

Some embodiments provide a reaction mixture comprising a primer and/or a probe for the detection of EGFRvIII expression and/or for detection of EGFR expression. Particular embodiments provide a reaction mixture comprising a primer and/or a probe for the detection of EGFRvIII mRNA and/or for detection of EGFR mRNA. For example, some embodiments provide a reaction mixture comprising a primer and/or a probe as described in TABLE 1, TABLE 2, TABLE 3, TABLE 4, and/or TABLE 5. Some embodiments provide a reaction mixture comprising one or more of the primers RPvIII and/or FPvIII and the probe PBvIII; and/or one or more of the primers RPtot and/or FPtot and the probe PBtot.

Some embodiments of reaction mixtures further comprise primers and/or probes for the detection of an internal (e.g., endogenous) control (e.g., a gene such as ACTB, ABL, and/or G6PD). For example, some embodiments of reaction mixtures comprise one or more of the primers RPact and/or FPact and the probe PBact; one or more of the primers RPabl and/or FPabl and the probe PBabl; and/or one or more of the primers RPg6pd and/or FPg6pd and the probe PBg6pd. In an exemplary embodiment, a reaction mixture comprises RPvIII, FPvIII, PBvIII, RPact, FPact, and PBact. In an exemplary embodiment, a reaction mixture comprises RPtot, FPtot, PBtot, RPact, FPact, and PBact. In an exemplary embodiment, a reaction mixture comprises RPvIII, FPvIII, PBvIII, RPtot, FPtot, PBtot, RPact, FPact, and PBact.

Embodiments of reaction mixtures comprise one or more of the above-mentioned oligonucleotide primers and probes (e.g., a primer and/or a probe for the detection of EGFRvIII mRNA and/or EGFRvIII expression and/or for detection of EGFR mRNA and/or EGFR expression) and components associated with nucleic acid amplification, such as dNTP mix (e.g., a mixture of dATP, dCTP, dGTP, and/or dTTP), buffer, polymerase enzyme (e.g., a thermostable polymerase such as Taq, Tth, Pfu, etc.), and/or divalent ion (e.g., $Mg^{2+}$ and/or $Mn^{2+}$) as activation reagent.

Some embodiments provide a reaction mixture comprising primers. For example, some embodiments provide a reaction mixture comprising a primer for the detection of EGFRvIII expression and/or for detection of EGFR expression. Embodiments provide a reaction mixture comprising a primer for the detection of EGFRvIII mRNA and/or for detection of EGFR mRNA. For example, some embodiments provide a reaction mixture comprising a primer as described in TABLE 1, TABLE 2, TABLE 3, TABLE 4, and/or TABLE 5. Alternatively, some embodiments comprise providing a reaction mixture comprising one or more of the primers RPvIII and/or FPvIII; and/or one or more of the primers RPtot and/or FPtot.

Some embodiments provide a reaction mixture comprising primers for the detection of an internal (e.g., endogenous) control (e.g., a gene such as ACTB, ABL, and/or G6PD). That is, some embodiments provide a reaction mixture that does not comprise a probe (e.g., some embodiments provide that a probe is added in later subsequent steps). For example, some embodiments provide a reaction mixture comprising one or more of the primers RPact and/or FPact; one or more of the primers RPabl and/or FPabl; and/or one or more of the primers RPg6pd and/or FPg6pd. In an exemplary embodiment, a reaction mixture comprises RPvIII, FPvIII, RPact, and FPact. In an exemplary embodiment, a reaction mixture comprises RPtot, FPtot, RPact, and FPact. In an exemplary embodiment, a reaction mixture comprises RPvIII, FPvIII, RPtot, FPtot, RPact, and FPact.

Embodiments provide a reaction mixture comprising one or more of the above-mentioned oligonucleotide primers (e.g., a primer for the detection of EGFRvIII mRNA and/or EGFRvIII expression and/or for detection of EGFR mRNA and/or EGFR expression) and components associated with nucleic acid amplification, such as dNTP mix (e.g., a mixture of dATP, dCTP, dGTP, and/or dTTP), buffer, polymerase enzyme (e.g., a thermostable polymerase such as Taq, Tth, Pfu, etc.), and/or divalent ion (e.g., $Mg^{2+}$ and/or $Mn^{2+}$) as activation reagent.

Further embodiments provide an assay mixture comprising a reaction mixture as described above and a test sample. In particular embodiments, the test sample is a sample in need of testing for one or more of EGFRvIII mRNA presence or quantity, EGFRvIII expression level, EGFR mRNA presence or quantity, and/or EGFR expression level. In some embodiments, the test sample is RNA (e.g., total RNA) purified from a biological sample (e.g., cells, tissues, etc. from an organism). Accordingly, in some embodiments the sample (e.g., and the assay mixture) comprises purified RNA (e.g., from a biological sample) and thus potentially comprises EGFRvIII transcripts (e.g., mRNA) and/or total EGFR transcripts (e.g., mRNA). In some embodiments, an assay mixture is tested to identify the sample as comprising or not comprising (e.g., lacking) EGFRvIII mRNA. In some embodiments, a sample "not comprising" or "lacking" EGFPvIII mRNA is a sample in which EGFPvIII mRNA is absent, a sample in which EGFPvIII mRNA is undetectable, and/or a sample in which EGFPvIII mRNA amount is below a detection threshold.

As discussed above, some embodiments of the technology relate to reaction mixtures for detecting EGFRvIII expression (e.g., for detecting EGFRvIII mRNA or EGFRvIII cDNA) and/or for detecting and/or quantifying total EGFR expression (e.g., for detecting and/or quantifying total EGFR mRNA or cDNA produced from total EGFR mRNA). Some embodiments of the technology relate to reaction mixtures for detecting EGFRvIII expression (e.g., for detecting EGFRvIII mRNA or EGFRvIII cDNA) and/or for detecting and/or quantifying total EGFR expression (e.g., for detecting and/or quantifying total EGFR mRNA or cDNA produced from total EGFR mRNA) relative to the expression of a control mRNA such as, e.g., ACTB, ABL, or G6PD.

For instance, some embodiments provide a reaction mixture comprising a set of primers for detecting EGFRvIII mRNA, e.g., an oligonucleotide comprising, consisting of, or consisting essentially of a sequence according to SEQ ID NO: 1 or SEQ ID NO: 31 (e.g., an oligonucleotide comprising, consisting of, or consisting essentially of a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 1 or SEQ ID NO: 31 or that is 100% identical to SEQ ID NO: 1 or SEQ ID NO: 31) and an oligonucleotide comprising, consisting of, or consisting essentially of a sequence according to SEQ ID NO: 2 (e.g., an oligonucleotide comprising, consisting of, or consisting essentially of a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 2 or that is 100% identical to SEQ ID NO: 2). In some embodiments, reaction mixtures further comprise a probe for detecting EGFRvIII, e.g., an oligonucleotide comprising, consisting of, or consisting essentially of a sequence according to SEQ ID NO: 3 (e.g., an oligonucleotide comprising, consisting of, or consisting essentially of a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 3 or that is 100% identical to SEQ ID NO: 3). In some embodiments, the oligonucleotide comprising, consisting of, or consisting essentially of a sequence according to SEQ ID NO: 3 comprises a detectable label (e.g., a fluorescent moiety). In some embodiments, the oligonucleotide comprising, consisting of, or consisting essentially of a sequence according to SEQ ID NO: 3 comprises a detectable label (e.g., a fluorescent moiety) and a quencher.

Some embodiments of the technology relate to reaction mixtures for detecting EGFRvIII expression (e.g., for detecting EGFRvIII mRNA or cDNA) and/or for detecting and/or quantifying total EGFR expression (e.g., for detecting and/or quantifying total EGFR mRNA or cDNA produced from total EGFR mRNA). For instance, some embodiments provide a reaction mixture comprising a set of primers for detecting EGFRvIII mRNA, e.g., an oligonucleotide comprising, consisting of, or consisting essentially of a sequence according to SEQ ID NO: 1 or SEQ ID NO: 31 (e.g., an oligonucleotide comprising, consisting of, or consisting essentially of a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 1 or SEQ ID NO: 31 or that is 100% identical to SEQ ID NO: 1 or SEQ ID NO: 31) and an oligonucleotide comprising, consisting of, or consisting essentially of a sequence according to SEQ ID NO: 2 (e.g., an oligonucleotide comprising, consisting of, or consisting essentially of a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 2 or that is 100% identical to SEQ ID NO: 2). In some embodiments, reaction mixtures further comprise a probe for detecting EGFRvIII, e.g., an oligonucleotide comprising, consisting of, or consisting essentially of a sequence according to SEQ ID NO: 3 (e.g., an oligonucleotide comprising, consisting of, or consisting essentially of a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 3 or that is 100% identical to SEQ ID NO: 3). In some embodiments, the oligonucleotide comprising, consisting of, or consisting essentially of a sequence according to SEQ ID NO: 3 comprises a detectable label (e.g., a fluorescent moiety). In some embodiments, the oligonucleotide comprising, consisting of, or consisting essentially of a sequence according to SEQ ID NO: 3 comprises a detectable label (e.g., a fluorescent moiety) and a quencher. And, in some embodiments, reaction mixtures further comprise a set of primers for detecting and/or quantifying total EGFR mRNA, e.g., an oligonucleotide comprising, consisting of, or consisting essentially of a sequence according to SEQ ID NO: 7 (e.g., an oligonucleotide comprising, consisting of, or consisting essentially of a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 7 or that is 100% identical to SEQ ID NO: 7) and an oligonucleotide comprising, consisting of, or consisting essentially of a sequence according to SEQ ID NO: 8 (e.g., an oligonucleotide comprising, consisting of, or consisting essentially of a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 8 or that is 100% identical to SEQ ID NO: 8). In some embodiments, reaction mixtures further comprise a probe for detecting and/or quantifying total EGFR, e.g., an oligonucleotide comprising, consisting of, or consisting essentially of a sequence according to SEQ ID NO: 9 or SEQ ID NO: 32 or SEQ ID NO: 32 (e.g., an oligonucleotide comprising, consisting of, or consisting essentially of a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 9 or SEQ ID NO: 32 or SEQ ID NO: 32 or that is 100% identical to SEQ ID NO: 9 or SEQ ID NO: 32 or SEQ ID NO: 32). In some embodiments, the oligonucleotide comprising, consisting of, or consisting essentially of a sequence according to SEQ ID NO: 9 or SEQ ID NO: 32 or SEQ ID NO: 32 comprises a detectable label (e.g., a fluorescent moiety). In some embodiments, the oligonucleotide comprising, consisting of, or consisting essentially of a sequence according to SEQ ID NO: 9 or SEQ ID NO: 32 or SEQ ID NO: 32 comprises a detectable label (e.g., a fluorescent moiety) and a quencher.

Some embodiments of the technology relate to reaction mixtures for detecting and/or quantifying total EGFR expression. In some embodiments, reaction mixtures further comprise a set of primers for detecting and/or quantifying total EGFR mRNA, e.g., an oligonucleotide comprising, consisting of, or consisting essentially of a sequence according to SEQ ID NO: 7 (e.g., an oligonucleotide comprising, consisting of, or consisting essentially of a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 7 or that is 100% identical to SEQ ID NO: 7) and an oligonucleotide comprising, consisting of, or consisting essentially of a sequence according to SEQ ID NO: 8 (e.g., an oligonucleotide comprising, consisting of, or consisting essentially of a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 8 or that is 100% identical to SEQ ID NO: 8). In some embodiments, reaction mixtures further comprise a probe for detecting and/or quantifying total EGFR, e.g., an oligonucleotide comprising, consisting of, or consisting essentially of a sequence according to SEQ ID NO: 9 or SEQ ID NO: 32 or SEQ ID NO: 32 (e.g., an oligonucleotide comprising, consisting of, or consisting essentially of a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 9 or SEQ ID NO: 32 or that is 100% identical to SEQ ID NO: 9 or SEQ ID NO: 32). In some embodiments, the oligonucleotide comprising, consisting of, or consisting essentially of a sequence according to SEQ ID NO: 9 or SEQ ID NO: 32 comprises a detectable label (e.g., a fluorescent moiety). In some embodiments, the oligonucleotide comprising, consisting of, or consisting essentially of a sequence according to SEQ ID NO: 9 or SEQ ID NO: 32 comprises a detectable label (e.g., a fluorescent moiety) and a quencher.

Further embodiments of reaction mixtures comprise a set of primers and a probe for the detection and/or quantification of a control mRNA such as ACTB, ABL, or G6PD. Thus, in some embodiments reaction mixtures comprise primers and a probe to detect ACTB, e.g., an oligonucleotide comprising, consisting of, or consisting essentially of a sequence according to SEQ ID NO: 13 (e.g., an oligonucleotide comprising, consisting of, or consisting essentially of a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 13 or that is 100% identical to SEQ ID NO: 13), an oligonucleotide comprising, consisting of, or consisting essentially of a sequence according to SEQ ID NO: 14 (e.g., an oligonucleotide comprising, consisting of, or consisting essentially of a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 14 or that is 100% identical to SEQ ID NO: 14), and a probe comprising an oligonucleotide sequence according to SEQ ID NO: 15 (e.g., an oligonucleotide comprising, consisting of, or consisting essentially of a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 15 or that is 100% identical to SEQ ID NO: 15). In some embodiments, reaction mixtures comprise primers and a probe to detect ABL, e.g., an oligonucleotide comprising, consisting of, or consisting essentially of a sequence according to SEQ ID NO: 19 (e.g., an oligonucleotide comprising, consisting of, or consisting essentially of a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 19 or that is 100% identical to SEQ ID NO: 19), an oligonucleotide comprising, consisting of, or consisting essentially of a sequence according to SEQ ID NO: 20 (e.g., an oligonucleotide comprising, consisting of, or consisting essentially of a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 20 or that is 100% identical to SEQ ID NO: 20), and a probe comprising an oligonucleotide sequence according to SEQ ID NO: 21 (e.g., an oligonucleotide comprising, consisting of, or consisting essentially of a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 21 or that is 100% identical to SEQ ID NO: 21). In some embodiments, reaction mixtures comprise primers and a probe to detect G6PD, e.g., an oligonucleotide comprising, consisting of, or consisting essentially of a sequence according to SEQ ID NO: 22 (e.g., an oligonucleotide comprising, consisting of, or consisting essentially of a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 22 or that is 100% identical to SEQ ID NO: 22), an oligonucleotide comprising, consisting of, or consisting essentially of a sequence according to SEQ ID NO: 23 (e.g., an oligonucleotide comprising, consisting of, or consisting essentially of a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 23 or that is 100% identical to SEQ ID NO: 23), and a probe comprising an oligonucleotide sequence according to SEQ ID NO: 24 (e.g., an oligonucleotide comprising, consisting of, or consisting essentially of a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 24 or that is 100% identical to SEQ ID NO: 24). In some embodiments, the oligonucleotide comprising, consisting of, or consisting essentially of a sequence according to SEQ ID NO: 15, SEQ ID NO: 21, and/or SEQ ID NO: 24 comprises a detectable label (e.g., a fluorescent moiety). In some embodiments, the oligonucleotide comprising, consisting of, or consisting essentially of a sequence according to SEQ ID NO: 15, SEQ ID NO: 21, and/or SEQ ID NO: 24 comprises a detectable label (e.g., a fluorescent moiety) and a quencher.

Embodiments of reaction mixtures comprise one or more of the above-mentioned oligonucleotide primers and/or probes (e.g., a primer and/or a probe for the detection of EGFRvIII mRNA and/or EGFRvIII expression and/or for detection of EGFR mRNA and/or EGFR expression) and components associated with nucleic acid amplification, such as dNTP mix (e.g., a mixture of dATP, dCTP, dGTP, and/or dTTP), buffer, polymerase enzyme (e.g., a thermostable polymerase such as Taq, Tth, Pfu, etc.), and/or divalent ion (e.g., $Mg^{2+}$ and/or $Mn^{2+}$) as activation reagent. Some embodiments provide reaction mixtures comprising only primers and some embodiments provide reaction mixtures comprising primers and probes.

Further embodiments provide an assay mixture comprising a reaction mixture as described above and a test sample. In particular embodiments, the test sample is a sample in need of testing for one or more of EGFRvIII mRNA presence or quantity, EGFRvIII expression level, EGFR mRNA presence or quantity, and/or EGFR expression level. In some embodiments, the test sample is RNA (e.g., total RNA) purified from a biological sample (e.g., cells, tissues, etc. from an organism). Accordingly, in some embodiments the sample (e.g., and the assay mixture) comprises purified RNA (e.g., from a biological sample) and thus potentially comprises EGFRvIII transcripts (e.g., mRNA) and/or total EGFR transcripts (e.g., mRNA). In some embodiments, an assay mixture is tested to identify the sample as comprising or not comprising (e.g., lacking) EGFRvIII mRNA. In some embodiments, a sample "not comprising" or "lacking" EGFPvIII mRNA is a sample in which EGFPvIII mRNA is absent, a sample in which EGFPvIII mRNA is undetectable, and/or a sample in which EGFPvIII mRNA amount is below a detection threshold.

Exemplary Methods

In some embodiments, the technology provides a diagnostic method. Particular embodiments provide a method comprising steps for, e.g., providing a reaction mixture comprising a primer and/or a probe for the detection of EGFRvIII expression and/or for detection of EGFR expression. Particular embodiments provide a reaction mixture comprising a primer and/or a probe for the detection of EGFRvIII mRNA and/or for detection of EGFR mRNA. For example, some embodiments provide a reaction mixture comprising a primer and/or a probe as described in TABLE 1, TABLE 2, TABLE 3, TABLE 4, and/or TABLE 5. Alternatively, some embodiments comprise providing a reaction mixture comprising one or more of the primers RPvIII and/or FPvIII and the probe PBvIII; and/or one or more of the primers RPtot and/or FPtot and the probe PBtot.

Some embodiments of methods further comprise providing a reaction mixture comprising primers and/or probes for the detection of an internal (e.g., endogenous) control (e.g., a gene such as ACTB, ABL, and/or G6PD). For example, some embodiments of methods comprise providing a reaction mixture comprising one or more of the primers RPact and/or FPact and the probe PBact; one or more of the primers RPabl and/or FPabl and the probe PBabl; and/or one or more of the primers RPg6pd and/or FPg6pd and the probe PBg6pd. In an exemplary embodiment, methods comprise a step of providing a reaction mixture comprising RPvIII, FPvIII, PBvIII, RPact, FPact, and PBact. In an exemplary embodiment, methods comprise a step of providing a reaction mixture comprising RPtot, FPtot, PBtot, RPact, FPact, and PBact. In an exemplary embodiment, methods comprise a step of providing a reaction mixture comprising RPvIII, FPvIII, PBvIII, RPtot, FPtot, PBtot, RPact, FPact, and PBact.

Embodiments of methods comprise providing a reaction mixture comprising one or more of the above-mentioned oligonucleotide primers and probes (e.g., a primer and/or a probe for the detection of EGFRvIII mRNA and/or EGFRvIII expression and/or for detection of EGFR mRNA and/or EGFR expression) and components associated with nucleic acid amplification, such as dNTP mix (e.g., a mixture of dATP, dCTP, dGTP, and/or dTTP), buffer, polymerase enzyme, and/or divalent ion as activation reagent.

Some embodiments provide a reaction mixture comprising primers. For example, embodiments provide a method comprising steps for, e.g., providing a reaction mixture comprising a primer for the detection of EGFRvIII expression and/or for detection of EGFR expression. Embodiments provide a reaction mixture comprising a primer for the detection of EGFRvIII mRNA and/or for detection of EGFR mRNA. For example, some embodiments provide a reaction mixture comprising a primer as provided in TABLE 1, TABLE 2, TABLE 3, TABLE 4, and/or TABLE 5. Alternatively, some embodiments comprise providing a reaction mixture comprising one or more of the primers RPvIII and/or FPvIII; and/or one or more of the primers RPtot and/or FPtot.

Some embodiments of methods further comprise providing a reaction mixture comprising primers for the detection of an internal (e.g., endogenous) control (e.g., a gene such as ACTB, ABL, and/or G6PD). For example, some embodiments of methods comprise providing a reaction mixture comprising one or more of the primers RPact and/or FPact; one or more of the primers RPabl and/or FPabl; and/or one or more of the primers RPg6pd and/or FPg6pd. In an exemplary embodiment, methods comprise a step of providing a reaction mixture comprising RPvIII, FPvIII, RPact, and FPact. In an exemplary embodiment, methods comprise a step of providing a reaction mixture comprising RPtot, FPtot, RPact, and FPact. In an exemplary embodiment, methods comprise a step of providing a reaction mixture comprising RPvIII, FPvIII, RPtot, FPtot, RPact, and FPact.

Embodiments of methods comprise providing a reaction mixture comprising one or more of the above-mentioned oligonucleotide primers (e.g., a primer for the detection of EGFRvIII mRNA and/or EGFRvIII expression and/or for detection of EGFR mRNA and/or EGFR expression) and components associated with nucleic acid amplification, such as dNTP mix (e.g., a mixture of dATP, dCTP, dGTP, and/or dTTP), buffer, polymerase enzyme, and/or divalent ion as activation reagent.

Further embodiments provide a step of adding a test sample to an embodiment of a reaction mixture as described above to provide an assay mixture. In particular embodiments, the test sample is a sample in need of testing for one or more of EGFRvIII mRNA presence or quantity, EGFRvIII expression level, EGFR mRNA presence or quantity, and/or EGFR expression level. In some embodiments, the test sample is RNA (e.g., total RNA) purified from a biological sample (e.g., cells, tissues, etc. from an organism). Accordingly, in some embodiments the sample (e.g., and the assay mixture) comprises purified RNA (e.g., from a biological sample) and thus potentially comprises EGFRvIII transcripts (e.g., mRNA) and/or total EGFR transcripts (e.g., mRNA). In some embodiments, it is an object of the methods provided to identify the sample as comprising or not comprising (e.g., lacking) EGFRvIII mRNA. In some embodiments, a sample "not comprising" or "lacking" EGFPvIII mRNA is a sample in which EGFPvIII mRNA is absent, a sample in which EGFPvIII mRNA is undetectable, and/or a sample in which EGFPvIII mRNA amount is below a detection threshold.

In some embodiments, it is an object of the methods provided to quantify EGFRvIII transcripts (e.g., mRNA) and/or to quantify total EGFR transcripts (e.g., mRNA). In some embodiments, quantification provides a result (e.g., a quantity or an amount) that is zero, greater than zero, or undetectable.

In some embodiments, methods comprise a reverse transcribing step, e.g., a step of exposing the assay mixture to conditions appropriate for reverse transcription of the EGFRvIII RNA, total EGFR RNA, and/or endogenous control gene RNA using primers (e.g., forward and/or reverse primers) of the assay mixture (e.g., as described above) to provide an RT-PCR product. In some embodiments, the RT-PCR product further comprises one or more cDNAs that are products of the reverse transcription of the EGFRvIII RNA, total EGFR RNA, and/or endogenous control gene RNA. Accordingly, in some embodiments the assay mixture further comprises one or more cDNAs. In some embodiments, the RT-PCR product is used to provide an amplification reaction mixture (e.g., in some embodiments, an amplification reaction mixture is or comprises the RT-PCR product).

In some embodiments, methods comprise amplifying an amplification reaction mixture (e.g., a mixture comprising the RT-PCR product (e.g., a mixture comprising the one or more cDNAs of the RT-PCR product)) using the forward primers and reverse primers as described above to provide an amplicon. In some embodiments, the methods further comprise quantifying and/or detecting the presence or absence of an amplicon with probes as described above, e.g., quantifying and/or detecting the presence or absence of amplified EGFRvIII, amplified total EGFR, and/or amplified endogenous control gene target sequences with probes as described above.

In some embodiments, the probes are provided in the assay mixture prior to reverse transcription and/or prior to amplification and, in some embodiments, probes are added to the amplicon after amplification.

In some embodiments, methods comprise a detecting step, e.g., a detecting step comprising measuring, assaying, determining, calculating, and/or comparing one or more of EGFRvIII expression level, EGFRvIII transcript amount, total EGFR expression level, total EGFR transcript amount, endogenous control gene (e.g., ACTB, ABL, G6PD) transcript amount, and/or endogenous control gene (e.g., ACTB, ABL, G6PD) expression level.

Accordingly, in some embodiments the methods comprise measuring EGFRvIII expression, EGFRvIII transcript amount, total EGFR expression, and/or total EGFR transcript amount. In some embodiments measuring EGFRvIII expression and/or measuring EGFRvIII transcript amount provides a quantitative EGFRvIII result. In some embodiments measuring total EGFR expression and/or total EGFR transcript amount provides a quantitative EGFR result.

In some embodiments, a quantitative EGFRvIII result is a quantitative measure of EGFRvIII expression and/or a quantitative measure of EGFRvIII transcript amount. In some embodiments, a quantitative EGFR result provides a quantitative measure of total EGFR expression and/or a quantitative measure of total EGFR transcript amount.

In some embodiments, the methods provide a qualitative result that is presence or absence of EGFRvIII expression and/or a qualitative result that is presence or absence of EGFRvIII expression. In some embodiments, the methods comprise measuring an endogenous control gene (e.g., ACTB, ABL, G6PD) transcript level and/or measuring an endogenous control gene (e.g., ACTB, ABL, G6PD) expression level to provide a quantitative measure of an endogenous control gene (e.g., ACTB, ABL, G6PD) transcript level and/or to provide a quantitative measure of endogenous control gene (e.g., beta-actin, ABL, G6PD) expression level.

The technology provides embodiments of methods for determining EGFRvIII expression level, EGFRvIII transcript (e.g., mRNA) level, total EGFR expression level, and/or total EGFR transcript (mRNA) level relative to endogenous control gene (e.g., ACTB, ABL, G6PD) transcript level and/or endogenous control gene (e.g., ACTB, ABL, G6PD) expression level, e.g., to provide a relative EGFRvIII expression, a relative EGFRvIII transcript amount, a relative total EGFR expression, and/or a relative total EGFR transcript amount. Accordingly, embodiments of the methods comprise comparing a quantitative EGFRvIII or EGFR result (e.g., a quantitative measure of EGFRvIII expression, a quantitative measure of EGFRvIII transcript amount, a quantitative measure of total EGFR expression, and/or a quantitative measure of total EGFR transcript amount) to a quantitative measure of an endogenous control gene (e.g., ACTB, ABL, G6PD) transcript level and/or a quantitative measure of an endogenous control gene (e.g., ACTB, ABL, G6PD) expression level. Some embodiments comprise computing a ratio of a quantitative EGFRvIII or EGFR result (e.g., a quantitative measure of EGFRvIII expression, a quantitative measure of EGFRvIII transcript amount, a quantitative measure of total EGFR expression, and/or a quantitative measure of total EGFR transcript amount) to a quantitative measure of an endogenous control gene (e.g., ACTB, ABL, G6PD) transcript level and/or a quantitative measure of endogenous control gene (e.g., ACTB, ABL, G6PD) expression level. In some embodiments, the ratio is compared to a known value (e.g., a value from a normal control) to provide an indication or diagnosis, e.g., an indication or diagnosis of a cancer (e.g., an indication or diagnosis that the subject from whom the sample was procured has a cancer or has a risk of having a cancer).

In some embodiments, methods employ a polymerase enzyme or an enzyme mix (e.g., in a reaction mixture and/or in an assay mixture comprising a reaction mixture and a sample) to catalyze both the reverse transcription of RNA sequences (e.g., by RT-PCR) and the amplification of DNA (e.g., by amplification of cDNA produced in the RT-PCR product by the reverse transcription of RNA in the assay mixture).

Accordingly, in some embodiments, the reverse transcribing step (e.g., producing cDNA from RNA in the assay mixture) and the amplifying step (e.g., producing DNA amplicons from the cDNA in the RT-PCR product) are performed in one tube (e.g., either simultaneously or sequentially), e.g., in a single-run, closed-tube format by an instrument capable of concurrent thermal cycling and signal (e.g., fluorescence) detection. Accordingly, in some embodiments the technology finds use in a real-time amplification. In some embodiments, the technology comprises use of a real-time amplification apparatus.

In some embodiments, methods comprise use of multiple primer and/or probe sets within a single assay mixture and/or within a single amplification reaction mixture, e.g., during the reverse transcribing step, during the amplification step, and/or during the detecting step. Accordingly, embodiments provide for the detection and quantification of EGFRvIII RNA, total EGFR RNA, and the endogenous internal control gene in a single reaction. For example, in some embodiments of the methods provided, the EGFRvIII primers and probe, the total EGFR primers and probe, and the endogenous control primer and probe are used in multiplex within the same reaction. In some embodiments, each probe is labeled with a different fluorescent dye to provide for differentiating the EGFRvIII, total EGFR, and endogenous control signals from each other (e.g., by detecting a different appropriate wavelength associated with the emission spectrum of each fluorescent dye). In some embodiments, EGFRvIII mRNA and total EGFR mRNA levels in the sample are quantified relative to the endogenous control RNA levels. Further, detection of the endogenous control RNA serves as a within-well sample validity control, e.g., as a control for cell adequacy, sample extraction, and/or amplification efficiency.

In some embodiments, the EGFRvIII primer/probe sets and the total EGFR primer/probe sets function independently from each other. Accordingly, if relative quantification of only EGFRvIII expression (e.g., EGFRvIII mRNA levels) is of interest, the method is configured to provide a reaction mixture comprising the EGFRvIII primer/probe set (e.g., by removing the total EGFR primer/probe set). Alternatively, if relative quantification of only total EGFR expression (e.g., total EGFR mRNA levels) is of interest, the method is configured to provide a reaction mixture comprising the total EGFR primer/probe set (e.g., by removing the EGFRvIII primer/probe set).

In alternate embodiments of the methods provided, the EGFRvIII primer/probe, total EGFR primer/probe, and endogenous control primer/probe are used in separate reactions (e.g., in singleplex), each reaction comprising an aliquot of the same RNA sample. Thus, in some embodiments the methods provide separate reaction mixtures comprising the EGFRvIII primer/probe, total EGFR primer/probe, and endogenous control primer/probe (e.g., a first reaction mixture comprising the EGFRvIII primer/probe, a second reaction mixture comprising total EGFR primer/probe, and a third reaction mixture comprising endogenous control primer/probe). Addition of an aliquot of a test sample (e.g., a sample in need of testing for one or more of EGFRvIII mRNA presence or quantity, EGFRvIII expression level, EGFR mRNA presence or quantity, and/or EGFR expression level (e.g., a test sample that comprises RNA (e.g., total RNA) purified from a biological sample (e.g., cells, tissues, etc. from an organism))) to each reaction mixture thus provides separate assay mixtures (e.g., a first assay mixture comprising the EGFRvIII primer/probe, a second assay mixture comprising total EGFR primer/probe, and a third assay mixture comprising endogenous control primer/probe) that are provided for reverse transcribing, amplifying, and detecting steps of the methods. In these embodiments, the EGFRvIII RNA level and/or the total EGFR RNA level in the sample are quantified relative to endogenous control RNA levels using between-well results from the independent EGFRvIII, total EGFR, and endogenous control reactions.

In some embodiments, the EGFRvIII primer/probe set and the total EGFR primer/probe set are used independently for qualitative (e.g., presence/absence) detection of EGFRvIII mRNA and/or total EGFR mRNA in a sample. In some embodiments, qualitative detection provides a result indicating that EGFRvIII mRNA and/or total EGFR mRNA is/are greater than or less than a threshold value. In some embodiments, the endogenous control primer/probe set is used in combination with other primer/probe sets (e.g., for detecting, quantifying, etc. EGFR or non-EGFR targets) to provide an endogenous internal control for relative quantification of RNA levels from targeted genes and/or to provide a sample validity control for cell adequacy, sample extraction, and/or amplification efficiency.

Fluorescent Moieties and Quenchers

In some embodiments, an oligonucleotide (e.g., a probe) comprises a detectable label. In some embodiments, the detectable label is a fluorescent moiety (e.g., a fluorogenic dye, also referred to as a "fluorophore" or a "fluor"). A wide variety of fluorescent moieties is known in the art and methods are known for linking a fluorescent moiety to a nucleotide prior to incorporation of the nucleotide into an oligonucleotide and for adding a fluorescent moiety to an oligonucleotide after synthesis of the oligonucleotide.

Examples of compounds that may be used as the fluorescent moiety include but are not limited to xanthene, anthracene, cyanine, porphyrin, and coumarin dyes. Examples of xanthene dyes that find use with the present technology include but are not limited to fluorescein, 6-carboxyfluorescein (6-FAM), 5-carboxyfluorescein (5-FAM), 5- or 6-carboxy-4, 7, 2',7'-tetrachlorofluorescein (TET), 5- or 6-carboxy-4'5'2'4'5'7' hexachlorofluorescein (HEX), 5' or 6'-carboxy-4',5'-dichloro-2',7'-dimethoxyfluorescein (JOE), 5-carboxy-2',4',5',7'-tetrachlorofluorescein (ZOE), rhodol, rhodamine, tetramethylrhodamine (TAMRA), 4,7-dichlorotetramethyl rhodamine (DTAMRA), rhodamine X (ROX), VIC dye, NED dye, MAX dye, ATTO dyes, and Texas Red. Examples of cyanine dyes that find use in embodiments of the technology include but are not limited to Cy 3, Cy 3.5, Cy 5, Cy 5.5, Cy 7, and Cy 7.5. Other fluorescent moieties and/or dyes that find use with the present technology include but are not limited to energy transfer dyes, composite dyes, and other aromatic compounds that give fluorescent signals. In some embodiments, the fluorescent moiety comprises a quantum dot.

Fluorescent dyes include, without limitation, d-Rhodamine acceptor dyes including Cy5, dichloro[R110], dichloro[R6G], dichloro[TAMRA], dichloro[ROX] or the like; fluorescein donor dyes including fluorescein, 6-FAM, 5-FAM, or the like; Acridine including Acridine orange, Acridine yellow, Proflavin, pH 7, or the like; Aromatic Hydrocarbons including 2-Methylbenzoxazole, Ethyl p-dimethylaminobenzoate, Phenol, Pyrrole, benzene, toluene, or the like; Arylmethine Dyes including Auramine O, Crystal violet, glycerol, Malachite Green, or the like; Coumarin dyes including 7-Methoxycoumarin-4-acetic acid, Coumarin 1, Coumarin 30, Coumarin 314, Coumarin 343, Coumarin 6, or the like; Cyanine Dyes including 1,1'-diethyl-2,2'-cyanine iodide, Cryptocyanine, Indocarbocyanine (C3) dye, Indodicarbocyanine (C5) dye, Indotricarbocyanine (C7) dye, Oxacarbocyanine (C3) dye, Oxadicarbocyanine (C5) dye, Oxatricarbocyanine (C7) dye, Pinacyanol iodide, Stains all, Thiacarbocyanine (C3) dye, Thiacarbocyanine (C3) dye, Thiadicarbocyanine (C5) dye, Thiatricarbocyanine (C7) dye, or the like; Dipyrrin dyes including N,N'-Difluoroboryl-1,9-dimethyl-5-(4-iodophenyl)-dipyrrin, N,N'-Difluoroboryl-1,9-dimethyl-5-1(4-(2-trimethylsilylethynyl), N,N'-Difluoroboryl-1,9-dimethyl-5-phenydipyrrin, or the like; Merocyanines including 4-(dicyanomethylene)-2-methyl-6-(p-dimethylaminostyryl)-4H-pyran (DCM), acetonitrile, 4-(dicyanomethylene)-2-methyl-6-(p-dimethylaminostyryl)-4H-pyran (DCM), 4-Dimethylamino-4'-nitrostilbene, Merocyanine 540, or the like; Miscellaneous Dyes including 4',6-Diamidino-2-phenylindole (DAPI), dimethylsulfoxide, 7-Benzylamino-4-nitrobenz-2-oxa-1,3-diazole, Dansyl glycine, Dansyl glycine, dioxane, Hoechst 33258, DMF, Hoechst 33258, Lucifer yellow CH, Piroxicam, Quinine sulfate, Quinine sulfate, Squarylium dye III, or the like; Oligophenylenes including 2,5-Diphenyloxazole (PPO), Biphenyl, POPOP, p-Quaterphenyl, p-Terphenyl, or the like; Oxazines including Cresyl violet perchlorate, Nile Blue, Nile Red, Oxazine 1, Oxazine 170, or the like; Polycyclic Aromatic Hydrocarbons including 9, 10-Bis(phenylethynyl) anthracene, 9, 10-Diphenylanthracene, Anthracene, Naphthalene, Perylene, Pyrene, or the like; polyene/polyynes including 1,2-diphenylacetylene, 1,4-diphenylbutadiene, 1,4-diphenylbutadiyne, 1,6-Diphenylhexatriene, Beta-carotene, Stilbene, or the like; Redox-active Chromophores including Anthraquinone, Azobenzene, Benzoquinone, Ferrocene, Riboflavin, Tris(2,2'-bipyridypruthenium(II), Tetrapyrrole, Bilirubin, Chlorophyll a, diethyl ether, Chlorophyll a, Chlorophyll b, Diprotonated-tetraphenylporphyrin, Hematin, Magnesium octaethylporphyrin, Magnesium octaethylporphyrin (MgOEP), Magnesium phthalocyanine (MgPc), PrOH, Magnesium phthalocyanine (MgPc), pyridine, Magnesium tetramesitylporphyrin (MgTMP), Magnesium tetraphenylporphyrin (MgTPP), Octaethylporphyrin, Phthalocyanine (Pc), Porphin, ROX, TAMRA, Tetra-t- butylazaporphine, Tetra-t-butylnaphthalocyanine, Tetrakis (2,6-dichlorophenyflporphyrin, Tetrakis(o-aminophenyflporphyrin, Tetramesitylporphyrin (TMP), Tetraphenylporphyrin (TPP), Vitamin B12, Zinc octaethylporphyrin (ZnOEP), Zinc phthalocyanine (ZnPc), pyridine, Zinc tetramesitylporphyrin (ZnTMP), Zinc tetramesitylporphyrin radical cation, Zinc tetraphenylporphyrin (ZnTPP), or the like; Xanthenes including Eosin Y, Fluorescein, basic ethanol, Rhodamine 123, Rhodamine 6G, Rhodamine B, Rose bengal, Sulforhodamine 101, or the like; or mixtures or combination thereof or synthetic derivatives thereof.

Several classes of fluorogenic dyes and specific compounds are known that are appropriate for particular embodiments of the technology: xanthene derivatives such as fluorescein, rhodamine, Oregon green, eosin, and Texas red; cyanine derivatives such as cyanine, indocarbocyanine, oxacarbocyanine, thiacarbocyanine, and merocyanine; naphthalene derivatives (dansyl and prodan derivatives); coumarin derivatives; oxadiazole derivatives such as pyridyloxazole, nitrobenzoxadiazole, and benzoxadiazole; pyrene derivatives such as cascade blue; oxazine derivatives such as Nile red, Nile blue, cresyl violet, and oxazine 170; acridine derivatives such as proflavin, acridine orange, and acridine yellow; arylmethine derivatives such as auramine, crystal violet, and malachite green; and tetrapyrrole derivatives such as porphin, phthalocyanine, bilirubin. In some embodiments the fluorescent moiety a dye that is xanthene, fluorescein, rhodamine, BODIPY, cyanine, coumarin, pyrene, phthalocyanine, phycobiliprotein, ALEXA FLUOR® 350, ALEXA FLUOR® 405, ALEXA FLUOR® 430, ALEXA FLUOR® 488, ALEXA FLUOR® 514, ALEXA FLUOR® 532, ALEXA FLUOR® 546, ALEXA FLUOR® 555, ALEXA FLUOR® 568, ALEXA FLUOR® 568, ALEXA FLUOR® 594, ALEXA FLUOR® 610, ALEXA FLUOR® 633, ALEXA FLUOR® 647, ALEXA FLUOR® 660, ALEXA FLUOR® 680, ALEXA FLUOR® 700, ALEXA FLUOR® 750, or a squaraine dye. In some embodiments, the label is a fluorescently detectable moiety as described in, e.g., Haugland (September 2005) MOLECULAR PROBES HANDBOOK OF FLUORESCENT PROBES AND RESEARCH CHEMICALS (10th ed.), which is herein incorporated by reference in its entirety.

In some embodiments the label (e.g., a fluorescently detectable label) is one available from ATTO-TEC GmbH (Am Eichenhang 50, 57076 Siegen, Germany), e.g., as described in U.S. Pat. Appl. Pub. Nos. 20110223677, 20110190486, 20110172420, 20060179585, and 20030003486; and in U.S. Pat. No. 7,935,822, each of which is incorporated herein by reference.

One of ordinary skill in the art will recognize that dyes having emission maxima outside these ranges may be used as well. In some cases, dyes ranging between 500 nm to 700 nm have the advantage of being in the visible spectrum and can be detected using existing photomultiplier tubes. In some embodiments, the broad range of available dyes allows selection of dye sets that have emission wavelengths that are spread across the detection range. Detection systems capable of distinguishing many dyes are known in the art.

In some embodiments, the technology comprises use of fluorescent dyes and/or molecules that quench (e.g., decrease, eliminate, and/or minimize) the fluorescence of another fluorescent dye. In some embodiments, an oligonucleotide comprises a quencher moiety. A wide variety of quencher moieties is known in the art. For example, in some embodiments an oligonucleotide comprises a quencher than is a Black Hole Quencher (e.g., BHQ-0, BHQ-1, BHQ-2, BHQ-3), a Dabcyl, an Iowa Black Quencher (e.g., Iowa Black FQ, Iowa Black RQ), an Eclipse quencher.

In some embodiments a BHQ-1 is used with a fluorescent moiety that has an emission wavelength from approximately 500-600 nm. In some embodiments a BHQ-2 is used with a fluorescent moiety that has an emission wavelength from approximately 550-675 nm. In some embodiments, a FRET pair is a fluorophore-quencher pair that provides quenching.

Some exemplary fluorophore-quencher pairs include FAM and BHQ-1, TET and BHQ-1, JOE and BHQ-1, HEX and BHQ-1, Cy3 and BHQ-2, TAMRA and BHQ-2, ROX and BHQ-2, Cy5 and BHQ-3, Cy5.5 and BHQ-3, FAM and BHQ-1, TET and BHQ-1, JOE and 3'-BHQ-1, HEX and BHQ-1, Cy3 and BHQ-2, TAMRA and BHQ-2, ROX and BHQ-2, Cy5 and BHQ-3, Cy5.5 and BHQ-3, or similar fluorophore-quencher pairs available from the commercial entities such as Biosearch Technologies, Inc. of Novato, Calif.

Subjects

In some embodiments, the technology is related to testing a subject (e.g., a human). In some embodiments, a sample is obtained from the subject for testing according to the technology provided. In some embodiments, the subject is in need of testing for the presence of a cancer or a neoplasm. In some embodiments, the subject is in need of testing to determine a risk of developing a cancer or a neoplasm.

In some embodiments, a subject is in need of testing to determine the likelihood of responding to a therapy and/or medical intervention. For example, in some embodiments a subject is in need of testing to determine the likelihood of responding to a therapy targeting EGFR (e.g., an anti-EGFR therapeutic agent, e.g., as described herein). For example, in some embodiments the subject has a tumor and the subject (e.g., the tumor) is tested to assess EGFRvIII presence and/or EGFR expression to determine if the subject and/or the tumor is/are likely to respond to a therapy targeting EGFR (e.g., an anti-EGFR therapeutic agent). For example, in some embodiments, presence of EGFRvIII and/or EGFR overexpression indicates that the subject is likely to respond to an anti-EGFR therapy, e.g., an anti-EGFR therapy as described herein.

In some embodiments, the technology is related to diagnosing a subject (e.g., a human). In some embodiments, a sample is obtained from the subject for testing according to the technology provided, e.g., to provide information to diagnose the subject. In some embodiments, the subject is in need of a diagnosis describing the presence or absence of a cancer or a neoplasm. In some embodiments, the subject is in need of a diagnosis to determine a risk of developing a cancer or a neoplasm.

In some embodiments, the subject is diagnosed for the presence or absence of a cancer that is lung cancer (e.g., non-small cell lung cancer), breast cancer, head and neck cancer, salivary gland cancer, colorectal cancer, pancreatic cancer, hepatocellular carcinoma, esophageal cancer, and/or glioblastoma.

In some embodiments, the subject is diagnosed for the risk of developing a cancer that is lung cancer (e.g., non-small cell lung cancer), breast cancer, head and neck cancer, salivary gland cancer, colorectal cancer, pancreatic cancer, hepatocellular carcinoma esophageal cancer, and/or glioblastoma.

In some embodiments, the subject does not have a mutation in KRAS. In some embodiments, the subject has been treated with platinum-based or chemotherapy (e.g., docetaxel).

In some embodiments, a level of EGFR expression that is higher than the normal level of EGFR expression (e.g., from a subject that does not have a cancer) indicates an increased EGFR expression. In some embodiments, a level of EGFR expression that is 1.5×, 2×, 2.5×, 3×, 3.5×, 4×, 4.5×, 5×, 6×, 7×, 8×, 9×, 10× or more than the normal level of EGFR expression (e.g., from a subject that does not have a cancer) indicates an increased EGFR expression. In some embodiments, a level of EGFR expression that is higher than the normal level of EGFR expression (e.g., from a subject that does not have a cancer) indicates that the subject is in need of a treatment targeting EGFR (e.g., an anti-EGFR therapeutic agent). In some embodiments, a level of EGFR expression that is 1.5×, 2×, 2.5×, 3×, 3.5×, 4×, 4.5×, 5×, 6×, 7×, 8×, 9×, 10× or more than the normal level of EGFR expression (e.g., from a subject that does not have a cancer) indicates that the subject is in need of a treatment targeting EGFR (e.g., an anti-EGFR therapeutic agent).

In some embodiments, detecting expression of EGFRvIII indicates that the subject is in need of a treatment targeting EGFR (e.g., an anti-EGFR therapeutic agent). In some embodiments, detecting expression of EGFRvIII (e.g., detecting expression greater than zero and/or above the limit of detection) indicates that the subject is in need of a treatment targeting EGFR (e.g., an anti-EGFR therapeutic agent).

In some embodiments, a level of EGFR expression that is higher than the normal level of EGFR expression (e.g., from a subject that does not have a cancer) indicates that the subject has a cancer that is treatable with a treatment targeting EGFR (e.g., an anti-EGFR therapeutic agent). In some embodiments, a level of EGFR expression that is 1.5×, 2×, 2.5×, 3×, 3.5×, 4×, 4.5×, 5×, 6×, 7×, 8×, 9×, 10× or more than the normal level of EGFR expression (e.g., from a subject that does not have a cancer) indicates that the subject has a cancer that is treatable with a treatment targeting EGFR (e.g., an anti-EGFR therapeutic agent).

In some embodiments, detecting expression of EGFRvIII indicates that the subject has a cancer that is treatable with a treatment targeting EGFR (e.g., an anti-EGFR therapeutic agent). In some embodiments, detecting expression of EGFRvIII (e.g., detecting expression greater than zero and/or above the limit of detection) indicates that the subject has a cancer that is treatable with a treatment targeting EGFR (e.g., an anti-EGFR therapeutic agent).

Therapies

In some embodiments, the technology is related to therapies, e.g., cancer therapies. For example, in some embodiments a subject is tested for cancer and then treated for cancer. In particular embodiments, EGFR expression and/or EGFRvIII expression is assayed in a sample from a subject and the subject is treated with an anti-EGFR therapeutic agent. Particular anti-EGFR therapeutic agents include, but are not limited to, tyrosine kinase inhibitors (e.g., an adenosine triphosphate analog, e.g., an anilinoquinazoline (e.g., gefitinib, canertinib), lapatinib, erlotinib, etc.) and antibodies (e.g., monoclonal antibodies) such as, e.g., Cetuximab (Erbitux), Panitumumab, ABT-806, and ABT-414.

In some embodiments, the anti-EGFR therapeutic agent is Vandetanib (Caprelsa), Panitumumab (Vectibix), Gefitinib (Iressa), Erlotinib (Tarceva), or Afatinib (Gilotrif).

Some embodiments comprise treatment with a therapy targeting signaling downstream of EGFR such as a therapy targeting the genes or the product(s) of genes (e.g., RNA and/or protein) encoding KRAS, BRAF, MEK, ERK, PI3K, phospholipase C gamma, AKT, and/or STAT.

Some embodiments provide a combination therapy comprising treating a subject with an anti-EGFR therapeutic agent and one or more of a radiation therapy or a chemotherapy (e.g., a platinum-based therapy, a topoisomerase inhibitor, a taxane). Some embodiments provide a combination therapy comprising treating a subject with more than one anti-EGFR therapeutic agent. In some embodiments, combination therapies comprise treating a subject with a dietary bioactive agent such as capsaicin, genistein, or curcumin.

In some embodiments, the anti-EGFR therapy is an antibody that recognizes EGFR. The antibody can be a monoclonal antibody or a polyclonal antibody, and may be, for example, a human, humanized, or chimeric antibody. Monoclonal antibodies against target antigens are produced by a variety of techniques including conventional monoclonal antibody methodologies such as the somatic cell hybridization techniques of Köhler and Milstein (Nature, 256:495 (1975)). Although somatic cell hybridization procedures are preferred in some embodiments, other techniques for producing monoclonal antibodies are contemplated as well (e.g., viral or oncogenic transformation of B lymphocytes).

In some embodiments, the antibody is ABT-806, which is a humanized antibody specific for an epitope of EGFR that is exposed in deletion variant EGFRvIII or when wild-type EGF receptors are amplified, overexpressed, or activated (see, e.g., Zhang et al. (2013), J Nucl Med 54 (Supplement 2): 396).

In some embodiments, the antibody is ABT-414, which is an anti-EGFR monoclonal antibody drug conjugate (see, e.g., Johns et al. (2002) Int J Cancer 98(3): 398-408; Phillips et al. (2013) Mol Cancer Ther 12(11 Suppl): Abstract A250). ABT-414 targets cancer cells by combining both a chemotherapy drug (MMAF) with an antibody directed against the epidermal growth factor receptor (EGFR) (see, e.g., Jungbluth et al. (2003) Proc Natl Acad Sci USA 100(2): 639-44). This combination in a single drug is called an antibody drug conjugate (ADC). As an ADC, ABT-414 is stable in the bloodstream and releases the potent chemotherapy agent only inside targeted cancer cells. Studies are being conducted to determine if this approach can reduce the toxic side effects of traditional chemotherapy while enhancing anti-tumor activity (see, e.g., Doronina et al. (2008) Bioconjug Chem 19: 1960-3).

In some embodiments, a subject is tested to assess the presence, the absence, or the level of a disease (e.g., a cancer), e.g., by determining the presence of EGFRvIII expression (e.g., determining the presence of EGFRvIII mRNA) and/or by quantifying total EGFR to determine the risk of or the presence of cancer, and thereafter the subject is treated with an anti-cancer therapy (e.g., an anti-EGFR therapy) based on the outcome of the test. In some embodiments, a patient is tested, treated, and then tested again to monitor the response to therapy. In some embodiments, cycles of testing and treatment may occur without limitation to the pattern of testing and treating (e.g., test/treat, test/treat/test, test/treat/test/treat, test/treat/test/treat/test, test/treat/treat/test/treat/treat, etc.), the periodicity, or the duration of the interval between each testing and treatment phase.

Samples

In some embodiments, nucleic acids (e.g., RNA) are isolated from a biological sample containing a variety of other components, such as proteins, lipids, and non-template nucleic acids. Nucleic acids can be obtained from any material (e.g., cellular material (live or dead), extracellular material, environmental samples (e.g., metagenomic samples), synthetic material (e.g., amplicons such as provided by PCR or other amplification technologies)), tumor material, neoplastic material, etc., obtained from an animal. Nucleic acid molecules can be obtained directly from an organism or from a biological sample obtained from an organism, e.g., from blood, urine, cerebrospinal fluid, seminal fluid, saliva, sputum, stool, hair, sweat, tears, skin, and tissue. Exemplary samples include, but are not limited to, whole blood, lymphatic fluid, serum, plasma, buccal cells, sweat, tears, saliva, sputum, hair, skin, biopsy, cerebrospinal fluid (CSF), amniotic fluid, seminal fluid, vaginal excretions, serous fluid, synovial fluid, pericardial fluid, peritoneal fluid, pleural fluid, transudates, exudates, cystic fluid, bile, urine, gastric fluids, intestinal fluids, fecal samples, and swabs, aspirates (e.g., bone marrow, fine needle, etc.), washes (e.g., oral, nasopharyngeal, bronchial, bronchialalveolar, optic, rectal, intestinal, vaginal, epidermal, etc.), and/or other specimens.

Any tissue or body fluid specimen may be used as a source for nucleic acid for use in the technology, including forensic specimens, archived specimens, preserved specimens, and/or specimens stored for long periods of time, e.g., fresh-frozen, methanol/acetic acid fixed, or formalin-fixed paraffin embedded (FFPE) specimens and samples. Nucleic acid molecules can also be isolated from cultured cells, such as a primary cell culture or a cell line. The cells or tissues from which nucleic acids are obtained can be infected with a virus or other intracellular pathogen. In particular embodiments, a sample is total RNA extracted from a biological specimen or a cDNA library. A sample may also be isolated RNA or cDNA from a non-cellular origin, e.g. amplified/isolated RNA or DNA that has been stored in a freezer.

Nucleic acid molecules can be obtained, e.g., by extraction from a biological sample, e.g., by a variety of techniques such as those described by Maniatis, et al. (1982) Molecular Cloning: A Laboratory Manual, Cold Spring Harbor, N.Y. (see, e.g., pp. 280-281).

In various embodiments, a nucleic acid is amplified. Any amplification method known in the art may be used. Examples of amplification techniques that can be used include, but are not limited to, PCR, quantitative PCR, quantitative fluorescent PCR (QF-PCR), multiplex fluorescent PCR (MF-PCR), real time PCR, reverse transcription PCR (RT-PCR), single cell PCR, restriction fragment length polymorphism PCR (PCR-RFLP), hot start PCR, nested PCR, in situ polony PCR, in situ rolling circle amplification (RCA), bridge PCR, picotiter PCR, and emulsion PCR. Other suitable amplification methods include the ligase chain reaction (LCR), transcription amplification, self-sustained sequence replication, selective amplification of target polynucleotide sequences, consensus sequence primed polymerase chain reaction (CP-PCR), arbitrarily primed polymerase chain reaction (AP-PCR), degenerate oligonucleotide-primed PCR (DOP-PCR), and nucleic acid based sequence amplification (NABSA). Other amplification methods that can be used herein include those described in U.S. Pat. Nos. 5,242,794; 5,494,810; 4,988,617; and 6,582, 938.

Kits

Some embodiments of the technology relate to kits for detecting EGFRvIII expression (e.g., for detecting EGFRvIII mRNA or EGFRvIII cDNA) and/or for detecting and/or quantifying total EGFR expression (e.g., for detecting and/or quantifying total EGFR mRNA or cDNA produced from total EGFR mRNA). Some embodiments of the technology relate to kits for detecting EGFRvIII expression (e.g., for detecting EGFRvIII mRNA or EGFRvIII cDNA) and/or for detecting and/or quantifying total EGFR expression (e.g., for detecting and/or quantifying total EGFR mRNA or cDNA produced from total EGFR mRNA) relative to the expression of a control mRNA such as, e.g., ACTB, ABL, or G6PD.

For instance, some embodiments provide a kit comprising a set of primers for detecting EGFRvIII mRNA, e.g., an oligonucleotide comprising, consisting of, or consisting essentially of a sequence according to SEQ ID NO: 1 or SEQ ID NO: 31 (e.g., an oligonucleotide comprising, consisting of, or consisting essentially of a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 1 or SEQ ID NO: 31 or that is 100% identical to SEQ ID NO: 1 or SEQ ID NO: 31) and an oligonucleotide comprising, consisting of, or consisting essentially of a sequence according to SEQ ID NO: 2 (e.g., an oligonucleotide comprising, consisting of, or consisting essentially of a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 2 or that is 100% identical to SEQ ID NO: 2). In some embodiments, kits further comprise a probe for detecting EGFRvIII, e.g., an oligonucleotide comprising, consisting of, or consisting essentially of a sequence according to SEQ ID NO: 3 (e.g., an oligonucleotide comprising, consisting of, or consisting essentially of a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 3 or that is 100% identical to SEQ ID NO: 3). In some embodiments, the oligonucleotide comprising, consisting of, or consisting essentially of a sequence according to SEQ ID NO: 3 comprises a detectable label (e.g., a fluorescent moiety). In some embodiments, the oligonucleotide comprising, consisting of, or consisting essentially of a sequence according to SEQ ID NO: 3 comprises a detectable label (e.g., a fluorescent moiety) and a quencher.

Some embodiments of the technology relate to kits for detecting EGFRvIII expression (e.g., for detecting EGFRvIII mRNA or cDNA) and/or for detecting and/or quantifying total EGFR expression (e.g., for detecting and/or quantifying total EGFR mRNA or cDNA produced from total EGFR mRNA). For instance, some embodiments provide a kit comprising a set of primers for detecting EGFRvIII mRNA, e.g., an oligonucleotide comprising, consisting of, or consisting essentially of a sequence according to SEQ ID NO: 1 or SEQ ID NO: 31 (e.g., an oligonucleotide comprising, consisting of, or consisting essentially of a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 1 or SEQ ID NO: 31 or that is 100% identical to SEQ ID NO: 1 or SEQ ID NO: 31) and an oligonucleotide comprising, consisting of, or consisting essentially of a sequence according to SEQ ID NO: 2 (e.g., an oligonucleotide comprising, consisting of, or consisting essentially of a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 2 or that is 100% identical to SEQ ID NO: 2). In some embodiments, kits further comprise a probe for detecting EGFRvIII, e.g., an oligonucleotide comprising, consisting of, or consisting essentially of a sequence according to SEQ ID NO: 3 (e.g., an oligonucleotide comprising, consisting of, or consisting essentially of a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 3 or that is 100% identical to SEQ ID NO: 3). In some embodiments, the oligonucleotide comprising, consisting of, or consisting essentially of a sequence according to SEQ ID NO: 3 comprises a detectable label (e.g., a fluorescent moiety). In some embodiments, the oligonucleotide comprising, consisting of, or consisting essentially of a sequence according to SEQ ID NO: 3 comprises a detectable label (e.g., a fluorescent moiety) and a quencher. And, in some embodiments, kits further comprise a set of primers for detecting and/or quantifying total EGFR mRNA, e.g., an oligonucleotide comprising, consisting of, or consisting essentially of a sequence according to SEQ ID NO: 7 (e.g., an oligonucleotide comprising, consisting of, or consisting essentially of a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 7 or that is 100% identical to SEQ ID NO: 7) and an oligonucleotide comprising, consisting of, or consisting essentially of a sequence according to SEQ ID NO: 8 (e.g., an oligonucleotide comprising, consisting of, or consisting essentially of a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 8 or that is 100% identical to SEQ ID NO: 8). In some embodiments, kits further comprise a probe for detecting and/or quantifying total EGFR, e.g., an oligonucleotide comprising, consisting of, or consisting essentially of a sequence according to SEQ ID NO: 9 or SEQ ID NO: 32 (e.g., an oligonucleotide comprising, consisting of, or consisting essentially of a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 9 or SEQ ID NO: 32 or that is 100% identical to SEQ ID NO: 9 or SEQ ID NO: 32). In some embodiments, the oligonucleotide comprising, consisting of, or consisting essentially of a sequence according to SEQ ID NO: 9 or SEQ ID NO: 32 comprises a detectable label (e.g., a fluorescent moiety). In some embodiments, the oligonucleotide comprising, consisting of, or consisting essentially of a sequence according to SEQ ID NO: 9 or SEQ ID NO: 32 comprises a detectable label (e.g., a fluorescent moiety) and a quencher.

Some embodiments of the technology relate to kits for detecting and/or quantifying total EGFR expression. In some embodiments, kits further comprise a set of primers for detecting and/or quantifying total EGFR mRNA, e.g., an oligonucleotide comprising, consisting of, or consisting essentially of a sequence according to SEQ ID NO: 7 (e.g., an oligonucleotide comprising, consisting of, or consisting essentially of a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 7 or that is 100% identical to SEQ ID NO: 7) and an oligonucleotide comprising, consisting of, or consisting essentially of a sequence according to SEQ ID NO: 8 (e.g., an oligonucleotide comprising, consisting of, or consisting essentially of a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 8 or that is 100% identical to SEQ ID NO: 8). In some embodiments, kits further comprise a probe for detecting and/or quantifying total EGFR, e.g., an oligonucleotide comprising, consisting of, or consisting essentially of a sequence according to SEQ ID NO: 9 or SEQ ID NO: 32 (e.g., an oligonucleotide comprising, consisting of, or consisting essentially of a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 9 or SEQ ID NO: 32 or that is 100% identical to SEQ ID NO: 9 or SEQ ID NO: 32). In some embodiments, the oligonucleotide comprising, consisting of, or consisting essentially of a sequence according to SEQ ID NO: 9 or SEQ ID NO: 32 comprises a detectable label (e.g., a fluorescent moiety). In some embodiments, the oligonucleotide comprising, consisting of, or consisting essentially of a sequence according to SEQ ID NO: 9 or SEQ ID NO: 32 comprises a detectable label (e.g., a fluorescent moiety) and a quencher.

Further embodiments of kits comprise a set of primers and a probe for the detection and/or quantification of a control mRNA such as ACTB, ABL, or G6PD. Thus, in some embodiments kits comprise primers and a probe to detect ACTB, e.g., an oligonucleotide comprising, consisting of, or consisting essentially of a sequence according to SEQ ID NO: 13 (e.g., an oligonucleotide comprising, consisting of, or consisting essentially of a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 13 or that is 100% identical to SEQ ID NO: 13), an oligonucleotide comprising, consisting of, or consisting essentially of a sequence according to SEQ ID NO: 14 (e.g., an oligonucleotide comprising, consisting of, or consisting essentially of a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 14 or that is 100% identical to SEQ ID NO: 14), and a probe comprising an oligonucleotide sequence according to SEQ ID NO: 15 (e.g., an oligonucleotide comprising, consisting of, or consisting essentially of a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 15 or that is 100% identical to SEQ ID NO: 15). In some embodiments, kits comprise primers and a probe to detect ABL, e.g., an oligonucleotide comprising, consisting of, or consisting essentially of a sequence according to SEQ ID NO: 19 (e.g., an oligonucleotide comprising, consisting of, or consisting essentially of a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 19 or that is 100% identical to SEQ ID NO: 19), an oligonucleotide comprising, consisting of, or consisting essentially of a sequence according to SEQ ID NO: 20 (e.g., an oligonucleotide comprising, consisting of, or consisting essentially of a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 20 or that is 100% identical to SEQ ID NO: 20), and a probe comprising an oligonucleotide sequence according to SEQ ID NO: 21 (e.g., an oligonucleotide comprising, consisting of, or consisting essentially of a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 21 or that is 100% identical to SEQ ID NO: 21). In some embodiments, kits comprise primers and a probe to detect G6PD, e.g., an oligonucleotide comprising, consisting of, or consisting essentially of a sequence according to SEQ ID NO: 22 (e.g., an oligonucleotide comprising, consisting of, or consisting essentially of a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 22 or that is 100% identical to SEQ ID NO: 22), an oligonucleotide comprising, consisting of, or consisting essentially of a sequence according to SEQ ID NO: 23 (e.g., an oligonucleotide comprising, consisting of, or consisting essentially of a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 23 or that is 100% identical to SEQ ID NO: 23), and a probe comprising an oligonucleotide sequence according to SEQ ID NO: 24 (e.g., an oligonucleotide comprising, consisting of, or consisting essentially of a sequence or a reverse complement of a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 24 or that is 100% identical to SEQ ID NO: 24). In some embodiments, the oligonucleotide comprising, consisting of, or consisting essentially of a sequence according to SEQ ID NO: 15, SEQ ID NO: 21, and/or SEQ ID NO: 24 comprises a detectable label (e.g., a fluorescent moiety). In some embodiments, the oligonucleotide comprising, consisting of, or consisting essentially of a sequence according to SEQ ID NO: 15, SEQ ID NO: 21, and/or SEQ ID NO: 24 comprises a detectable label (e.g., a fluorescent moiety) and a quencher.

Computer-aided Diagnostics

In some embodiments, a computer-based analysis program is used to translate the raw data generated by the detection assay (e.g., raw data comprising an EGFRvIII Ct value, a total EGFR Ct value, a EGFRvIII dCt value, a total EGFR dCt value; e.g., raw data comprising an indication of the presence, absence, or the amount of EGFRvIII and/or the amount of total EGFR expression) into data of predictive value for a clinician. The clinician can access the predictive data using any suitable means. Thus, in some preferred embodiments, the present technology provides the further benefit that the clinician, who is not likely to be trained in genetics or molecular biology, need not understand the raw data. The data is presented directly to the clinician in its most useful form. The clinician is then able to utilize the information to optimize the care of the subject. The present technology contemplates any method capable of receiving, processing, and transmitting the information to and from laboratories conducting the assays, information providers, medical personnel, and subjects. For example, in some embodiments of the present technology, a sample is obtained from a subject and submitted to a profiling service (e.g., a clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves and directly send it to a profiling center. Where the sample comprises previously determined biological information, the information may be directly sent to the profiling service by the subject. Once received by the profiling service, the sample is processed and a profile is produced that is specific for the diagnostic or prognostic information desired for the subject. The profile data is then prepared in a format suitable for interpretation by a treating clinician. For example, rather than providing raw data, the prepared format may represent a diagnosis (e.g., of a cancer) or risk assessment (e.g., of a cancer) for the subject, along with recommendations for particular treatment options. The data may be displayed to the clinician by any suitable method. For example, in some embodiments, the profiling service generates a report that is printed for the clinician (e.g., at the point of care) or displayed to the clinician on a computer monitor. In some embodiments, the information is first analyzed at the point of care or at a regional facility. The raw data is then sent to a central processing facility for further analysis and/or to convert the raw data into information useful for a clinician or patient. The central processing facility provides the advantage of privacy (e.g., all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers. In some embodiments, the subject is able to access the data directly using the electronic communication system. The subject may chose further intervention or counseling based on the results. In some embodiments, the data is used for research use. For example, the data may be used to optimize the inclusion or elimination of markers as useful indicators of a particular condition associated with the disease.

Thus, in some embodiments, the technology described herein is associated with a programmable machine designed to perform a sequence of arithmetic or logical operations as provided by the methods described herein. For example, some embodiments of the technology are associated with (e.g., implemented in) computer software and/or computer hardware. In one aspect, the technology relates to a computer comprising a form of memory, an element for performing arithmetic and logical operations, and a processing element (e.g., a microprocessor) for executing a series of instructions (e.g., a method as provided herein) to read, manipulate, and store data. In some embodiments, a microprocessor is part of a system for determining the absence, presence, and/or amount of EGFRvIII and/or total EGFR expression (e.g., relative to an internal control); generating standard curves; determining a Ct value; calculating a dCt value, e.g., as described herein or as is known in the art.

In some embodiments, a microprocessor or computer uses the absence, presence, and/or amount of EGFRvIII and/or total EGFR expression (e.g., relative to an internal control) in an algorithm to predict a site of a cancer.

In some embodiments, a software or hardware component receives the results of multiple assays and determines a single value result to report to a user that indicates a cancer risk based on the results of the multiple assays (e.g., determining the absence, presence, and/or amount of EGFRvIII and/or total EGFR expression (e.g., relative to an internal control)). Related embodiments calculate a risk factor based on a mathematical combination (e.g., a weighted combination, a linear combination) of the results from multiple assays, e.g., determining the absence, presence, and/or amount of EGFRvIII and/or total EGFR expression (e.g., relative to an internal control). In some embodiments, the absence, presence, and/or amount of EGFRvIII and/or total EGFR expression (e.g., relative to an internal control) defines a dimension and may have values in a multidimensional space and the coordinate defined by the absence, presence, and/or amount of EGFRvIII and/or total EGFR expression (e.g., relative to an internal control) is a result, e.g., to report to a user, e.g., related to a cancer risk.

Some embodiments comprise a storage medium and memory components. Memory components (e.g., volatile and/or nonvolatile memory) find use in storing instructions (e.g., an embodiment of a process as provided herein) and/or data (e.g., a work piece such as the absence, presence, and/or amount of EGFRvIII and/or total EGFR expression (e.g., relative to an internal control), sequences, and statistical descriptions associated therewith). Some embodiments relate to systems also comprising one or more of a CPU, a graphics card, and a user interface (e.g., comprising an output device such as display and an input device such as a keyboard).

Programmable machines associated with the technology comprise conventional extant technologies and technologies in development or yet to be developed (e.g., a quantum computer, a chemical computer, a DNA computer, an optical computer, a spintronics based computer, etc.).

In some embodiments, the technology comprises a wired (e.g., metallic cable, fiber optic) or wireless transmission medium for transmitting data. For example, some embodiments relate to data transmission over a network (e.g., a local area network (LAN), a wide area network (WAN), an ad-hoc network, the internet, etc.). In some embodiments, programmable machines are present on such a network as peers and in some embodiments the programmable machines have a client/server relationship.

In some embodiments, data are stored on a computer-readable storage medium such as a hard disk, flash memory, optical media, a floppy disk, etc.

In some embodiments, the technology provided herein is associated with a plurality of programmable devices that operate in concert to perform a method as described herein. For example, in some embodiments, a plurality of computers (e.g., connected by a network) may work in parallel to collect and process data, e.g., in an implementation of cluster computing or grid computing or some other distributed computer architecture that relies on complete computers (with onboard CPUs, storage, power supplies, network interfaces, etc.) connected to a network (private, public, or the internet) by a conventional network interface, such as Ethernet, fiber optic, or by a wireless network technology.

For example, some embodiments provide a computer that includes a computer-readable medium. The embodiment includes a random access memory (RAM) coupled to a processor. The processor executes computer-executable program instructions stored in memory. Such processors may include a microprocessor, an ASIC, a state machine, or other processor, and can be any of a number of computer processors, such as processors from Intel Corporation of Santa Clara, Calif. and Motorola Corporation of Schaumburg, Ill. Such processors include, or may be in communication with, media, for example computer-readable media, which stores instructions that, when executed by the processor, cause the processor to perform the steps described herein.

Embodiments of computer-readable media include, but are not limited to, an electronic, optical, magnetic, or other storage or transmission device capable of providing a processor with computer-readable instructions. Other examples of suitable media include, but are not limited to, a floppy disk, CD-ROM, DVD, magnetic disk, memory chip, ROM, RAM, an ASIC, a configured processor, all optical media, all magnetic tape or other magnetic media, or any other medium from which a computer processor can read instructions. Also, various other forms of computer-readable media may transmit or carry instructions to a computer, including a router, private or public network, or other transmission device or channel, both wired and wireless. The instructions may comprise code from any suitable computer-programming language, including, for example, Swift, Objective C, C, C++, C#, Visual Basic, Java, Python, Perl, Ruby, Unix, and JavaScript. Computers are connected in some embodiments to a network. Computers may also include a number of external or internal devices such as a mouse, a CD-ROM, DVD, a keyboard, a display, or other input or output devices. Examples of computers are personal computers, digital assistants, personal digital assistants, cellular phones, mobile phones, smart phones, pagers, digital tablets, laptop computers, internet appliances, and other processor-based devices. In general, the computers related to aspects of the technology provided herein may be any type of processor-based platform that operates on any operating system, such as Microsoft Windows, Linux, UNIX, Mac OS X, BSD, etc., capable of supporting one or more programs comprising the technology provided herein. Some embodiments comprise a personal computer executing other application programs (e.g., applications). The applications can be contained in memory and can include, for example, a word processing application, a spreadsheet application, an email application, an instant messenger application, a presentation application, an Internet browser application, a calendar/organizer application, and any other application capable of being executed by a client device.

All such components, computers, and systems described herein as associated with the technology may be logical or virtual.

EXAMPLES

Example 1

Detection of Total EGFR mRNA and EGFRvIII mRNA in Cancer Samples

During the development of embodiments of the technology provided herein, experiments were conducted to test the detection of EGFRvIII mRNA and total EGFR mRNA in formalin-fixed, paraffin embedded (FFPE) glioblastoma myeloma (GBM) samples using novel primers and probes as described herein.

Methods

Preparation of RNA (FFPE) GBM specimens: Paraffin embedded (FFPE) glioblastoma myeloma (GBM) samples were processed from previous Phase I trials of the ABT-806 and ABT-414 therapeutics. One FFPE section was prepared from each of 21 GBM specimens examined in the experiments. Each FFPE section was scraped into a microfuge tube using a single-edge razor blade. A new blade was used for each sample. A FFPE section from a lung sample ("A549") known to express EGFR was scraped into a microfuge tube as a positive control (e.g., available at ATCC® CCL-185™). See, e.g., Giard et al (1973) "In vitro cultivation of human tumors: establishment of cell lines derived from a series of solid tumors" J. Natl. Cancer Inst. 51: 1417-1423.

The samples were identified by the following sample names: 1250, 1238, 1237, 1236, 1248, 793, 783, 782, 779, 1247, 630, 1246, 1242, 1243, 401, 402, 403, 302, 1251, 1252, and 1253.

The FFPE sections were processed for RNA extraction using the Qiagen RNeasy FFPE extraction kit according to the manufacturer's protocol (e.g., RNeasy FFPE Handbook, Qiagen). Deparaffinization solution (Qiagen RNeasy FFPE extraction kit) alone (without added FFPE tissue) was used as a negative control.

RNA was extracted from samples by adding 160 microliters of deparaffinization solution (Qiagen RNeasy FFPE extraction kit) to the tubes containing the FFPE material. The samples were vortexed vigorously for 10 seconds and then centrifuged briefly to collect the sample at the bottom of the tube. Next, the samples were incubated at 56° C. for 3 minutes and then allowed to cool at room temperature. A 150-microliter volume of Buffer PKD (Qiagen RNeasy FFPE extraction kit) was added, the samples were mixed by vortexing, and then the samples were centrifuged for 1 minute at 11,000×g. After centrifugation, 10 microliters of proteinase K (Qiagen RNeasy FFPE extraction kit) were added to the lower, clear phase and the samples were mixed gently by pipetting up and down. Then, samples were first incubated at 56° C. for 15 minutes, and then samples were incubated at 80° C. for 15 minutes. The lower, uncolored phase of each sample was transferred into a new 2-milliliter microcentrifuge tube and incubated on ice for 3 minutes. The samples were then centrifuged for 15 minutes at 20,000×g. After centrifugation, the supernatant was transferred to a new microcentrifuge tube without disturbing the pellet.

Next, 15 microliters of DNase Booster Buffer (Qiagen RNeasy FFPE extraction kit) and 10 microliters of RNase-free DNase I stock solution (Qiagen RNeasy FFPE extraction kit) were added to the supernatant and the samples were mixed by inverting the tubes. The samples were then centrifuged to collect the contents at the bottoms of the tubes; samples were incubated at room temperature for 15 minutes. After incubation on ice, 320 microliters of Buffer RBC (Qiagen RNeasy FFPE extraction kit) were added to adjust binding conditions and the lysates were mixed thoroughly. A 720-microliter volume of ethanol (100%) was added to each sample and the samples were mixed well by pipetting. After mixing, 700 microliters of the sample were transferred (including any precipitate that may have formed) to an RNeasy MinElute spin column (Qiagen RNeasy FFPE extraction kit) placed in a 2-milliliter collection tube. The lid was closed gently and the tubes were centrifuged for 15 seconds at 8000×g or more (greater than 10,000 rpm). The flow-through was discarded. The centrifugation was repeated until the entire sample had passed through the RNeasy MinElute spin column. Next, 500 microliters of Buffer RPE (Qiagen RNeasy FFPE extraction kit) was added to the RNeasy MinElute spin column. The lid was closed gently and the samples were centrifuged for 15 seconds at 8000×g or more (greater than 10,000 rpm). The flow-through was discarded. Another volume of 500 microliters of Buffer RPE (Qiagen RNeasy FFPE extraction kit) were added to the RNeasy MinElute spin column. The lid was closed gently and the samples were centrifuged for 2 minutes at 8000×g or more (greater than 10,000 rpm) to wash the spin column membrane. The flow-through was discarded.

After centrifugation, each RNeasy MinElute spin column was carefully removed from the collection tube and placed in a new 2-milliliter collection tube. The lid of each spin column was opened and the tubes were centrifuged at full speed for 5 minutes. The collection tubes holding the flow-through were discarded. The RNeasy MinElute spin column was next placed in a new 1.5-milliliter collection tube. A volume of 30 microliters of RNase-free water was added directly to the spin column membrane. The lid was closed gently and the sample was centrifuged for 1 minute at full speed to elute and collect the RNA.

Testing GBM samples using EGFRvIII assay: Two reaction mixtures (e.g., Master Mixes) were prepared—Master Mix A comprised the nominal EGFRvIII reverse primer EGvIII-A and Master Mix B comprised a shorter, alternative EGFRvIII reverse primer, EGFRvIII Rev_D designed for testing in embodiments of methods described herein. First, a Common Master Mix (CMM) was prepared and then Master Mix A and Master Mix B were prepared using the CMM (see, e.g., TABLE 6).

The CMM comprised primers and probes for detecting total EGFR (e.g., the primers EGwti29_−47 to−25 and EGwti29_+23to−3 and the probe EGi29_−24to−11pNED) and comprised the forward primer and probe for detecting EGFRvIII (e.g., the primer EGvIIIi1_−58to−41 and the probe EGvIIIi1_−39 to−21 pFAM) when paired with one of the reverse primers in the Master Mix A or Master Mix B (EGvIII-A and EGFRvIII Rev_D, respectively). See FIG. 2 for locations of total EGFR primers and probe and EGFRvIII primers and probe.

TABLE 6

Exemplary amplification reaction mixtures

| component | stock solution conc. | unit | component in reaction final Conc. | unit | total rxn volume (µL) | component volume (µL) per rxn | number of rxns | component final volume (µL) |
|---|---|---|---|---|---|---|---|---|
| Common Master Mix (CMM) | | | | | | | | |
| 5× EZ Buffer | 5 | × | 1.000 | × | 50 | 10.000 | 104 | 1040.00 |
| dNTP Mix | 25 | mM | 0.488 | mM | 50 | 0.975 | 104 | 101.40 |
| ROX Dye | 2 | µM | 0.029 | µM | 50 | 0.725 | 104 | 75.40 |
| Aptamer | 24.82 | µM | 0.200 | µM | 50 | 0.403 | 104 | 41.90 |
| EGwti29_−47to−25 | 50.79 | µM | 0.050 | µM | 50 | 0.049 | 104 | 5.12 |
| EGi29_−24to−11pNED | 42.85 | µM | 0.600 | µM | 50 | 0.700 | 104 | 72.81 |
| EGwti29_+23to−3 | 55.17 | µM | 0.075 | µM | 50 | 0.068 | 104 | 7.07 |
| EGvIIIi1_−58to−41 | 55.34 | µM | 0.063 | µM | 50 | 0.056 | 104 | 5.87 |
| EGvIIIi1_−39to−21pFAM | 32.22 | µM | 0.188 | µM | 50 | 0.291 | 104 | 30.26 |
| bActl1_−53to−33 | 53.28 | µM | 0.100 | µM | 50 | 0.094 | 104 | 9.76 |
| bActl1_+17to−5 | 53.24 | µM | 0.300 | µM | 50 | 0.282 | 104 | 29.30 |
| bActl1_−29to−10pCY5 | 52.86 | µM | 0.300 | µM | 50 | 0.284 | 104 | 29.51 |

TABLE 6-continued

Exemplary amplification reaction mixtures

| component | stock solution conc. | unit | component in reaction final Conc. | unit | total rxn volume (μL) | component volume (μL) per rxn | number of rxns | component final volume (μL) |
|---|---|---|---|---|---|---|---|---|
| MnCl$_2$ | 30 | mM | 3.000 | mM | 50 | 5.000 | 104 | 520.00 |
| rTth | 3.2 | U/μL | 0.200 | U/μL | 50 | 3.125 | 104 | 325.00 |
| H$_2$O | N/A | N/A | N/A | N/A | 50 | 0.948 | 104 | 98.59 |
| | | | | | | | | Total 2392.00 |
| | | | Master Mix A | | | | | |
| CMM | N/A | N/A | N/A | N/A | 50 | 23.000 | 51 | 1173.00 |
| EGvIII-A | 53.44 | μM | 0.188 | μM | 50 | 0.175 | 51 | 8.95 |
| H$_2$O | N/A | N/A | N/A | N/A | 50 | 1.825 | 51 | 93.05 |
| | | | Master Mix B | | | | | |
| CMM | N/A | N/A | N/A | N/A | 50 | 23.000 | 51 | 1173.00 |
| EGFRvIII Rev_D | 56.89 | μM | 0.423 | μM | 50 | 0.372 | 51 | 18.96 |
| H$_2$O | N/A | N/A | N/A | N/A | 50 | 1.628 | 51 | 83.04 |

In TABLE 6, probes with names ending in "NED", "FAM", and "CY5" comprised a NED, FAM, and CY5 fluorescent moiety, respectively.

The RNA eluates prepared above (GBM specimens), the positive EGFR control (A549), and the negative control were diluted in water (e.g., 2 microliters of sample in a 25 microliter volume). The 25-microliter samples were added to 25 microliters of a Master Mix in each well of a 96-well plate. Two replicates of each sample were tested. In addition, two replicates of a circular EGFR control plasmid (see below) were added as a PCR positive control. The plate was sealed with an optical adhesive cover, centrifuged at 3000 rpm for 1 minute, placed in an ABI 7500 RtPCR System (m2000rt), and thermocycled according to the following program:

| Stage | Cycles | Step | Temp (C.) | Time (min:sec) |
|---|---|---|---|---|
| 1 | 1 | 1 | 62 | 30:00 |
| 2 | 4 | 1 | 92 | 00:30 |
| | | 2 | 60 | 00:30 (1-s autoincrement) |
| 3 | 50 | 1 | 92 | 00:30 |
| | | 2 | 62 | 00:30 (1-s autoincrement) |
| | | 3 | 58 (read*) | 00:40 |

*in the "read" steps, the fluors FAM, NED, Cy5, and ROX are monitored.

Data were analyzed using software for generating and analyzing real-time PCR data (e.g., plotting data, data reduction, determining Ct values, etc.). Threshold values were FAM=0.100, NED=0.075, and Cy5=0.100. Results were tabulated and analyzed using Microsoft Excel.

Concentration determination for GBM specimens: The RNA concentrations of GBM samples were determined by measuring absorbance of the samples at 260 nanometers (using a Nanodrop spectrophotometer) and measuring absorbance of the samples at 280 nanometers, then computing the ratio of the absorbance at 260 nanometers to the absorbance at 280 nanometers ($A_{260}/A_{280}$). For all samples, 2 microliters of eluate were added to the NanoDrop in replicates of 2. The concentrations were averaged to estimate the final concentration of RNA in nanograms per microliter (ng/μl).

Results

Real-time PCR data were collected and Ct values were determined for total EGFR mRNA, EGFRvIII mRNA, and the endogenous control ACTB mRNA. Data were collected from assays of reaction mixtures comprising the nominal EGFRvIII reverse primer EGvIII-A (see, e.g., FIG. 5, FIG. 7) and from assays of reaction mixtures comprising the alternate EGFRvIII reverse primer EGFRvIII Rev_D tested herein (see, e.g., FIG. 6, FIG. 8).

Delta Ct values (dCt) for total EGFR mRNA and EGFRvIII mRNA were calculated by subtracting the total EGFR mRNA Ct value from the endogenous control ACTB mRNA Ct value (e.g., "actin-EGFR") and by subtracting the EGFRvIII mRNA Ct value from the endogenous control ACTB mRNA Ct value (e.g., "actin-EGFRvIII), respectively (see, e.g., FIG. 5, FIG. 6, FIG. 7, FIG. 8). Accordingly, the dCt values provide a relative measure of gene expression using the expression of the endogenous control ACTB mRNA as a baseline value.

Figure 5:
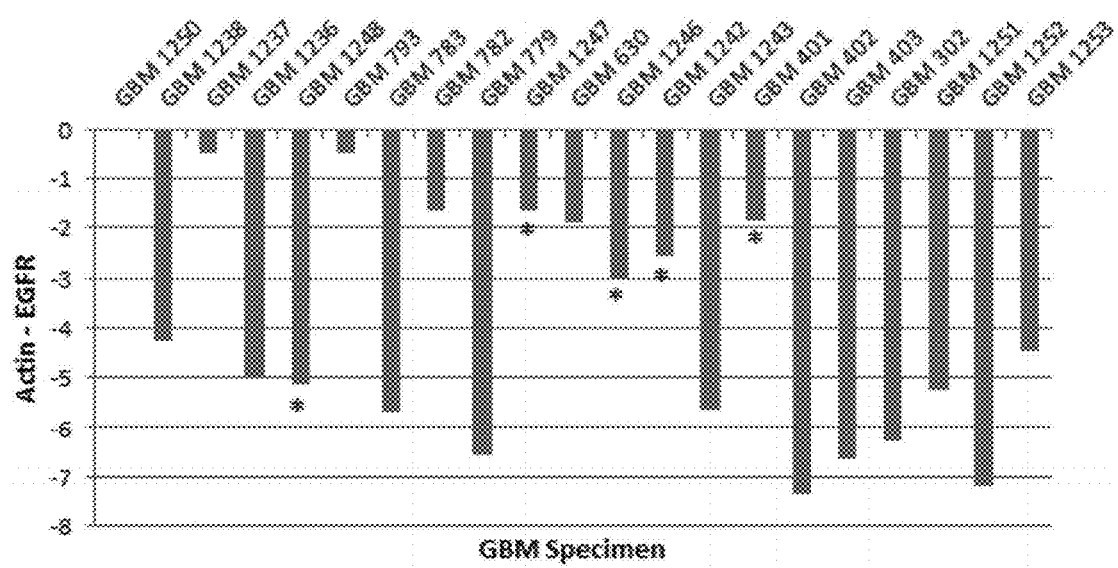
FIG. 5 is a plot showing a comparison of total EGFR dCt values (beta-actin Ct-EGFR Ct) for GBM FFPE samples. Samples in which EGFRvIII was detected are labeled with an asterisk. The EGFRvIII assay indicated that EGFRvIII mRNA was detected in 5 of the 21 samples.
Figure 6:
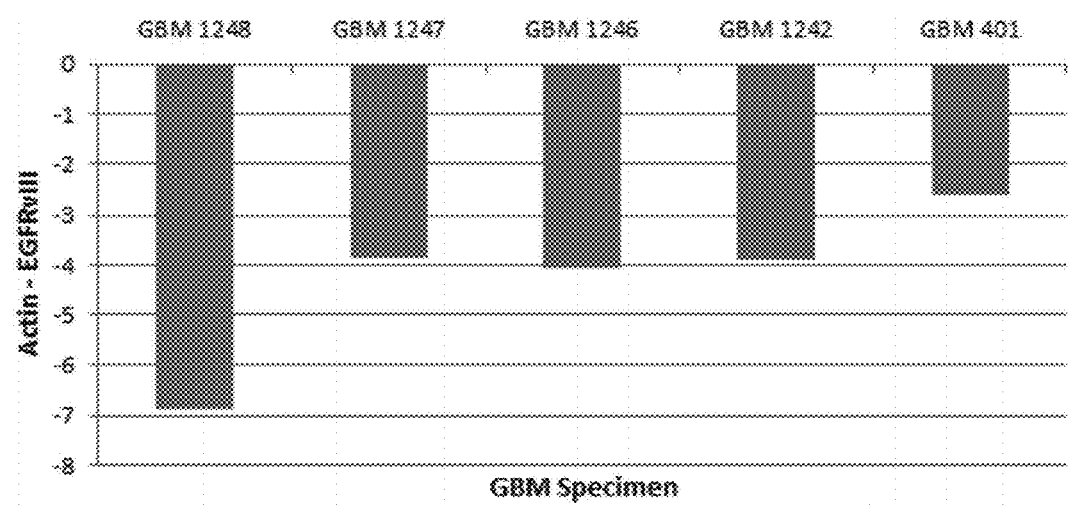
FIG. 6 is a plot showing a comparison of EGFRvIII dCt values (beta-actin Ct-EGFR Ct) for GBM FFPE samples that had detectable EGFRvIII expression. The relative EGFRvIII expression (beta-actin Ct-EGFRvIII Ct) ranged from 2.59 (e.g., "high" expression) to −6.89 (e.g., "low" expression).
Figure 7A:
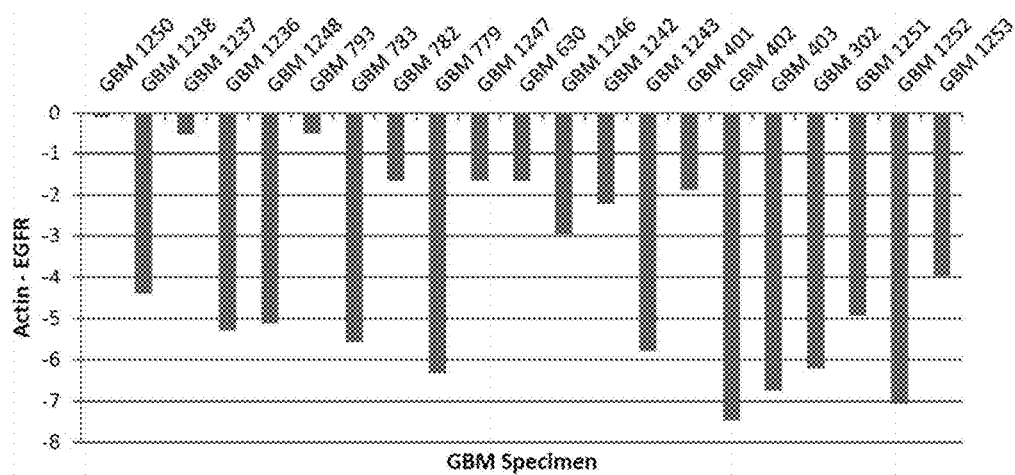
FIGS. 7A and 7b are a series of plots showing detection of total EGFR mRNA relative to the beta-actin control using the total EGFR primers EGwti29_−47to−25 and EGwti29_+23to−3 and the total EGFR probe EGi29_−24to−11pNED.
Figure 7B:
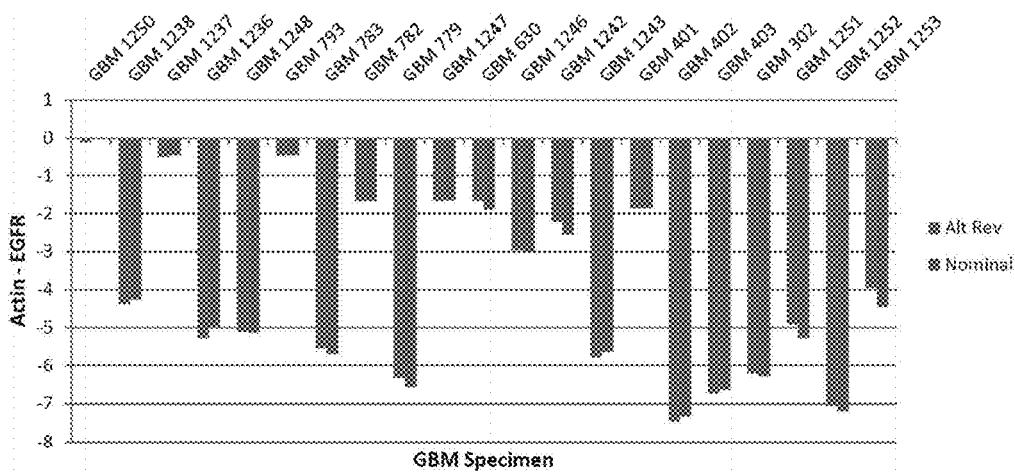

The dCt values for the amounts of total EGFR mRNA in the GBM samples ranged from approximately 0 (zero), indicating "high" expression, to approximately −7 or −8 (negative 7 or negative 8), indicating "low expression" (see, e.g., FIG. 5, FIG. 7). The data collected from experiments measuring total EGFR mRNA in the presence of the nominal EGFRvIII reverse primer EGvIII-A (see, e.g., FIG. 5) and from experiments measuring total EGFR mRNA in the presence of the alternate EGFRvIII reverse primer EGFRvIII Rev_D (see, e.g., FIG. 7A) were similar (see, e.g., FIG. 7B).

Expression of EGFRvIII mRNA was detected in five of the samples (GBM 1248, GBM 1247, GBM 1246, GBM 1242, and GBM 401; see, e.g., asterisked ("*") data in FIG. 5). Expression of EGFRvIII mRNA in these samples ranged from approximately −2 or −3 (negative 2 or negative 3) to approximately −6 or −7 (negative 6 or negative 7) (see, e.g., FIG. 6).

In sum, the real-time EGFRvIII assay indicated that 5 of the 21 samples were positive for EGFRvIII mRNA. The relative total EGFR expression (actin Ct-EGFR Ct) ranged from 0.00 (high expression) to −7.34 (low expression). Total RNA yields for all tested GBM samples ranged from 6.3 ng/μl to 237.3 ng/μl.

Figure 8A:
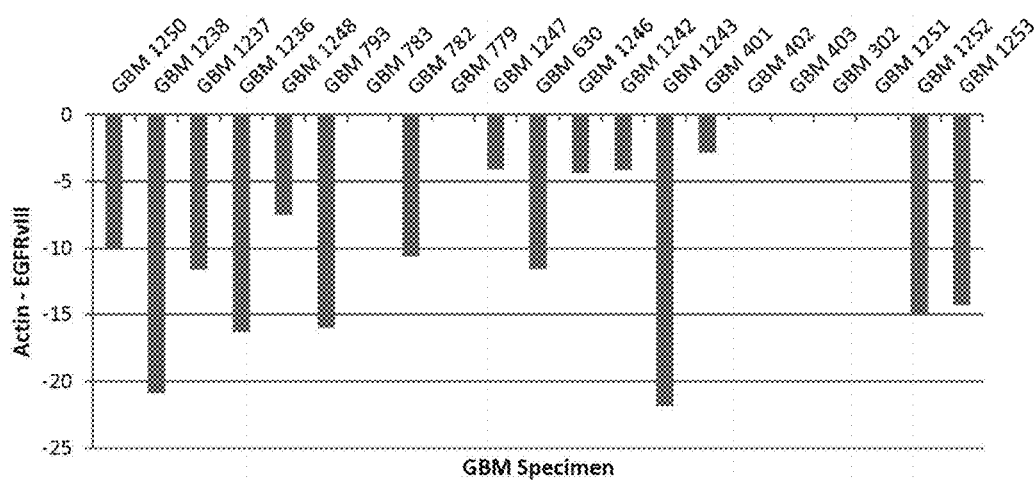
FIGS. 8A and 8B are a series of plots showing detection of EGFRvIII mRNA relative to the beta-actin control.
Figure 8B:
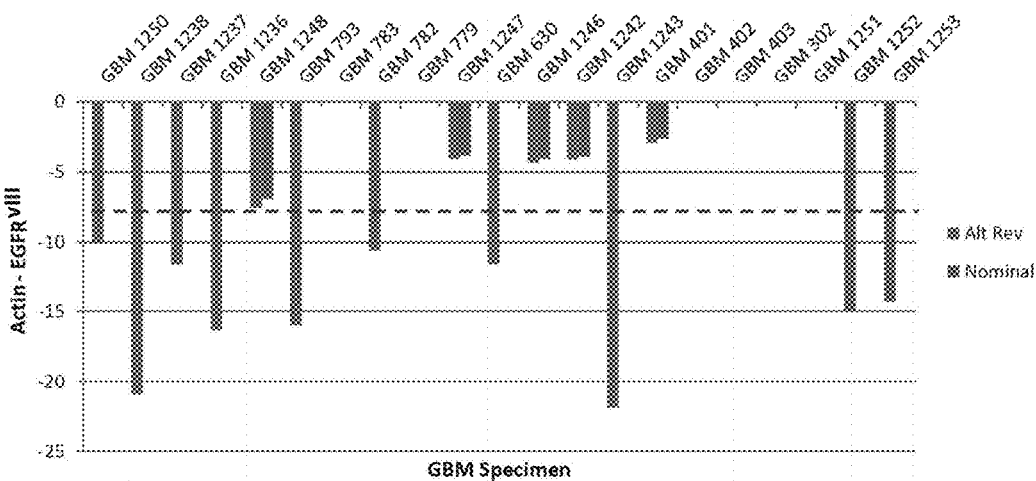

For the five samples in which expression of EGFRvIII mRNA was detected using the nominal reverse primer (see, e.g., FIG. 5, FIG. 6), similar expression of EGFRvIII mRNA was detected using the novel, alternate reverse primer EGFRvIII Rev_D developed for the assays described herein (see, e.g., FIG. 8B, samples GBM 1248, GBM 1247, GBM 1246, GBM 1242, and GBM 401).

In addition, several more specimens were detected to have low-level EGFRvIII signals using the alternative EGFRvIII reverse primer EGFRvIII Rev_D (see, e.g., FIG. 8). However, due to the high Ct and inefficient reaction kinetics (e.g., as determined by the relative reaction efficiency value MR) for these particular sample assays, it appeared that these data were non-specific and would therefore be screened out by other filters.

Figure 9:
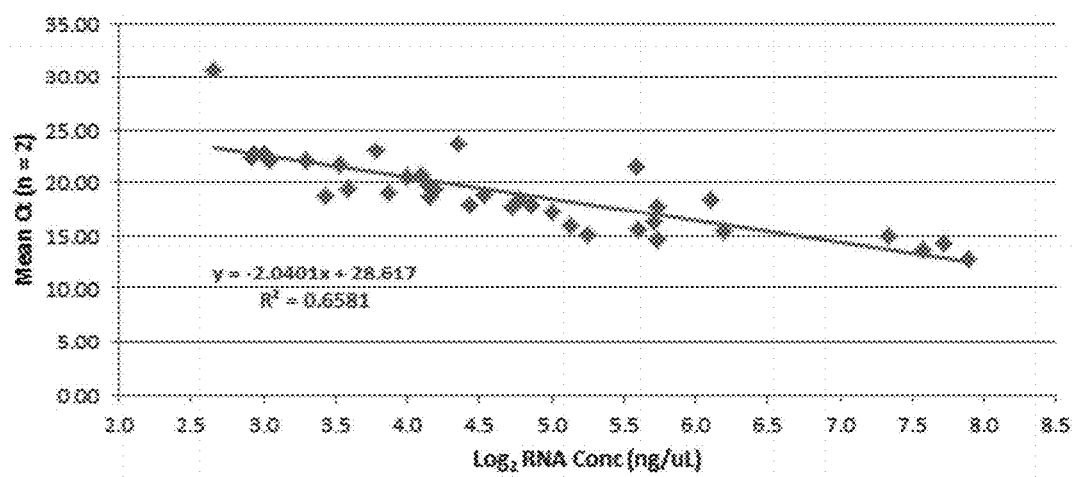
FIG. 9 is a plot showing the linear correlation of the total concentration of mRNA isolated from the GBM samples (expressed as log 2) with the mean beta-actin Ct (mean calculated from two independent samples). The RNA yields for all tested GBM samples ranged from 6.3 nanograms per microliter to 237.3 nanograms per microliter.

Finally, experiments were conducted in which the concentration of total RNA extracted from each GBM sample was correlated with the endogenous control ACTB mRNA Ct value to assess the endogenous control ACTB mRNA Ct value as an indication of total RNA concentration in the samples (see, e.g., FIG. 9). The mean Ct from duplicate determinations of ACTB Ct were plotted against the log 2 of the measured total RNA concentration (e.g., by NanoDrop analysis of $A_{260}/A_{280}$) (see, e.g., FIG. 9). The data indicated an approximately linear relationship between the ACTB Ct and the log 2 of the RNA concentration (see, e.g., FIG. 9).

Example 2

Positive Controls

Figure 10:
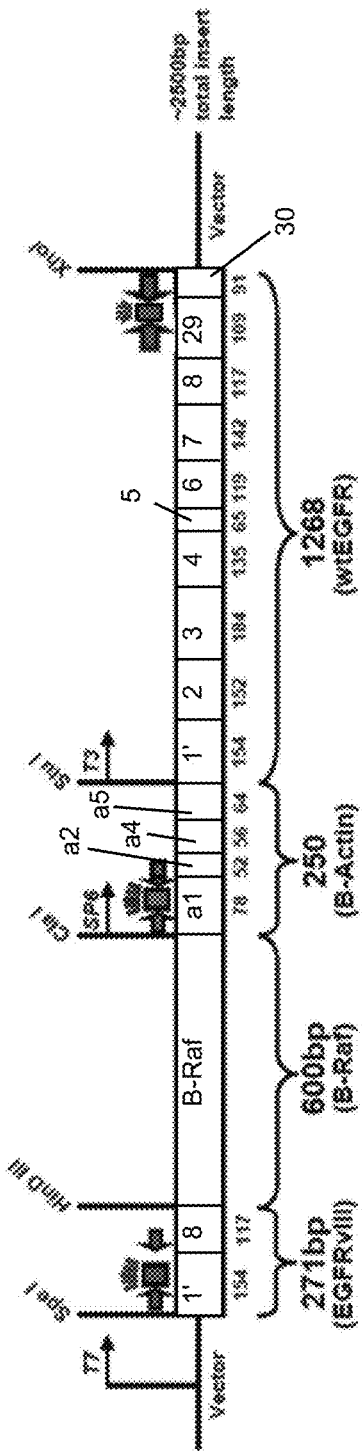
FIG. 10 is a schematic drawing of the pJW02 plasmid shown in linear form. The plasmid pJW02 comprises the EGFRvIII exon 1/exon 8 junction, the total EGFR exon 29/exon 30 junction that is present in both wild-type EGFR mRNA and EGFRvIII mRNA, and the beta-actin exon 1/exon 2 junction, and thus serves as a positive control for all three targets.

During the development of embodiments of the technology provided herein, experiments were conducted to assess the linear response of real-time PCR assays of a positive control plasmid comprising EGFRvIII, EGFR, and ACTB nucleotide sequences. In particular, a control plasmid (pJW02) was constructed to comprise the EGFRvIII exon 1/exon 2 junction, the total EGFR exon 29/exon 30 junction, and the ACTB exon 1/exon 2 junction (see, e.g., FIG. 10).

Methods

A reaction mixture (Master Mix) was prepared according to TABLE 7:

Circular pJW02 plasmid was serially diluted in 2-fold increments from 10 nanograms per reaction to approximately $1.86 \times 10^{-8}$ nanograms per reaction to create 31 dilution levels. Plasmid copy number ranged from over $1 \times 10^9$ copies per reaction to approximately 1 copy per reaction. 25 microliters of template was added to 25 microliters of Master Mix in each well of a 96-well plate. Three independent replicates of each dilution level were tested. Three replicates of $H_2O$ were also tested as a negative ("no target") control. The plate was sealed with an optical adhesive cover, centrifuged at 3000 rpm for 1 minute, placed in an ABI 7500 RtPCR System, and thermocycled according to the following program:

| Stage | Cycles | Step | Temp (C.) | Time (min:sec) |
|---|---|---|---|---|
| 1 | 1 | 1 | 62 | 30:00 |
| 2 | 4 | 1 | 92 | 00:30 |
|   |   | 2 | 60 | 00:30 (1-s autoincrement) |
| 3 | 50 | 1 | 92 | 00:30 |
|   |   | 2 | 62 | 00:30 (1-s autoincrement) |
|   |   | 3 | 58 (read*) | 00:40 |

*in the "read" steps, the fluors FAM, NED, Cy5, and ROX are monitored.

Data were analyzed using software for generating and analyzing real-time PCR data (e.g., plotting data, data reduction, determining Ct values, etc.). Threshold values for FAM=0.100, NED=0.075, and Cy5=0.100. Results were tabulated and analyzed in Microsoft Excel.

Results

Figure 11:
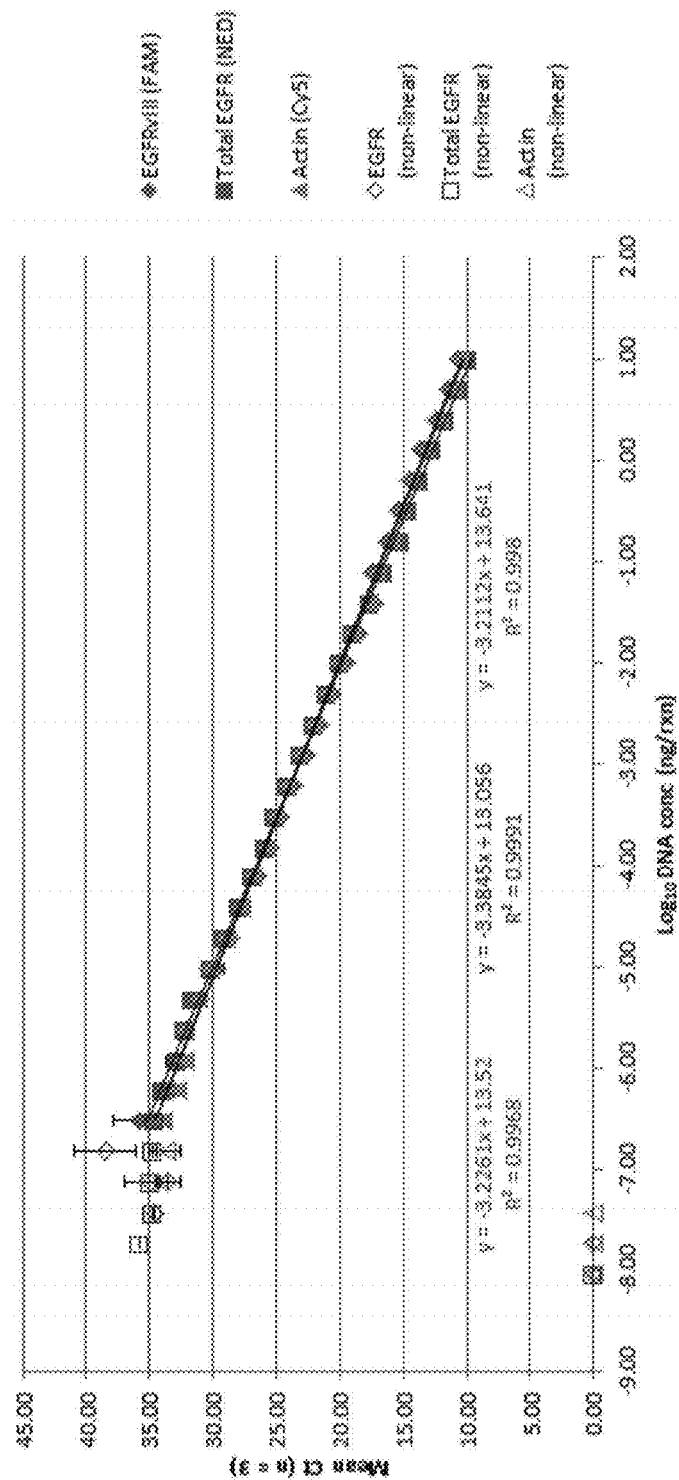
FIG. 11 is a plot showing the linear correlation of mean Ct to the concentration of EGFRvIII (diamonds), total EGFR (squares), and beta-actin (triangles) on the pJW02 control plasmid (expressed as login of concentration in nanograms per reaction). $R^2$ correlation coefficients are above 0.99 for all three targets. Three independent experiments were performed at each DNA concentration for each target.

The data collected indicated that the positive control plasmid (pJW02) provides adequate linearity for all three targets (EGFRvIII, total EGFR, and ACTB; see, e.g., FIG. 11, diamonds, squares, and triangles, respectively, indicating EGFRvIII, total EGFR, and ACTB mRNA) across a wide range of Ct values (see, e.g., FIG. 11). The linear range is over 7.5 logs (e.g., from $1.00 \log_{10}$ to $-6.58 \log_{10}$), which corresponds to a range of 10 nanograms to 0.3 femtograms of plasmid per reaction. Data points from samples that provided less than 100% detection for all three targets were

TABLE 7

Positive control Master Mix

| component | stock solution conc. | unit | component in reaction final conc. | unit | total rxn volume (µL) | component volume (µL) per rxn | number of rxns | component final volume (µL) |
|---|---|---|---|---|---|---|---|---|
| 5× EZ Buffer | 5 | × | 1.000 | × | 50 | 10.000 | 105 | 1050.00 |
| dNTP Mix | 25 | mM | 0.488 | mM | 50 | 0.975 | 105 | 102.38 |
| Rox Dye | 2 | µM | 0.029 | µM | 50 | 0.725 | 105 | 76.13 |
| Aptamer | 24.82 | µM | 0.200 | µM | 50 | 0.403 | 105 | 42.30 |
| EGwti29__-47to-25 | 50.79 | µM | 0.050 | µM | 50 | 0.049 | 105 | 5.17 |
| EGwti29__+23to-3 | 55.17 | µM | 0.075 | µM | 50 | 0.068 | 105 | 7.14 |
| EGi29__-24to-11pNED | 49.83 | µM | 0.600 | µM | 50 | 0.602 | 105 | 63.21 |
| EGvIIIi1__-58to-41 | 55.34 | µM | 0.063 | µM | 50 | 0.056 | 105 | 5.93 |
| EGvIII-A | 53.44 | µM | 0.188 | µM | 50 | 0.175 | 105 | 18.42 |
| EGvIIIi1__-39to-21pFAM | 32.22 | µM | 0.188 | µM | 50 | 0.291 | 105 | 30.55 |
| bActl1__-53to-33 | 53.28 | µM | 0.100 | µM | 50 | 0.094 | 105 | 9.85 |
| bActl1__+17to-5 | 53.24 | µM | 0.300 | µM | 50 | 0.282 | 105 | 29.58 |
| bActl1__-29to-10pCY5 | 55.95 | µM | 0.300 | µM | 50 | 0.268 | 105 | 28.15 |
| MnCl$_2$ | 30 | mM | 3.000 | mM | 50 | 5.000 | 105 | 525.00 |
| rTth | 3.2 | U/µL | 0.200 | U/µL | 50 | 3.125 | 105 | 328.13 |
| H$_2$O | N/A | N/A | N/A | N/A | 50 | 2.886 | 105 | 303.06 |

Total 2625 discarded (open symbols, FIG. 11). These samples all comprised the most dilute concentrations of RNA.

Example 3

Comparison of Internal Controls

Figure 12:
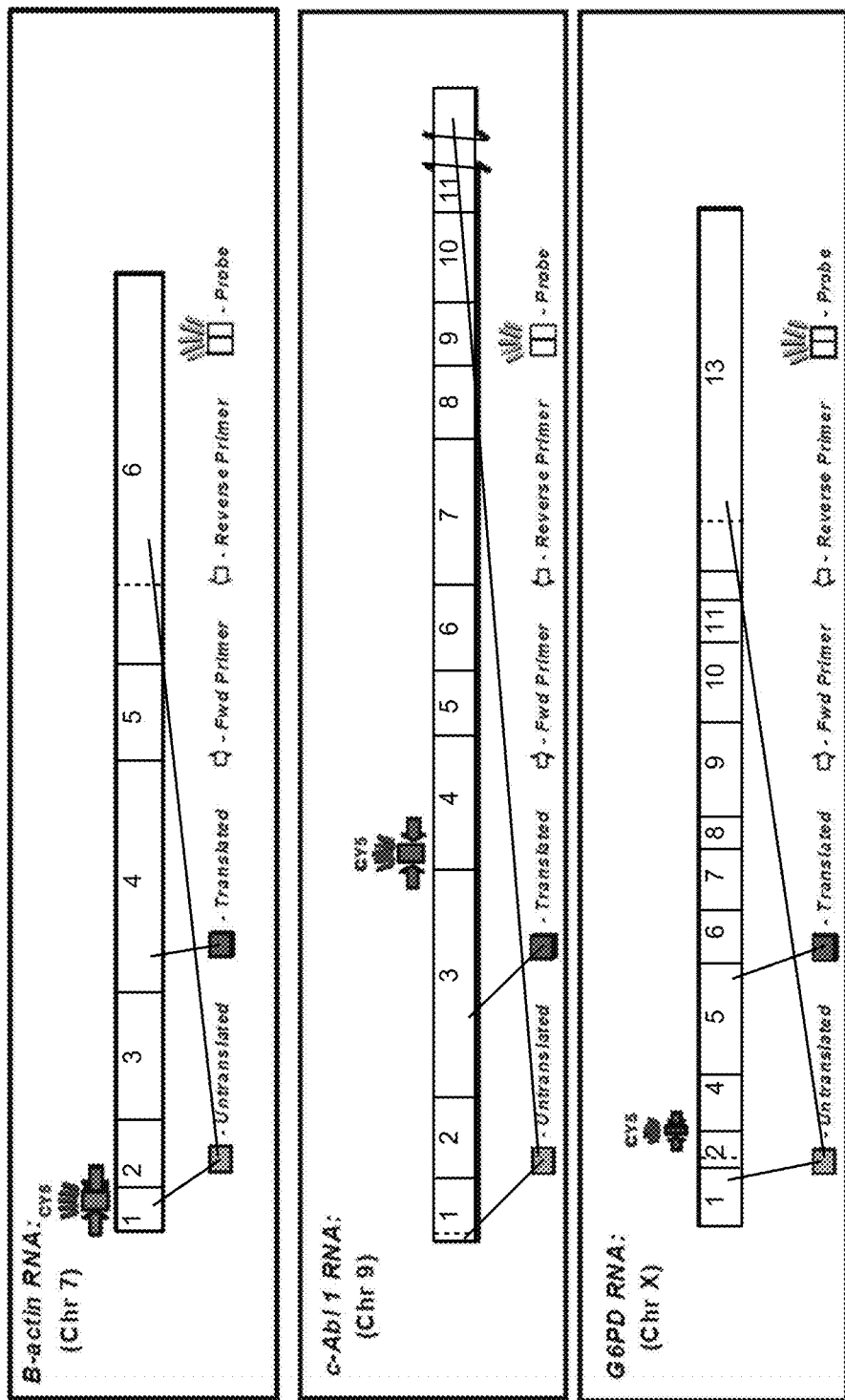
FIG. 12 is a schematic of internal controls showing relative primer and probe locations (e.g., binding site, sequence, and/or complementary sequence). Only one isoform is shown for each mRNA target, but primer and probe sets target all isoform variants.

During the development of embodiments of the technology provided herein, experiments were conducted to evaluate internal controls for use in embodiments of the total EGFR and EGFRvIII assays described herein. In particular, mRNAs for three internal controls were selected for this study: beta-actin (ACTB), c-Abl 1 (ABL), and glucose 6 phosphate dehydrogenase (G6PD) (see, e.g., FIG. 12). ACTB resides on chromosome 7 with EGFR; in contrast, neither ABL nor G6PD resides on chromosome 7. Tests were conducted to compare the performance of the internal controls for the EGFR assay and to evaluate the use of an internal control that resides on the same chromosome as EGFR. It was contemplated that the ACTB control would have higher expression levels in tumors with chromosome 7 duplications, but not in tumors with EGFR focal amplification. The ACTB mRNA sequence is available at NCBI accession number NM_001101; the ABL mRNA sequence is available at NCBI accession number NM_005157; and the G6PD mRNA sequence is available at NCBI accession number NM_001042351, each incorporated by reference herein.

Methods

Three amplification Master Mixes were made, each of which comprised dNTP, aptamer, buffer, $MnCl_2$, recombinant Tth polymerase, ROX passive reference dye, the EGFR wild-type primers and probes in TABLE 8, and the EGFRvIII primers and probes in TABLE 7.

TABLE 8

Primers and probes used in the Master Mix

| oligo name | oligo type | stock concentration (µM) |
|---|---|---|
| EGvIIIi1_−58to−41 | primer | 55.75 |
| EGvIII-A | primer | 53.61 |
| EGvIIIi1_−39to−21pFAM | probe | 54.92 |
| EGwti7_−28to−9 | primer | 53.48 |
| EGv3i1_+36to+18 | primer | 52.95 |
| EGFRwti7_−7to+8 NED MGB | probe | 50.29 |
| bActI1_−53to−33 | primer | 52.58 |
| bActI1_−29to−10pCY5 | probe | 52.34 |
| bActI1_+17to−5 | primer | 54.62 |
| ABLi3_fwd−21to+2 | primer | 50.40 |
| ABLi3+65to+41 | primer | 43.84 |
| ABLi3+9to+33pCY5 | probe | 36.76 |
| G6PDl2_FWD−50TO−28 | primer | 54.45 |
| G6PDi2_rev−37to−12 | primer | 45.82 |
| G6PDv1_fwd346to367 Cy5 | probe | 53.55 |

Figure 13:
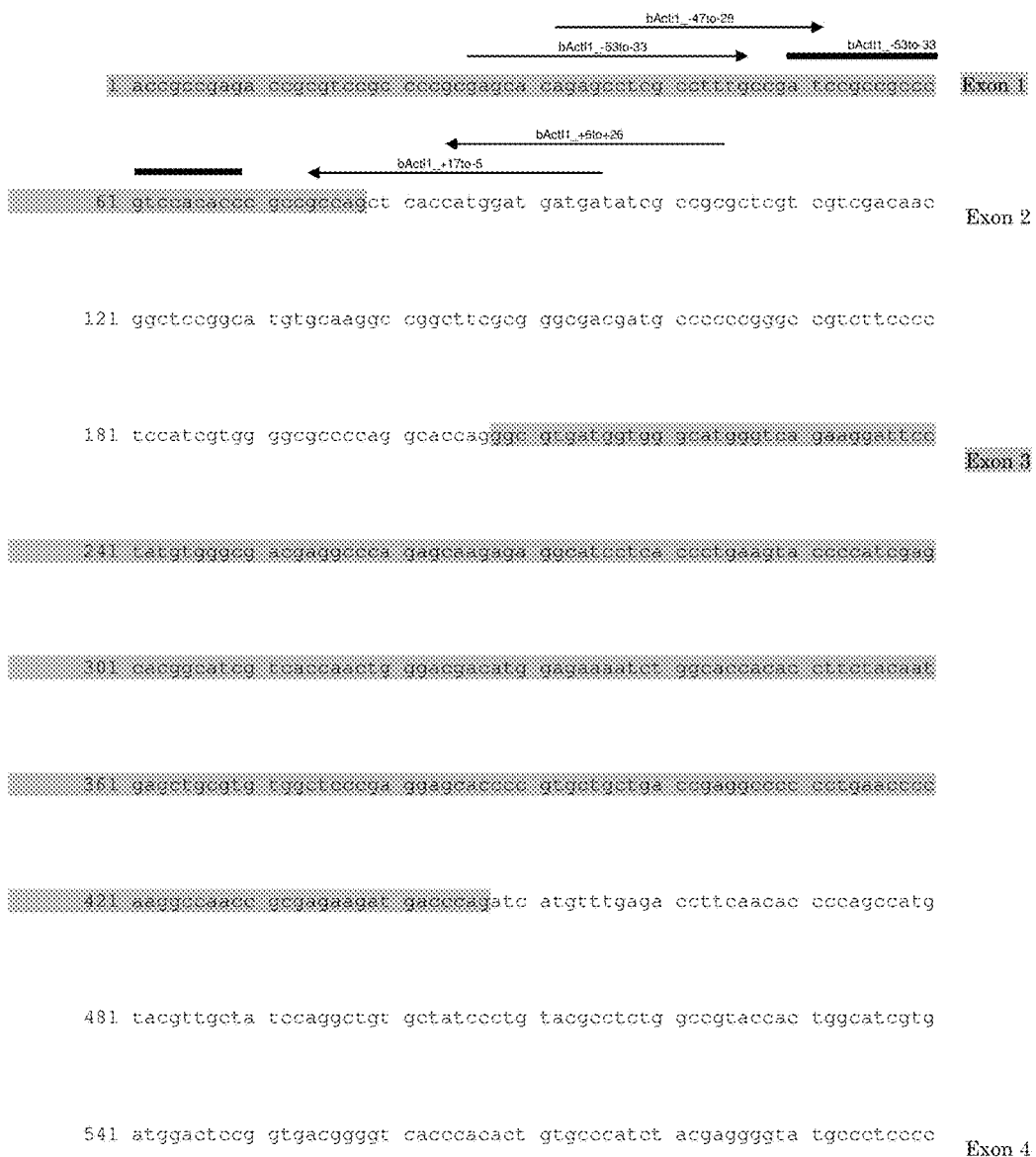
FIG. 13 shows the sequence of the mRNA product transcribed from the *Homo sapiens* beta-actin (ACTB) gene. The locations where some embodiments of detection primers (arrows) (or their reverse complements) and probes (thick lines) (or their reverse complements) hybridize to the ACTB mRNA or to a cDNA transcribed from the mRNA are indicated. Primer and probe sequences are provided in Table 5. Exons are indicated along the right side of the sequence.
Figure 14:
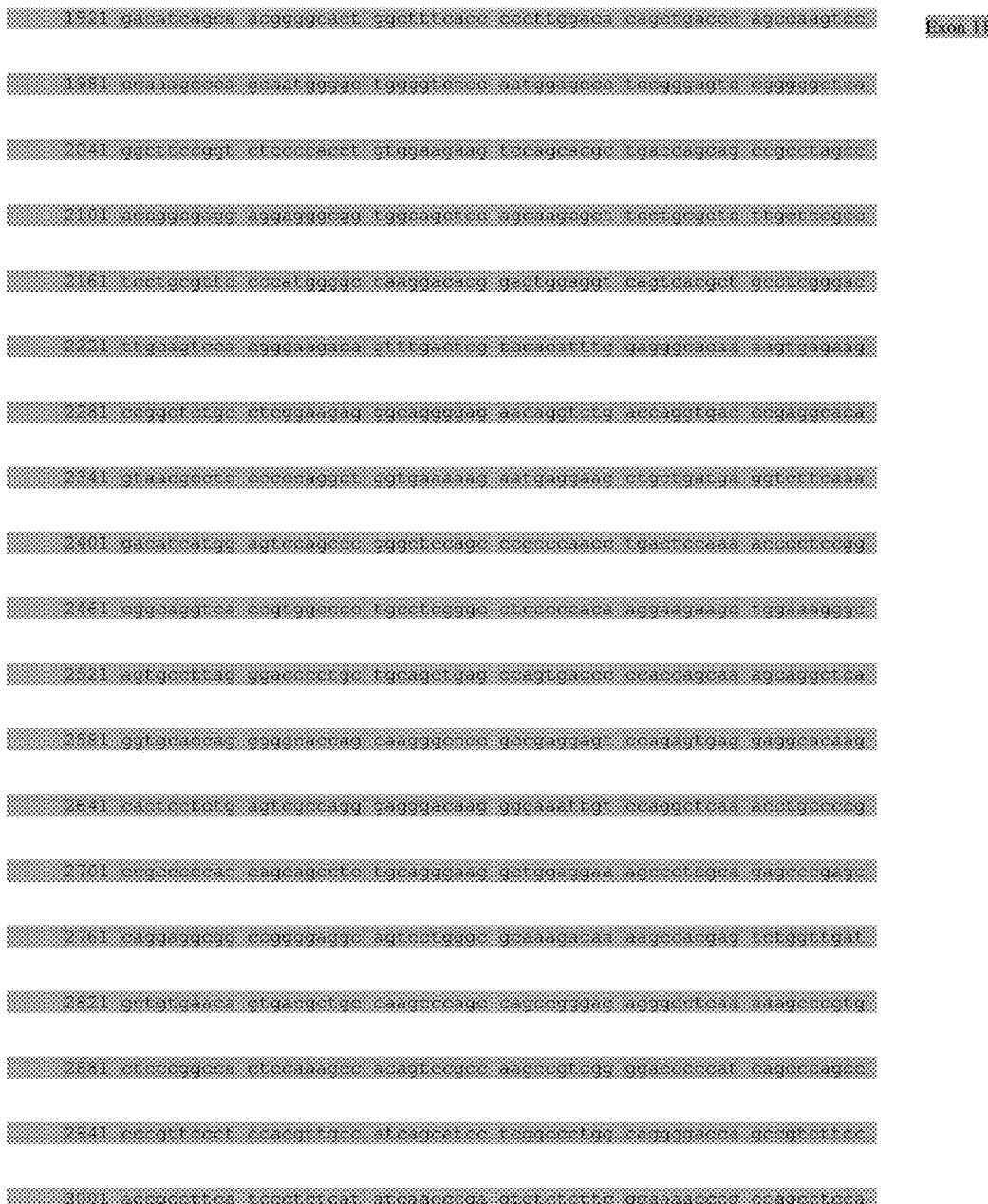
FIG. 14 shows the sequence of the mRNA product transcribed from the *Homo sapiens* c-abl oncogene (ABL). The locations where some embodiments of detection primers (arrows) (or their reverse complements) and probes (thick lines) (or their reverse complements) hybridize to the ABL mRNA or to a cDNA transcribed from the mRNA are indicated. Primer and probe sequences are provided in Table 5. Exons are indicated along the right side of the sequence.
Figure 14:
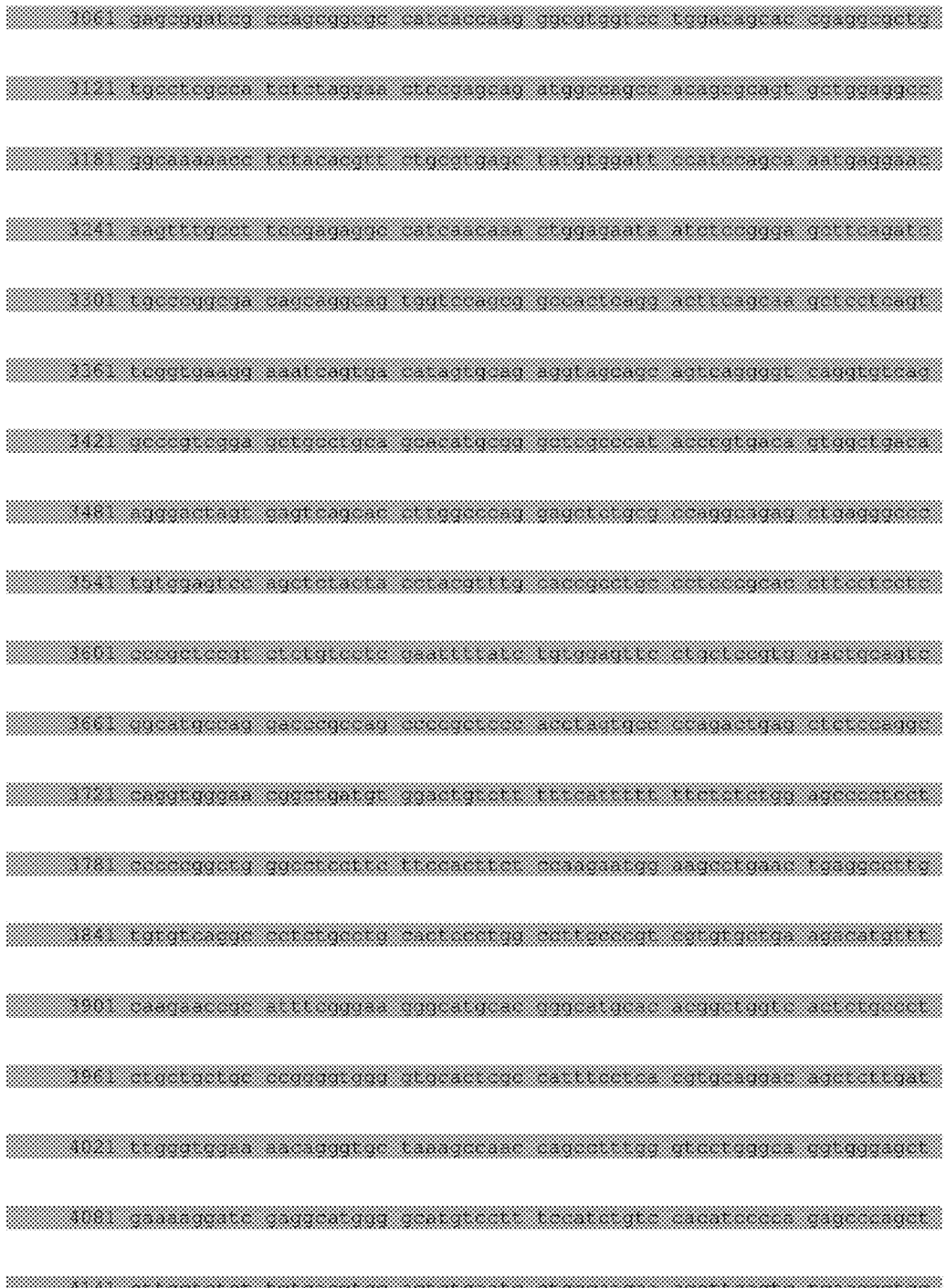
Figure 14:
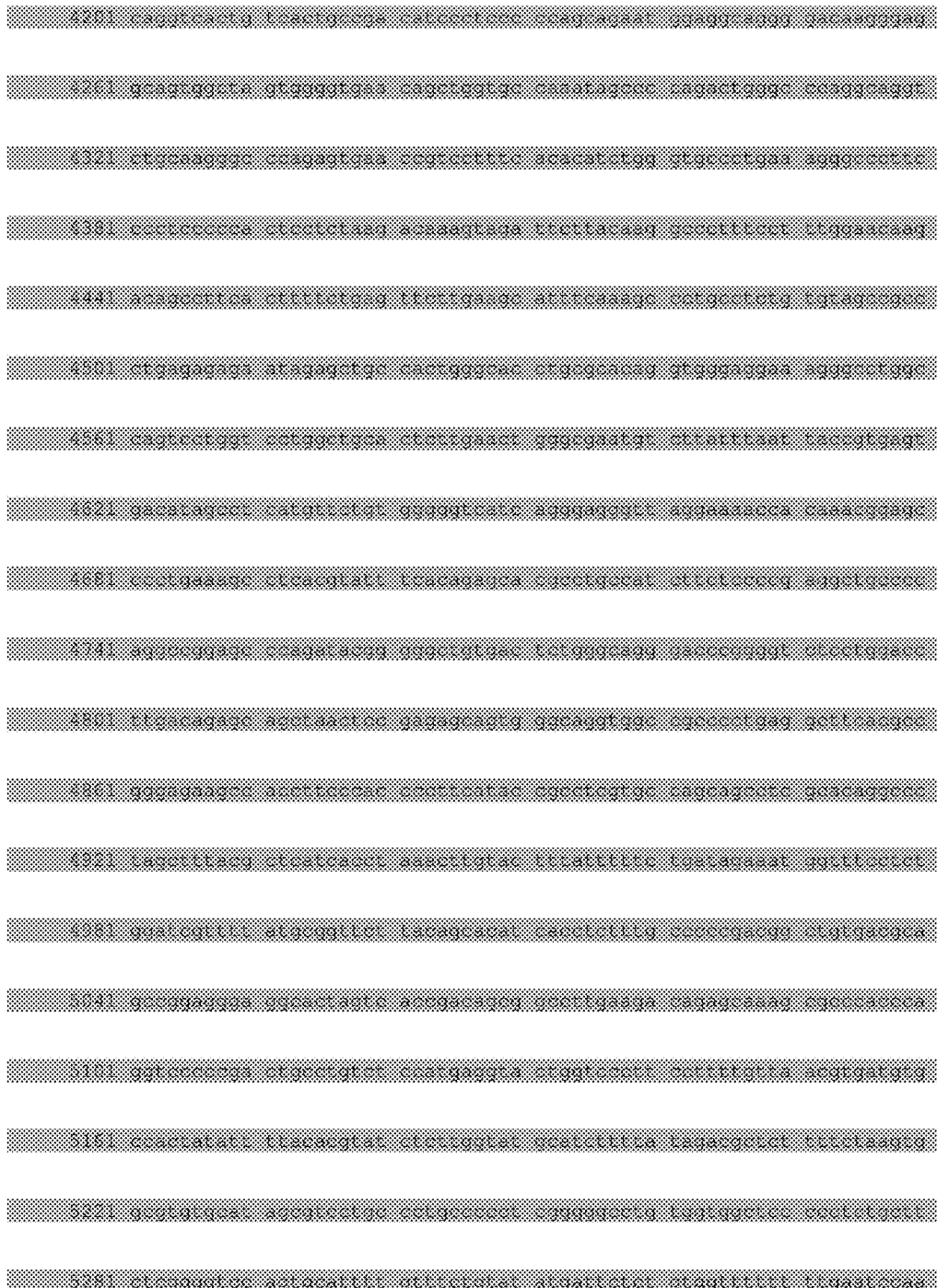

Primer and probe binding regions for ACTB are indicated in FIG. 13; primer and probe binding regions for ABL are indicated in FIG. 14; and primer and probe binding regions are indicated in FIG. 15.

TABLE 9

FFPE Master Mix

| component | stock solution conc. | unit | component in reaction final conc. | unit | total rxn volume (µL) | component volume (µL) per rxn | number of rxns | component final volume (µL) |
|---|---|---|---|---|---|---|---|---|
| 5× EZ Buffer | 5 | × | 1.000 | × | 50 | 10.000 | 120 | 1200.00 |
| dNTP Mix | 25 | mM | 0.325 | mM | 50 | 0.650 | 120 | 78.00 |
| ROX Dye | 2 | µM | 0.015 | µM | 50 | 0.368 | 120 | 44.10 |
| Aptamer | 24.82 | µM | 0.200 | µM | 50 | 0.403 | 120 | 48.35 |
| EGvIIIi1_−58to−41 | 55.75 | µM | 0.050 | µM | 50 | 0.045 | 120 | 5.38 |
| EGvIIIi1_−39to−21pFAM | 38.44 | µM | 0.150 | µM | 50 | 0.195 | 120 | 23.41 |
| EGwti7_−28to−9 | 53.48 | µM | 0.050 | µM | 50 | 0.047 | 120 | 5.61 |
| EGv3i1_+36to+18 | 52.95 | µM | 0.600 | µM | 50 | 0.567 | 120 | 67.99 |
| EGFRwti7_−to+8 NED MGB | 49.92 | µM | 0.450 | µM | 50 | 0.451 | 120 | 54.09 |
| $MnCl_2$ Activation | 100 | mM | 3.000 | mM | 50 | 1.500 | 120 | 180.00 |
| rTth | 3.2 | U/µL | 0.200 | U/µL | 50 | 3.125 | 120 | 375.00 |
| $H_2O$ | N/A | N/A | N/A | N/A | 50 | 2.651 | 120 | 318.07 |

TABLE 10

ACTB, ABL, and G6PD primer and probe mixes

| component | stock conc. (µM) | final conc. (µM) | total rxn volume (µL) | component volume (µL) | number of rxns | total component volume (µL) | mix name |
|---|---|---|---|---|---|---|---|
| bActl1_−53to−33 | 52.58 | 0.050 | 50 | 0.048 | 40 | 1.902 | ACTB |
| bActl1_−29to−10pCY5 | 52.34 | 0.150 | 50 | 0.143 | 40 | 5.732 | |
| bActl1_+17to−5 | 54.62 | 0.150 | 50 | 0.137 | 40 | 5.492 | |
| H2O | NA | NA | 50 | 4.672 | 40 | 186.874 | |
| ABLi3_fwd−21to+2 | 50.40 | 0.050 | 50 | 0.050 | 40 | 1.984 | ABL |
| ABLi3+65to+41 | 43.84 | 0.150 | 50 | 0.171 | 40 | 6.844 | |
| ABLi3+9to+33pCY5 | 36.76 | 0.150 | 50 | 0.204 | 40 | 8.160 | |
| H2O | NA | NA | 50 | 4.575 | 40 | 183.012 | |
| G6PDl2_fwd−50to−28 | 54.45 | 0.050 | 50 | 0.046 | 40 | 1.836 | G6PD |
| G6PDl2_rev−37to−12 | 45.82 | 0.150 | 50 | 0.164 | 40 | 6.547 | |

TABLE 10-continued

ACTB, ABL, and G6PD primer and probe mixes

| component | stock conc. (μM) | final conc. (μM) | total rxn volume (μL) | component volume (μL) | number of rxns | total component volume (μL) | mix name |
|---|---|---|---|---|---|---|---|
| G6PDv1__fwd346to367pCy5 | 53.55 | 0.150 | 50 | 0.140 | 40 | 5.603 | |
| H2O | NA | NA | 50 | 4.650 | 40 | 186.014 | |

TABLE 11

Internal control reaction mixes

| | beta-actin rxn | ABL rxn | G6PD rxn |
|---|---|---|---|
| Master Mix (μL) | 784.00 | 784.00 | 784.00 |
| ACTB mix (μL) | 196.00 | | |
| ABL mix (μL) | | 196.00 | |
| G6PD mix (μL) | | | 196.00 |

An aliquot of the FFPE Master Mix (Table 9) was mixed with aliquots from one of the three primer and probe mixes (Table 10) according to the volumes in Table 11 to produce three internal control reaction mixes comprising one of the three internal control primer and probe sets (e.g., for ACTB, ABL, or G6PD). Target RNAs used were the A549 EGFR mRNA positive control and a positive control known to express EGFRvIII mRNA ("U87vIII"), which was isolated from a GBM FFPE sample and confirmed to express EGFRvIII mRNA. U87vIII was produced by stably transfecting a glioblastoma-derived cell line (U87-MG) with the EGFRvIII mutant. 10-fold serial dilutions were made of each RNA in H$_2$O to provide a range of from 50 nanograms of RNA to 0.0005 nanograms (0.5 picograms) of RNA per reaction. 50 nanograms of genomic DNA and water were used for negative controls. 25 μL of Master Mix and 25 μL of target RNA were added to each well of a 96-well plate and thermocycled according to the following program:

| Stage | Cycles | Step | Temp (C.) | Time (min:sec) |
|---|---|---|---|---|
| 1 | 1 | 1 | 62 | 30:00 |
| 2 | 4 | 1 | 92 | 00:30 |
| | | 2 | 60 | 00:30 (1-s autoincrement) |
| 3 | 56 | 1 | 92 | 00:30 |
| | | 2 | 62 | 00:30 (1-s autoincrement) |
| | | 3 | 58 (read*) | 00:40 |

*in the "read" steps, the fluors FAM, NED, Cy5, and ROX are monitored.

Data were analyzed using software for generating and analyzing real-time PCR data (e.g., plotting data, data reduction, determining Ct values, etc.). Threshold values for Cy5, FAM, and NED=0.100. EGFRvIII RT-PCR curves were obtained and Ct, delta Ct (dCt), and dRN values were calculated, and linearity plots were produced.

Figure 18A:
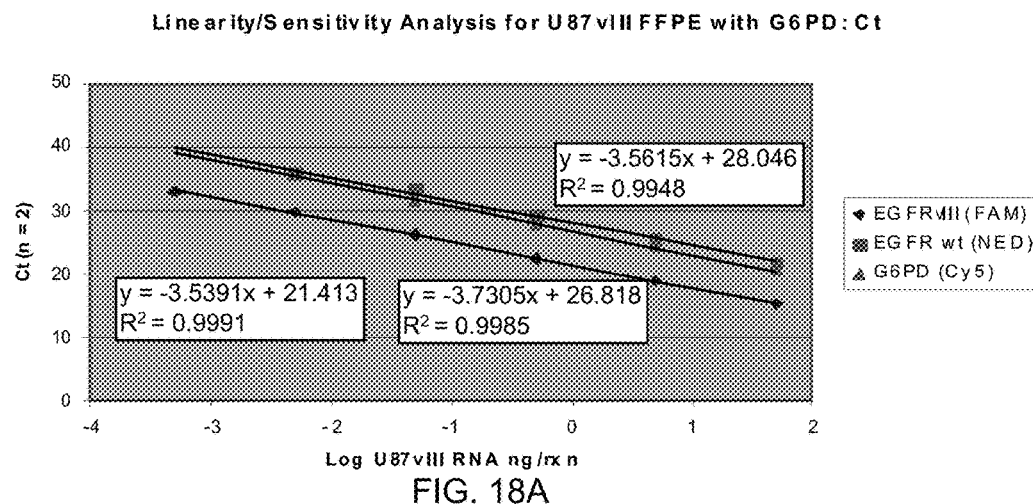
FIGS. 18A and 18B are a series of plots showing Ct values measured for total EGFR, EGFRvIII, and G6PD and the dCt values calculated for total EGFR and EGFRvIII relative to G6PD in samples comprising RNA prepared from the EGFRvIII positive control U87vIII.
Figure 18B:
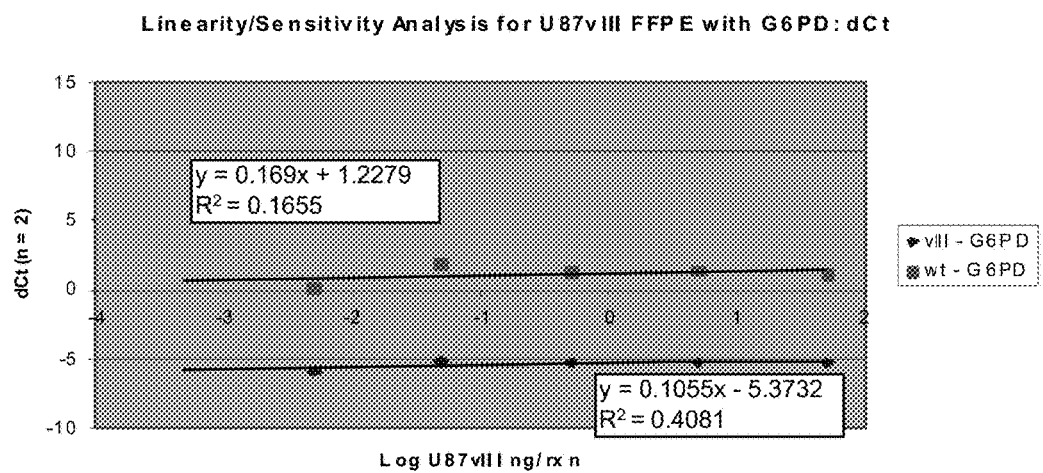
Figure 19A:
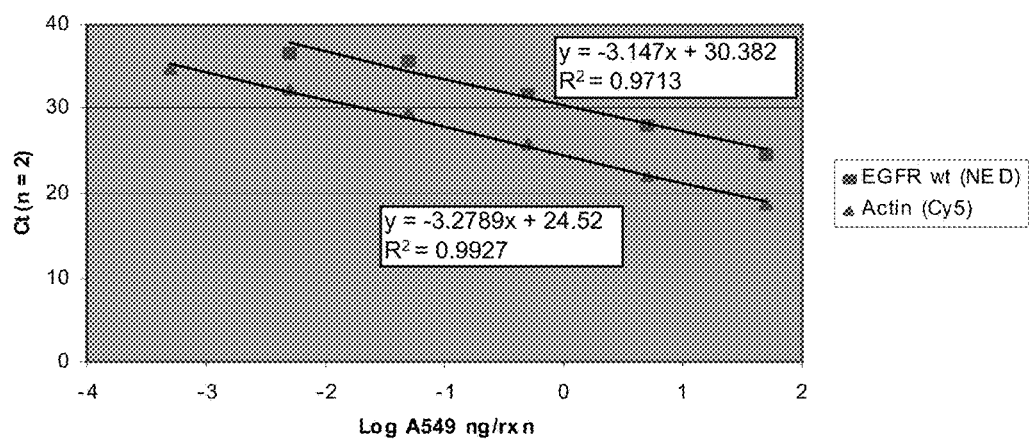
FIGS. 19A and 19B are a series of plots showing Ct values measured for total EGFR and ACTB and the dCt values calculated for total EGFR relative to ACTB in samples comprising RNA prepared from the total EGFR positive control A549.
Figure 19B:
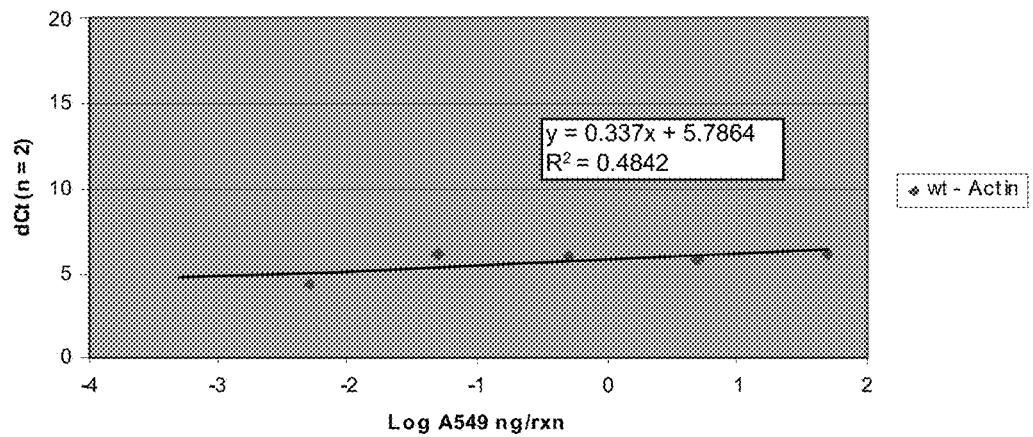
Figure 20A:
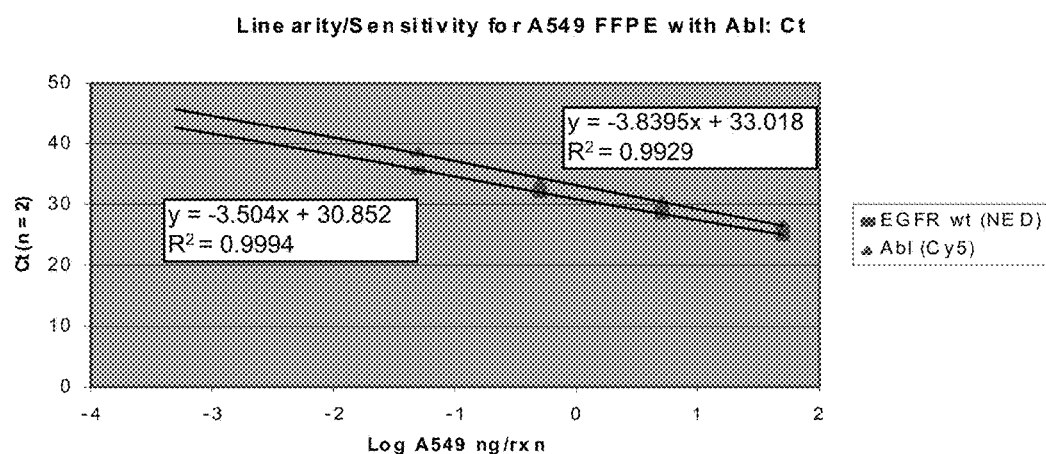
FIGS. 20A and 20B are a series of plots showing Ct values measured for total EGFR and ABL and the dCt values calculated for total EGFR relative to ABL in samples comprising RNA prepared from the total EGFR positive control A549.
Figure 20B:
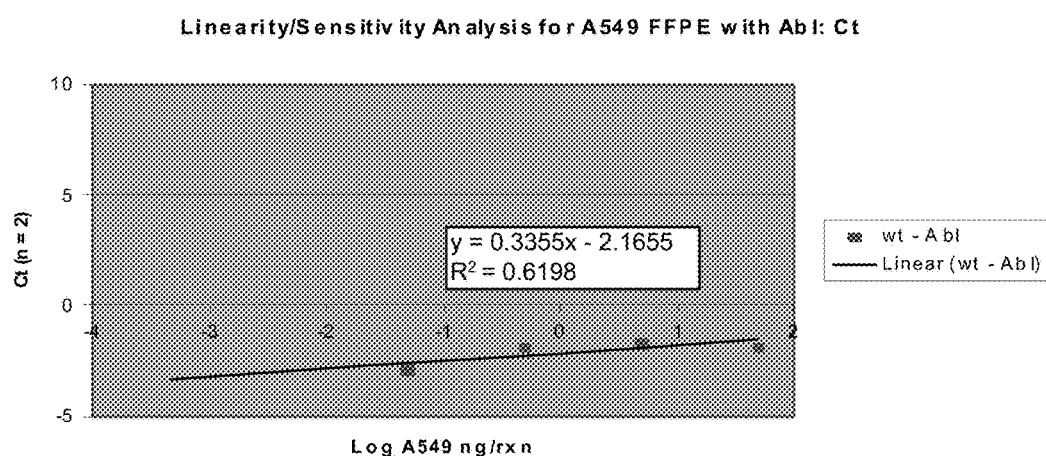
Figure 21A:
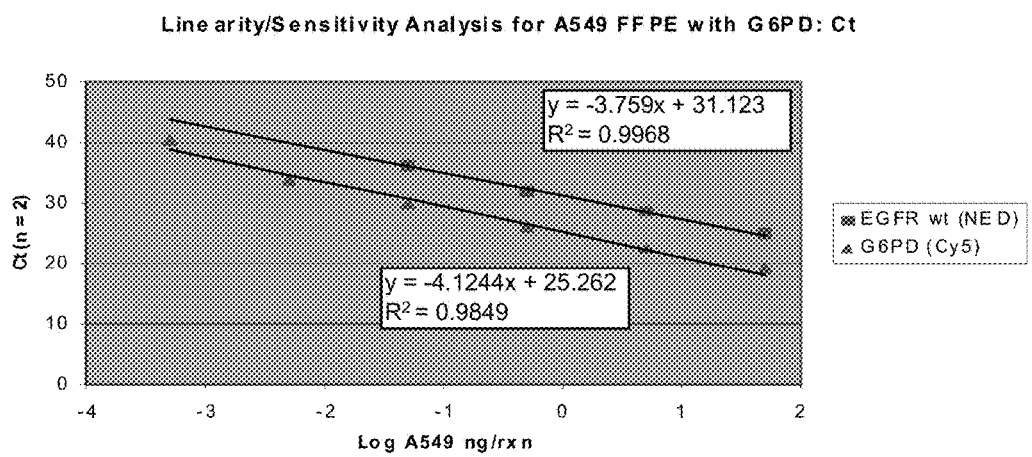
FIGS. 21A and 21B are a series of plots showing Ct values measured for total EGFR and G6PD and the dCt values calculated for total EGFR relative to G6PD in samples comprising RNA prepared from the total EGFR positive control A549.
Figure 21B:
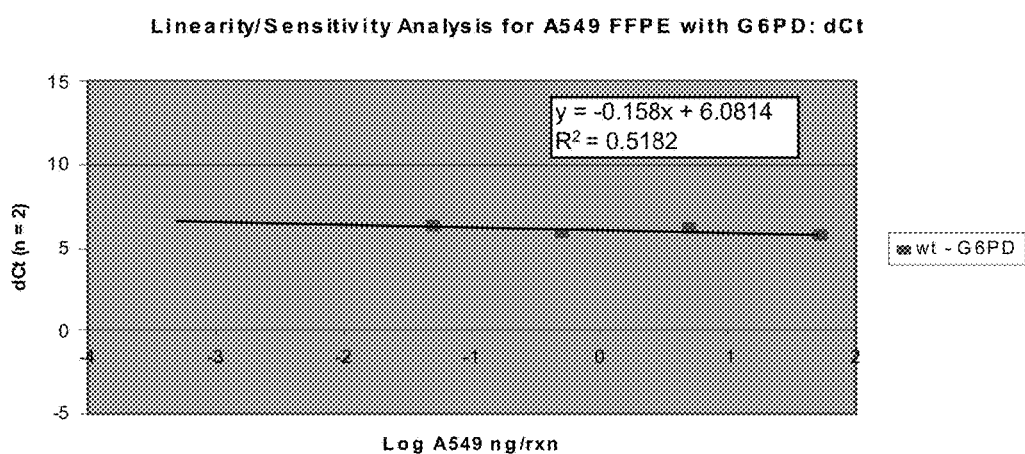
Figure 22:
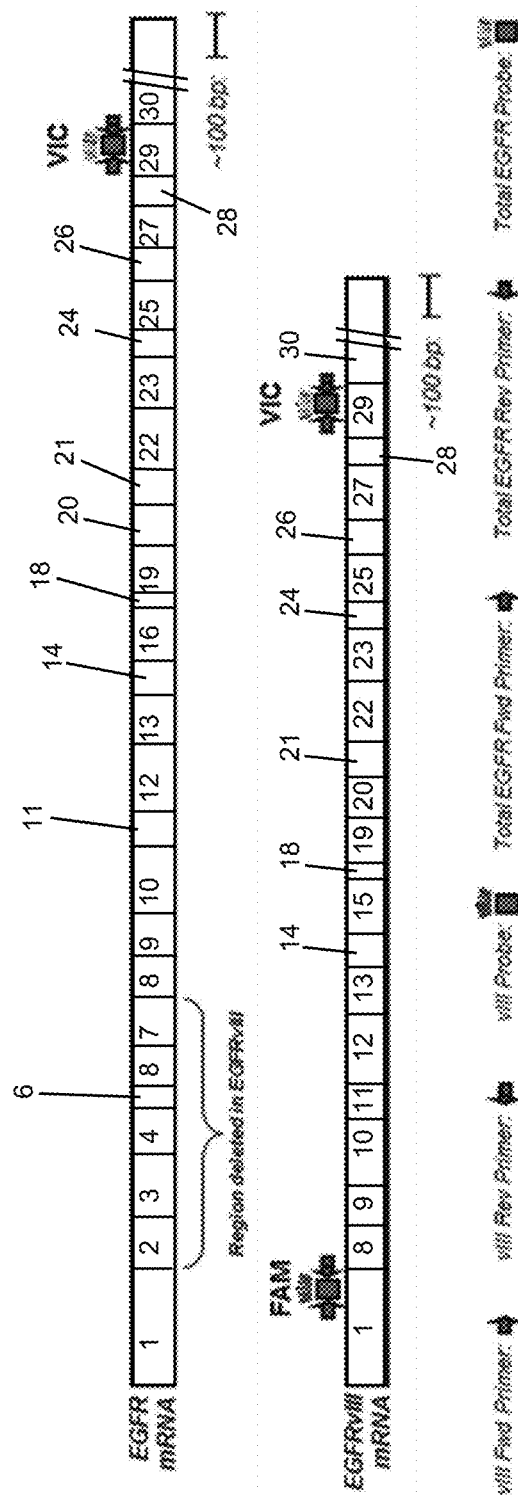
FIG. 22 is a schematic drawing showing primers and probes for detecting and/or quantifying total EGFR mRNA and EGFRvIII mRNA. Exons comprising non-rearranged EGFR mRNA ("EGFR mRNA", top) and EGFRvIII mRNA ("EGFRvIII mRNA", bottom) are depicted as numbered boxes. Exons 2-7 (shaded grey and marked with brace labeled "Region deleted in EGFRvIII") are present in EGFR, but are deleted from the EGFRvIII deletion variant. Exon 1 and exons 8 through 30 are retained in both EGFR and EGFRvIII and total EGFR primers and probes amplify both EGFRvIII and EGFR mRNA. As a result of the deletion, exons 1 and 8 are juxtaposed in EGFRvIII RNA. The locations of primers and probes are indicated above the respective mRNAs. The EGFRvIII probe is labeled with a "FAM" fluorescent moiety and the total EGFR probe is labeled with a "VIC" fluorescent moiety. The primers associated with each probe are indicated by arrows immediately upstream and downstream of the labeled probes.

Plots of data were evaluated to assess the sensitivity of the assays to measure total EGFR and EGFRvIII expression in RNA samples prepared from the U87vIII EGFRvIII mRNA positive control (see FIG. 16, FIG. 17, and FIG. 18) and to evaluate the sensitivity of the assays to measure total EGFR expression in RNA samples prepared from the A549 EGFR mRNA positive control (see FIG. 19, FIG. 20, and FIG. 21). Data were assessed without relating it to one of the ACTB, ABL, or G6PD internal controls (Ct values in FIG. 16A, FIG. 17A, FIG. 18A, FIG. 19A, FIG. 20A, and FIG. 21A) and in relation to one of the ACTB, ABL, or G6PD internal controls (dCt values in FIG. 16B, FIG. 17B, FIG. 18B, FIG. 19B, FIG. 20B, and FIG. 21B).

In addition, the A549 EGFR mRNA control acts as a negative control for the detection of EGFRvIII. Accordingly, the data collected during the experiments described herein demonstrates the specificity of the EGFRvIII PCR signal in the methods and experiments described above.

Figure 16A:
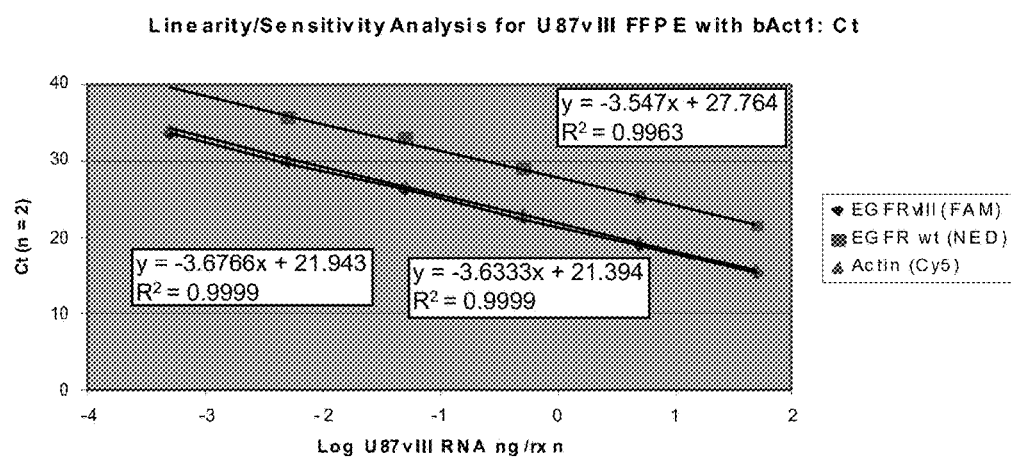
FIGS. 16A and 16B are a series of plots showing Ct values measured for total EGFR, EGFRvIII, and ACTB and the dCt values calculated for total EGFR and EGFRvIII relative to ACTB in samples comprising RNA prepared from the EGFRvIII positive control U87vIII.
Figure 16B:
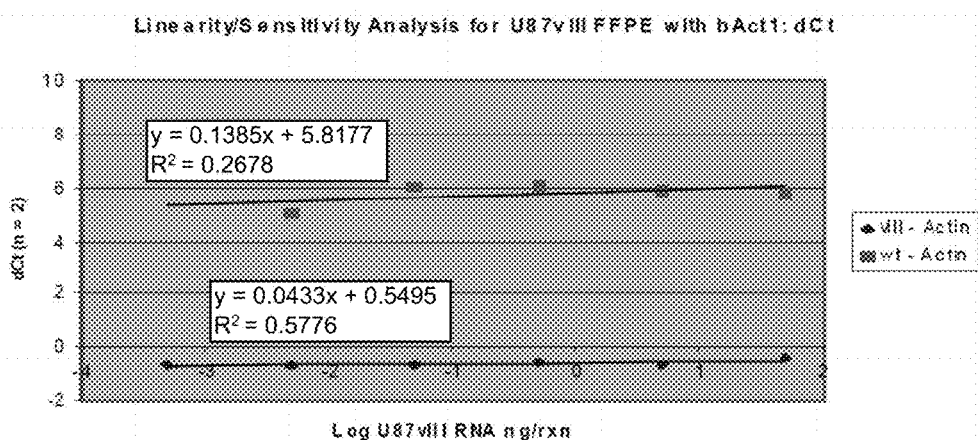
Figure 17A:
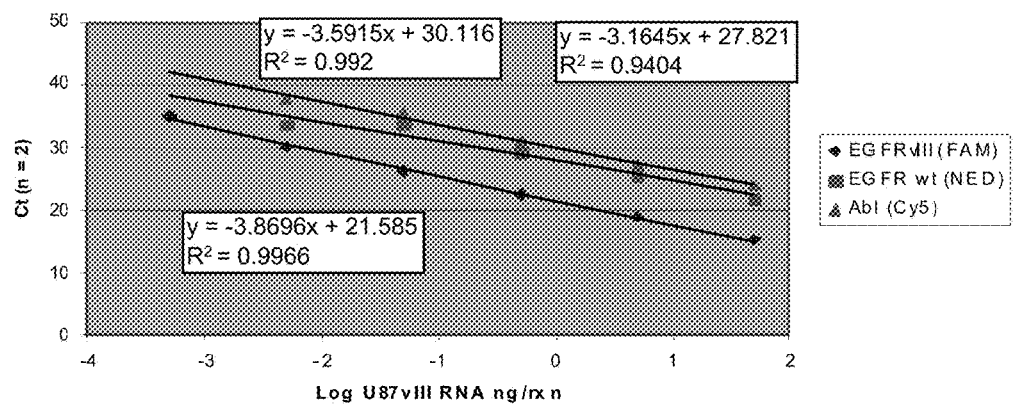
FIGS. 17A and 17B are a series of plots showing Ct values measured for total EGFR, EGFRvIII, and ABL and the dCt values calculated for total EGFR and EGFRvIII relative to ABL in samples comprising RNA prepared from the EGFRvIII positive control U87vIII.
Figure 17B:
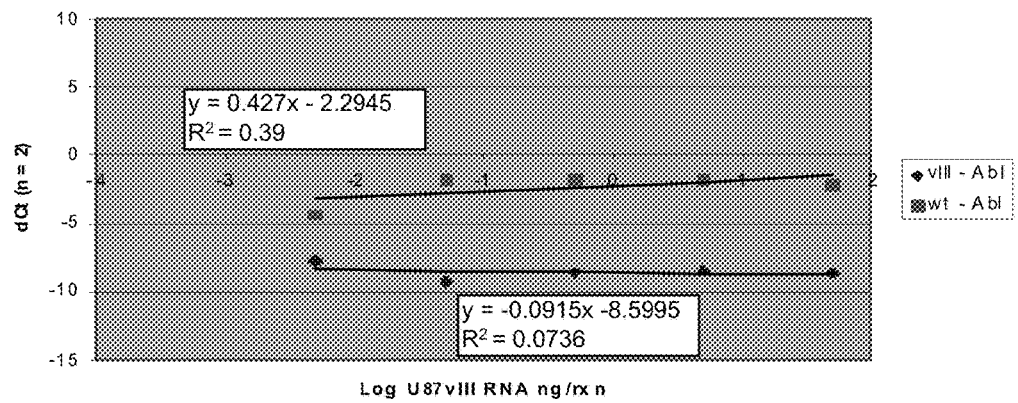

Further, plots of data were evaluated to assess the linearity of the response of the measured Ct and dCt values for total EGFR and EGFRvIII concentrations with the total RNA in the sample. Plots were prepared comprising measured Ct values for detection of total EGFR, EGFRvIII, and an internal control (e.g., ACTB, ABL, or G6PD) as a function of the total concentration of RNA prepared from the EGFRvIII positive control U87vIII (FIG. 16A, FIG. 17A, FIG. 18A). The Ct data were used to calculate dCt values for detection of EGFR and EGFRvIII relative to the internal control in the sample (FIG. 16B, FIG. 17B, FIG. 18B). Plots were also prepared comprising measured Ct values for detection of total EGFR and an internal control (e.g., ACTB, ABL, or G6PD) as a function of the total concentration of RNA prepared from the total EGFR positive control A549 (FIG. 19A, FIG. 20A, FIG. 21A). The Ct data were used to calculate dCt values for detection of total EGFR relative to the internal control in the sample (FIG. 19B, FIG. 20B, FIG. 21B).

None of the internal controls altered the linearity or sensitivity of EGFRvIII or EGFRwt detection (e.g., compare FIG. 16A with FIG. 16B, FIG. 17A with FIG. 17B, FIG. 18A with FIG. 18B, FIG. 19A with FIG. 19B, FIG. 20A with FIG. 20B, and FIG. 21A with FIG. 21B). Amongst the three internal controls, beta-actin provided lower Ct values, higher dRN values, and a greater sensitivity of detection (e.g., approximately 0.5 picograms or more).

The following settings were used for Ct threshold: FAM=0.1, NED=0.75, Cy5=0.1. To determine the relative level of total EGFR mRNA in a given sample, the Ct value of total EGFR is subtracted from the Ct value of ACTB or other internal control to provide a EGFR dCt. Higher EGFR dCt values indicate higher EGFR mRNA expression. Similarly, the relative level of EGFRvIII mRNA is calculated by subtracting the Ct value of EGFRvIII from the Ct value of ACTB or other internal control to provide a EGFRvIII dCt. Higher EGFRvIII dCt values indicate higher EGFRvIII expression. A cutoff dCt can be assigned for EGFRvIII where any EGFRvIII dCt higher than the cutoff is considered EGFRvIII positive. Alternatively, a maximum EGFRvIII Ct value can be established where lower (earlier) Ct values indicate EGFRvIII positive. A cutoff dCt can be assigned for total EGFR where any EGFR dCt higher than the cutoff is considered to be a high expresser of EGFR.

Example 4

Evaluation of Linearity and Dynamic Range

During the development of embodiments of the technology provided herein, experiments were conducted to assess the dynamic range and linear response of the real-time PCR assay signal to the level of EGFRvIII, tEGFR, and actin expression. Data were collected in real-time PCR assays of RNA dilution panels prepared by diluting RNA from FFPE cell pellets from a cell line (U87MG de2-7) that expresses EGFRvIII, tEGFR, and actin.

Methods

During the development of embodiments of the technology, experiments were conducted to detect EGFRvIII mRNA and total EGFR mRNA. In some experiments, mRNA samples were prepared from formalin-fixed paraffin-embedded (FFPE) cell pellets from a cell line (U87MG de2-7) that expresses EGFRvIII, tEGFR, and actin. In some embodiments, the assays were performed on a commercial real-time PCR instrument such as, e.g., the ABBOTT M2000 REAL-TIME real-time PCR system. In some embodiments, the assays are used for target amplification, detection of EGFRvIII target, and relative quantification of total EGFR RNA (vs. an endogenous control gene) either as a complete cocktail or in a subset of primer/probe combinations. The compositions described in this example find use for amplification of EGFRvIII, total EGFR, and actin mRNA.

Data were collected from samples processed using a manual sample preparation procedure and sample preparation kit (e.g., an ABBOTT TARGETPREP RNA PRO nucleic acid sample preparation kit). Purified sample ribonucleic acid (RNA) was combined in a 96-well optical reaction plate with an EGFR amplification master mix using a manual process. The optical reaction plate was manually transferred to the real-time PCR instrument for amplification and detection. Assay results were automatically reported on the real-time PCR instrument at run completion.

Each sample was assayed by reverse transcription (RT) PCR to detect expression of total EGFR, beta-actin mRNA, and EGFRvIII mRNA. Software parameters used on the real-time PCR instrument were provided in an assay application specification file loaded onto the real-time PCR instrument, e.g., from an assay CD-ROM disk.

Compositions (e.g., reaction mixtures) used for amplification in some embodiments are provided in Table 12 and Table 13 below.

The PCR EZ Buffer indicated in Table 12 comprises bicine and glycerol. The Oligonucleotide Reagent and Activation Reagent were prepared in molecular grade water and contain a preservative biocide reagent (e.g., PROCLIN 300 preservative and/or PROCLIN 950 preservative).

In some embodiments, the primers and probes of the amplification reagent formulation in the "Component" column of Table 12 are the following primers and probes in Table 13:

TABLE 13 amplification reagent formulation primer and probe sequences

| Material | Oligo name | SEQ ID NO | Sequence (5' to 3') and description |
|---|---|---|---|
| vIII Forward Primer | EGvIIIi1_-58to-41 | 2 | CTC CTG GCG CTG CTG GCT |
| vIII Reverse Primer | EGvIII-A | 33 | CGT GAT CTG TCA CCA CAT AAT TAC CTT TC |
| vIII probe (FAM) | EGvIIIi1_-39to-21pFAM-BHQ1 dT | 42 | FAM-CGC TCT GCC CGG CGA GTC G-BHQ1dT BHQ1 = Black Hole Quencher 1 |
| Total Forward Primer | EGwti29_-47to-25 | 8 | CGC CTT GAC TGA GGA CAG CAT AG |
| Total Reverse Primer | EGwti29_+23to-3 | 7 | GGG AAC GGA CTG GTT TAT GTA TTC AG |

TABLE 12 amplification reagent formulation

| Reagent | Component | Oligo name | SEQ ID NO: | Final Concentration in 50 μL reaction | Unit |
|---|---|---|---|---|---|
| Oligonucleotide Reagent | EGFRvIII Forward Primer | EGvIIIi1_-58to-41 | 2 | 0.063 | μM |
| | EGFRvIII Reverse Primer | EGvIII-A | 33 | 0.282 | μM |
| | EGFRvIII probe | EGvIIIi1_-39to-21 pFAM-BHQ1 dT | 42 | 0.188 | μM |
| | Total EGFR Forward Primer | EGwti29_-47to-25 | 8 | 0.050 | μM |
| | Total EGFR Reverse Primer | EGwti29_+23to-3 | 7 | 0.075 | μM |
| | Total EGFR Probe | Total EGFR probe | 32 | 0.350 | μM |
| | beta-Actin (ACTB) Forward Primer | bActI1_-53to-33 | 14 | 0.100 | μM |
| | beta-Actin (ACTB) Reverse Primer | bActI1_+17to-5 | 13 | 0.450 | μM |
| | beta-Actin (ACTB) probe | bActI1_-29to-10pNED | 43 | 0.110 | μM |
| | PCR EZ Buffer | N/A | N/A | 1X | |
| | Aptamer | N/A | N/A | 0.200 | μM |
| | ROX Reference | N/A | N/A | 0.060 | μM |
| | dNTPs | N/A | N/A | 0.488 | mM |
| Activation reagent | MnCl₂ | N/A | N/A | 4.00 | mM |
| Enzyme Reagent | rTth Polymerase | N/A | N/A | 15.04 | units/reaction |

TABLE 13-continued amplification reagent formulation
primer and probe sequences

| Material | Oligo name | SEQ ID NO | Sequence (5' to 3') and description |
|---|---|---|---|
| Total Probe (VIC) | Total EGFR probe | 32 | VIC-A7A C76 67C 67C 7AG 6G-BHQ2dT 6 = 5-Propynyl dU 7 = 5-Methyl dC BHQ2 = Black Hole Quencher 2 |
| ACTB Forward Primer | bActl1_-53to-33 | 14 | GAG CAC AGA GCC TCG CCT TTG |
| ACTB Reverse Primer | bActl1_+17to-5 | 13 | TCA TCA TCC ATG GTG AGC TGG C |
| ACTB probe (NED) | bActl1_-29 to-10pNED | 43 | NED-ATC CGC CGC CCG TCC ACA CC-BHQ2dT |

In some embodiments, the "Total EGFR probe" (e.g., of Table 12) has a sequence of one of the following oligonucleotides provided in Table 14:

TABLE 14 exemplary sequences of total EGFR probe

| oligo name | short name | oligo type | sequence (5' to 3') | SEQ ID NO: |
|---|---|---|---|---|
| EGi29_-21 to-5p1 | Totalp1 | probe | VIC - ACA CCT TCC TCC CAG TG - BHQ2dt | 38 |
| EGi29_-21 to-5p2 | Totalp2 | probe | VIC - A7A C76 67C 67C 7AG 6G - BHQ2dt | 39 |
| EGi29_-21 to-5p3 | Totalp3 | probe | VIC - A5A C56 65C 65C 5AG 6G - BHQ2dt | 40 |
| EGi29_-21 to-5p4 | Totalp4 | probe | VIC - A7A C56 67C 65C 5AG 6G - BHQ2dt | 41 |

In Table 14, a base indicated by a "5" is a 5-Propynyl dC, a base indicated by a "6" is a 5-Propynyl dU, and a base indicated by a "7" is a 5-Methyl dC. In Table 14, BHQ2 indicates Black Hole Quencher 2 and VIC indicates a VIC fluorescent moiety.

In some embodiments, the amplification cycling conditions used in the real-time PCR assays described herein are those provided in Table 15:

TABLE 15 amplification cycling conditions

| Step Number | Number of Cycles | Description | Temperature | Time |
|---|---|---|---|---|
| 1 | 1 | Denaturation | 95° C. | 1 minute |
| 2 | 1 | Reverse Transcription | 62° C. | 30 minutes |
| 3 | 4 | Denaturation | 92° C. | 30 seconds |
|   |   | Annealing | 60° C. | 30 seconds |
| 4 | 50 | Denaturation | 92° C. | 30 seconds |
|   |   | Annealing | 62° C. | 30 seconds |
|   |   | Extension | 58° C. | 40 seconds |

Figure 23:
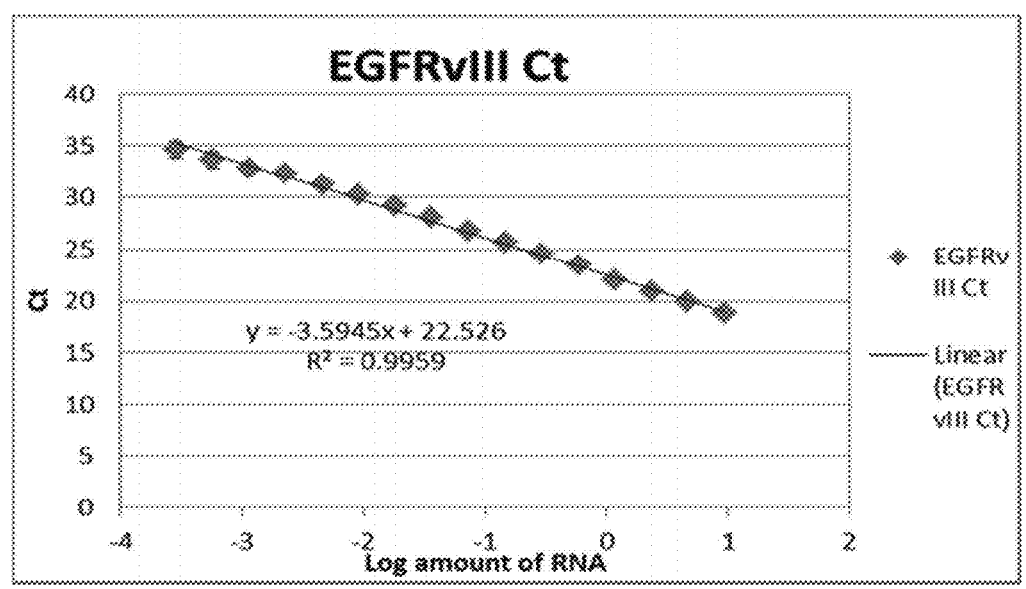
FIG. 23 is a scatter plot of EGFRvIII Ct from a real-time PCR assay of RNA dilution panels prepared from FFPE cell pellet of U87MG de2-7 cell line that expresses EGFRvIII, tEGFR, and actin. The averages of data from 9 PCR replicates of each dilution panel were plotted; error bars=SD.
Figure 24:
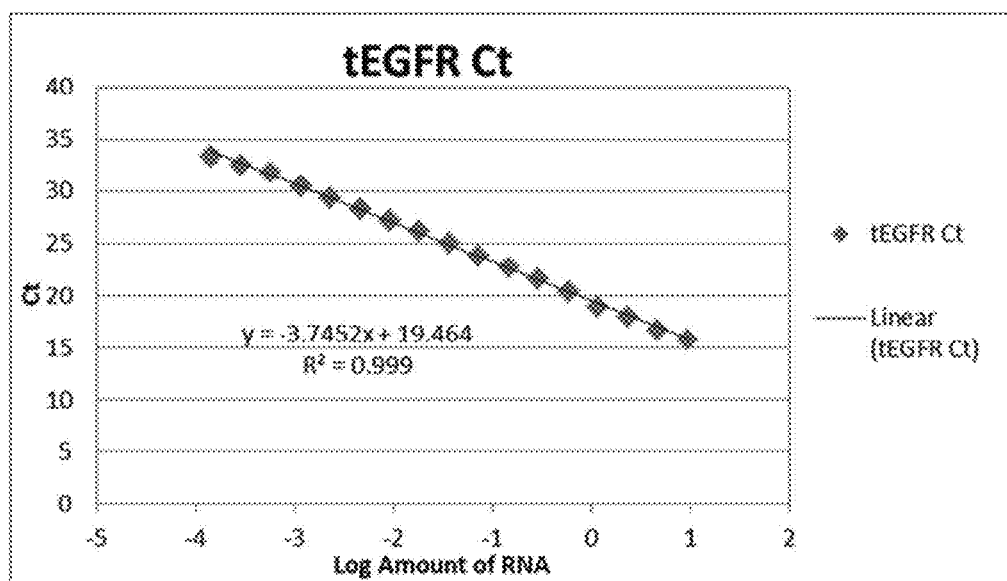
FIG. 24 is a scatter plot of total EGFR Ct from a real-time PCR assay of RNA dilution panels prepared from FFPE cell pellet of U87MG de2-7 cell line that expresses EGFRvIII, tEGFR, and actin. The averages of data from 9 PCR replicates of each dilution panel were plotted; error bars=SD.
Figure 25:
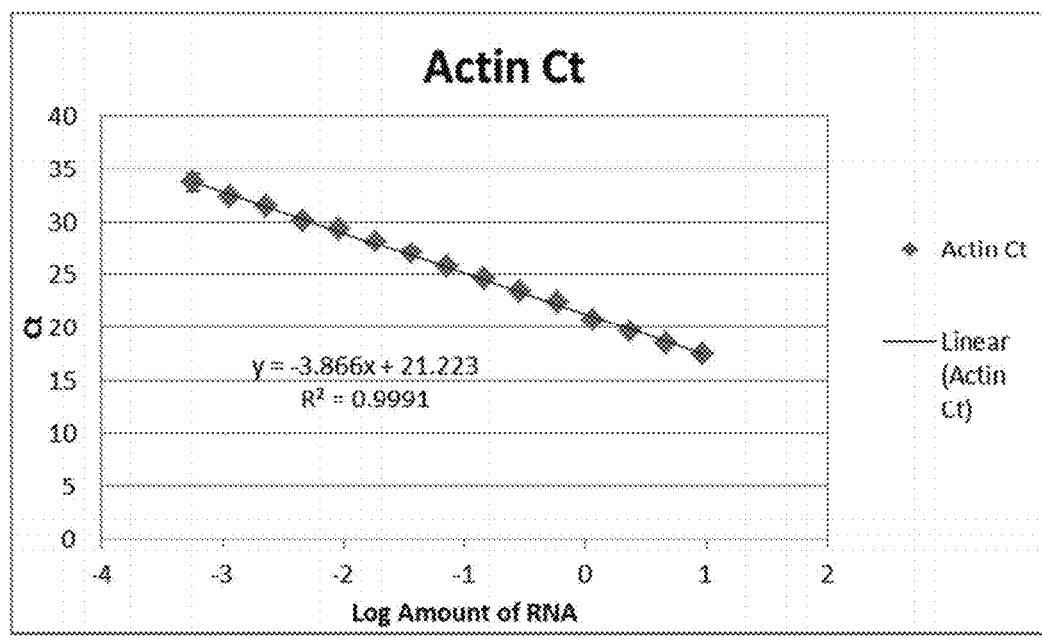
FIG. 25 is a scatter plot of actin Ct from a real-time PCR assay of RNA dilution panels prepared from FFPE cell pellet of U87MG de2-7 cell line that expresses EGFRvIII, tEGFR, and actin. The averages of data from 9 PCR replicates of each dilution panel were plotted; error bars=SD.

During the development of some embodiments of the technology, data were collected to evaluate the linearity and dynamic range of the EGFR assay (e.g., using reaction mixtures as described above). For example, experiments were conducted in which the linearity and dynamic range were evaluated using RNA dilution panels prepared by diluting RNA from FFPE cell pellets from a cell line (U87MG de2-7) that expresses EGFRvIII, tEGFR, and actin. The RNA was diluted in molecular biology grade water to prepare dilution panels ranging from 9320 pg to 0.0022 pg RNA per PCR well. Three PCR replicates of each dilution panel on each of three real-time PCR instruments were tested, resulting in a total of 9 replicates. Real-time data collected for EGFRvIII, total EGFR, and actin are shown in FIGS. 23, 24, and 25, respectively.

Results

The dynamic range and limit of quantification were evaluated. In particular, the dynamic range was calculated as the range of RNA amount demonstrating 100% detection of replicates with <5% CV. The limit of quantification was calculated as the cycle number value of the lowest dilution panel member within the dynamic range. Results are provided in Table 16:

TABLE 16

Dynamic range and Limit of Quantitation (LoQ)

| Target | Dynamic Range | cycle number range | Limit of Quantification (LoQ) (CN) |
|---|---|---|---|
| EGFRvIII | 9320 pg to 0.569 pg | 18.86-34.63 | 34.63 |
| Total EGFR | 9320 pg to 0.284 pg | 15.79-33.46 | 33.46 |
| Actin | 9320 pg to 0.142 pg | 17.46-33.70 | 33.70 |

The data collected indicated that the RNA extracted from FFPE cell pellets from a cell line (U87MG de2-7) that expresses EGFRvIII, tEGFR, and actin provides adequate linearity for EGFRvIII (see FIG. 23), total EGFR (see FIG. 24), and Actin (see FIG. 25) across a wide range of Ct values. EGFRvIII demonstrated dynamic range of 4.21 log (9320 pg to 0.569 pg) and a limit of quantitation for EGFRvIII was determined to be 34.63 cycles. Total EGFR demonstrated a dynamic range of 4.52 log (9320 pg to 0.284 pg) and a limit of quantitation for Total EGFR was determined to be 33.46 cycles. Actin demonstrated dynamic range of 4.82 log (9320 pg to 0.142 pg) and a limit of quantitation for actin was determined to be 33.70 cycles.

Example 5

Specificity Study

Further experiments were conducted during the development of embodiments of the technology disclosed herein. In these experiments, the specificity of the real-time assay for the EGFRvIII target was assessed by evaluating the EGFRvIII positive or negative status for 20 non-GBM brain tissue specimens from normal donors. Amplification of EGFRvIII mRNA to generate an EGFRvIII-positive result was not expected for the specimens in this study, so EGFRvIII negativity rate was used to assess the analytical specificity for EGFRvIII.

Methods

Three FFPE slide sections for each of the 20 non-GBM brain specimens were processed for RNA extraction using Target-Prep RNA Pro kit. EGFR mastermix was prepared by combining components of the EGFR amplification reagent kit. EGFR amplification mastermix configuration is listed in Table 12. The RNA eluates were mixed with EGFR mastermix in wells of a 96-well optical reaction plate using a manual process. The optical reaction plate was manually transferred to the real-time PCR instrument for amplification and detection. Assay results were automatically reported on the real-time PCR instrument at run completion. For each specimen, 3 replicates were tested with 1 lot of EGFR assay reagents across 3 runs (1 replicate per run) on a single real-time PCR instrument.

Results

EGFRvIII positivity and negativity status were reported by comparing the EGFRvIII CN values to a clinical cutoff value of 30.00 CN. EGFRvIII result was reported as 'NEG' (negative) for specimens with a CN value >30.00 or a CN value of −1. Data were collected from all replicates from all three runs and are presented in Table 17.

TABLE 17

Specificity analysis

| Run | Number of negative specimens tested | Number of EGFRvIII negative specimens detected | EGFRvIII Negativity Rate |
|---|---|---|---|
| 1 | 20 | 20 | 100.0% |
| 2 | 20 | 20 | 100.0% |
| 3 | 20 | 20 | 100.0% |

As indicated by the data, the 20 non-GBM brain tissue specimens from normal donors did not generate a positive EGFRvIII assay result in any of the 3 individual runs; therefore, an EGFRvIII Negativity Rate of 100.0% was attained. This suggests that EGFRvIII primers and probes are selectively amplifying and detecting EGFRvIII signal and no amplification is observed from non-GBM brain specimens.

Example 6

Testing GBM Specimens

In additional experiments conducted during the development of embodiments of the technology described herein, thirty-two (32) FFPE glioblastoma multiforme (GBM) specimens were screened using the real-time assay for detection of EGFRvIII and relative expression of total EGFR. EGFRvIII positive or negative, and Total EGFR positive and negative status, were determined for the set of GBM specimens.

Methods

The FFPE glioblastoma multiforme (GBM) specimens were obtained from commercial vendors (Asterand and Discovery Life). Amplification of actin, total EGFR, and EGFRvIII mRNA were evaluated. During the experiments, RNA was extracted from one slide from each specimen using Target-Prep RNA Pro kit and PCR replicatens were tested from each RNA eluate. Sample preparation was performed in 2 batches. In each batch, 1 EGFR negative control and 1 EGFR positive control were included. EGFR mastermix was prepared by combining components of the EGFR amplification reagent kit. EGFR amplification mastermix configuration is listed in Table 12. The RNA eluates were mixed with EGFR mastermix in wells of a 96-well optical reaction plate using a manual process. The optical reaction plate was manually transferred to the real-time PCR instrument for amplification and detection. Assay results were automatically reported on the real-time PCR instrument at run completion.

Results

The data collected are shown in Table 18. Average cycle numbers from two PCR replicates of EGFRvIII ("EGFRvIII CN"), total EGFR ("tEGFR CN"), and actin ("ACTB CN") are reported in Table 18. These data were used to calculate the total EGFR relative to actin ("tEGFR dCN") and presence or absence of EGFRvIII. These results were used to assign a "positive" or "negative" result to the total EGFR and EGFRvIII assays.

TABLE 18

Results from testing FFPE GBM specimens

| Sample ID | Vendor | EGFRvIII CN | tEGFR CN | ACTB CN | tEGFR dCN | EGFR Result |
|---|---|---|---|---|---|---|
| 1183334B | Asterand | ND | 21.14 | 15.49 | −5.66 | tEGFR NEG; vIII NEG |
| 1174894B | Asterand | ND | 20.17 | 14.44 | −5.74 | tEGFR NEG; vIII NEG |
| 1199188B | Asterand | ND | 20.61 | 14.24 | −6.37 | tEGFR NEG; vIII NEG |
| 1199193B | Asterand | 34.36 | 20.17 | 13.65 | −6.52 | tEGFR NEG; vIII NEG |
| 1180366B | Asterand | ND | 22.15 | 15.54 | −6.61 | tEGFR NEG; vIII NEG |
| R13-0321 | Discovery Life | ND | 27.52 | 20.88 | −6.65 | tEGFR NEG; vIII NEG |
| R15-0034 | Discovery Life | ND | 24.44 | 17.16 | −7.28 | tEGFR NEG; vIII NEG |
| 1179610B | Asterand | ND | 19.74 | 12.40 | −7.34 | tEGFR NEG; vIII NEG |
| R15-0028 | Discovery Life | 35.74/ ND | 18.43 | 11.06 | −7.37 | tEGFR NEG; vIII NEG |
| 1180569B | Asterand | ND | 23.03 | 15.40 | −7.63 | tEGFR NEG; vIII NEG |
| R13-0397 | Discovery Life | ND | 29.10 | 21.42 | −7.69 | tEGFR NEG; vIII NEG |
| R14-0493 | Discovery Life | ND | 32.47 | 24.77 | −7.70 | tEGFR NEG; vIII NEG |

TABLE 18-continued

Results from testing FFPE GBM specimens

| Sample ID | Vendor | EGFRvIII CN | tEGFR CN | ACTB CN | tEGFR dCN | EGFR Result |
|---|---|---|---|---|---|---|
| 1199219B | Asterand | 35.63/ND | 22.60 | 14.56 | −8.04 | tEGFR NEG; vIII NEG |
| 1184408B | Asterand | ND | 18.18 | 18.85 | 0.68 | tEGFR POS; vIII NEG |
| R13-0588 | Discovery Life | 33.94 | 15.88 | 15.41 | −0.47 | tEGFR POS; vIII NEG |
| 355098B4 | Asterand | 31.43 | 20.44 | 19.63 | −0.81 | tEGFR POS; vIII NEG |
| 388101A1 | Asterand | 32.25 | 25.53 | 24.41 | −1.13 | tEGFR POS; vIII NEG |
| 1184693B | Asterand | 30.23 | 22.17 | 20.90 | −1.28 | tEGFR POS; vIII NEG |
| 355101A1 | Asterand | 34.40 | 23.72 | 22.30 | −1.42 | tEGFR POS; vIII NEG |
| 1194912B | Asterand | ND | 22.01 | 19.88 | −2.13 | tEGFR POS; vIII NEG |
| R15-0002 | Discovery Life | ND | 17.94 | 15.63 | −2.31 | tEGFR POS; vIII NEG |
| 388085A2 | Asterand | ND | 30.78 | 27.94 | −2.84 | tEGFR POS; vIII NEG |
| 354254B1 | Asterand | ND | 27.94 | 24.81 | −3.14 | tEGFR POS; vIII NEG |
| 1199198B | Asterand | 32.05 | 16.39 | 13.15 | −3.24 | tEGFR POS; vIII NEG |
| 388104A1 | Asterand | ND | 29.15 | 24.50 | −4.65 | tEGFR POS; vIII NEG |
| 1194915B | Asterand | ND | 19.35 | 14.15 | −5.20 | tEGFR POS; vIII NEG |
| 1197047B | Asterand | 17.85 | 14.46 | 12.12 | −2.34 | tEGFR POS; vIII POS |
| 1199211B | Asterand | 18.37 | 13.11 | 13.12 | 0.01 | tEGFR POS; vIII POS |
| R14-0593 | Discovery Life | 20.76 | 17.13 | 13.97 | −3.16 | tEGFR POS; vIII POS |
| 1199394B | Asterand | 21.04 | 17.00 | 15.38 | −1.62 | tEGFR POS; vIII POS |
| 1180381B | Asterand | 22.74 | 14.78 | 13.41 | −1.37 | tEGFR POS; vIII POS |
| 1204786B | Asterand | 27.33 | 18.10 | 17.05 | −1.05 | tEGFR POS; vIII POS |

In Table 18, EGFRvIII CN is reported as "ND" (not detected) if there was no signal for the EGFRvIII target. For sample IDs R15-0028 and 1199219B, the EGFRvIII signal was detected from only 1 PCR replicate.

Out of the 32 specimens tested in this study, 6 were positive and 26 were negative for EGFRvIII. Positive and Negative status for EGFRvIII were determined by comparing the EGFRvIII CN values to a clinical cutoff value of 30.00 CN. The EGFRvIII result is reported as "POS" (positive) for specimens having a CN value less than or equal to 30.00 and "NEG" (negative) for specimens having a CN value greater than 30.00 or a CN value that was not detected. Relative expression of total EGFR for this study was determined by calculating the difference between mean ACT CN and mean tEGFR CN values, which is referred as delta CN (dCN). Delta CN values for each specimen were compared with a clinical cutoff value of −5.5. tEGFR results are reported as "POS" (positive) for specimens having a delta CN greater than or equal to −5.5 and "NEG" (negative) for specimens having a delta CN less than −5.5. Out of the 32 specimens tested in this study, 19 specimens were positive and 13 were negative for total EGFR.

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in the art are intended to be within the scope of the following claims.

We claim:

1. A composition for detecting EGFRvIII mRNA, the composition comprising a primer comprising a sequence according to SEQ ID NO: 1 or SEQ ID NO: 31, a primer comprising a sequence according to SEQ ID NO: 2, and a detectably labeled probe comprising a sequence according to SEQ ID NO: 3.

2. A composition for detecting EGFRvIII mRNA and for quantifying total EGFR mRNA, the composition comprising a primer comprising a sequence according to SEQ ID NO: 1 or SEQ ID NO: 31, a primer comprising a sequence according to SEQ ID NO: 2, a primer comprising a sequence according to SEQ ID NO: 7, a primer comprising a sequence according to SEQ ID NO: 8, a detectably labeled probe comprising a sequence according to SEQ ID NO: 3, and a detectably labeled probe comprising a sequence according to SEQ ID NO: 9 or SEQ ID NO: 32.

3. The composition of claim 2 further comprising a primer comprising a sequence according to SEQ ID NO: 13, a primer comprising a sequence according to SEQ ID NO: 14, and a detectably labeled probe comprising a sequence according to SEQ ID NO: 15.

4. The composition of claim 3 wherein the detectably labeled probe comprising a sequence according to SEQ ID NO: 3 comprises a first distinguishable fluorescent moiety, the detectably labeled probe comprising a sequence according to SEQ ID NO: 9 or SEQ ID NO: 32 comprises a second distinguishable fluorescent moiety, and the detectably labeled probe comprising a sequence according to SEQ ID NO: 15 comprises a third distinguishable fluorescent moiety.

5. A method for detecting EGFRvIII expression in a sample, the method comprising:
   a) mixing a patient sample with a composition comprising a primer comprising a sequence according to SEQ ID NO: 1 or SEQ ID NO: 31, a primer comprising a sequence according to SEQ ID NO: 2, and a detectably labeled probe comprising a sequence according to SEQ ID NO: 3 to provide a RT-PCR reaction mixture;
   b) reverse transcribing EGFRvIII mRNA to provide a EGFRvIII cDNA;
   c) amplifying the EGFRvIII cDNA to provide an EGFRvIII amplicon; and
   d) detecting the EGFRvIII amplicon,
   wherein detecting the EGFRvIII amplicon indicates the presence of EGFRvIII expression in the sample.

6. The method of claim 5 wherein the detecting comprises determination of a Ct value.

* * * * *